US006214835B1

(12) United States Patent
Matsuo et al.

(10) Patent No.: US 6,214,835 B1
(45) Date of Patent: Apr. 10, 2001

(54) DIHALOPROPENE COMPOUNDS INSECTICIDES CONTAINING THEM AS ACTIVE INGREDIENTS, AND INTERMEDIATES FOR THEIR PRODUCTION

(75) Inventors: Sanshiro Matsuo, Toyono-gun; Taro Hirose; Keiichi Izumi, both of Toyonaka; Masaya Suzuki, Takarazuka; Noriyasu Sakamoto, Toyonaka; Kazunori Tsushima, Sanda; Shigeru Saito, Toyonaka; Hirotaka Takano, Sanda, all of (JP)

(73) Assignee: Sumitomo Chemical Company, Limited, Osaka-fu (JP)

( * ) Notice: Subject to any disclaimer, the term of this patent is extended or adjusted under 35 U.S.C. 154(b) by 0 days.

(21) Appl. No.: 09/320,281

(22) Filed: Jun. 2, 1999

Related U.S. Application Data

(62) Division of application No. 09/153,859, filed on Sep. 16, 1998, now Pat. No. 6,028,100, and a division of application No. 08/913,879, filed as application No. PCT/JP96/00989 on Apr. 11, 1996, now Pat. No. 5,952,386.

(30) Foreign Application Priority Data

Apr. 18, 1995 (JP) .................................................. 7-092868
Jan. 9, 1996 (JP) .................................................. 8-001774

(51) Int. Cl.[7] .................................................. A61K 31/435

(52) U.S. Cl. .......................... 514/279; 514/277; 546/313; 546/314; 546/315; 546/323

(58) Field of Search .................................... 514/277, 279; 546/346, 348, 313, 314, 315, 323

(56) References Cited

U.S. PATENT DOCUMENTS

| | | | |
|---|---|---|---|
| 4,048,235 * | 9/1977 | Karrer | 260/612 R |
| 4,061,683 * | 12/1977 | Karrer | 260/613 R |
| 5,530,015 | 6/1996 | Sakamoto et al. . | |

FOREIGN PATENT DOCUMENTS

| | | |
|---|---|---|
| 9604228 | 2/1996 | (WO) . |

* cited by examiner

*Primary Examiner*—Sreeni Padmanabhan
(74) *Attorney, Agent, or Firm*—Birch, Stewart, Kolasch & Birch, LLP

(57) ABSTRACT

The present invention provides dihalopropene compounds of the general formula:

[I]

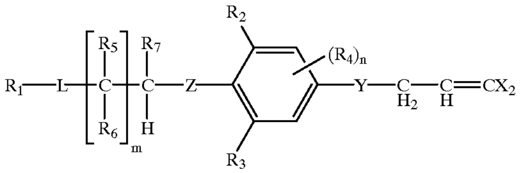

wherein $R_1$ is $C_1$–$C_{10}$ alkyl or the like; L is C(=O)NH or the like; $R_2$, $R_3$ and $R_4$ are independently halogen or the like; $R_5$, $R_6$ and $R_7$ are independently hydrogen or the like; m is an integer of 0 to 4; n is an integer of 0 to 2; X is chlorine or the like; Y is oxygen or the like; and Z is oxygen or the like, which have excellent insecticidal activity so that they are satisfactorily effective for the control of noxious insects.

22 Claims, No Drawings

DIHALOPROPENE COMPOUNDS INSECTICIDES CONTAINING THEM AS ACTIVE INGREDIENTS, AND INTERMEDIATES FOR THEIR PRODUCTION

This application is a divisional of application Ser. No. 09/153,859, filed on Sep. 16, 1998, now U.S. Pat. No. 6,028,100, and application No. 08/913,879, filed on Sep. 24, 1997, now U.S. Pat. No. 5,952,386. Application No. 08/913,879 is the national phase of PCT International Application No. PCT/JP96/00989 filed on Apr. 11.

TECHNICAL FIELD

The present invention relates to dihalopropene compounds, insecticides containing them as active ingredients, and intermediates for their production.

BACKGROUND ART

As disclosed in JP-A 48-86835/1973 and JP-A 49-1526/1974, for example, it is well known that some kinds of propene compounds can be used as active ingredients of insecticides.

In view of their insecticidal activity, however, it cannot always be said that these compounds are satisfactorily effective for the control of noxious insects.

DISCLOSURE OF INVENTION

The present inventors have intensively studied to find a compound having excellent insecticidal activity. As a result, they have found that particular dihalopropene compounds have satisfactory insecticidal activity for the control of noxious insects, thereby completing the present invention.

That is, the present invention provides dihalopropene compounds of the general formula:

[I]

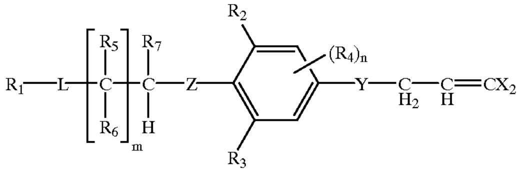

wherein m is an integer of 0 to 4;

n is an integer of 0 to 2;

X's are independently chlorine or bromine;

Y is oxygen, NH or sulfur; and

Z is oxygen, sulfur or $NR_{15}$ in which $R_{15}$ is hydrogen or $C_1$–$C_3$ alkyl;

$R_2$, $R_3$ and $R_4$ are independently halogen, $C_1$–$C_3$ haloalkyl or $C_1$–$C_3$ alkyl;

$R_5$, $R_6$ and $R_7$ are independently hydrogen, $C_1$–$C_3$ alkyl or trifluoromethyl;

L is C=W, C(=W)$NR_{13}$, $NR_{13}$C(=W), $SO_2NR_{13}$, $NR_{13}SO_2$, $NR_{13}$C(=$W_1$)—W, WC(=$W_1$)$NR_{13}$ or $NR_{14}$C(=W)$NR_{13}$ in which W and $W_1$ are independently oxygen or sulfur, and $R_{13}$ and $R_{14}$ are independently hydrogen, $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl or $C_3$–$C_5$ haloalkynyl;

$R_1$ is $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl, $C_3$–$C_5$ haloalkynyl, $C_2$–$C_7$ alkoxyalkyl, $C_2$–$C_7$ alkylthioalkyl, $C_3$–$C_6$ cycloalkyl optionally substituted with $C_1$–$C_4$ alkyl, $C_1$–$C_4$ alkoxy or $C_1$–$C_3$ haloalkoxy, $C_4$–$C_9$ cycloalkylalkyl optionally substituted with $C_1$–$C_4$ alkyl, $C_5$–$C_6$ cycloalkenyl optionally substituted with $C_1$–$C_4$ alkyl, $C_6$–$C_8$ cycloalkenylalkyl optionally substituted with $C_1$–$C_4$ alkyl, an optionally substituted heterocyclic group, $Q_1$, $Q_2$, $Q_3$ or $Q_4$ of the general formula:

[II]

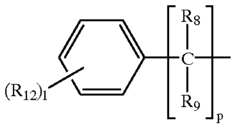

$Q_1$

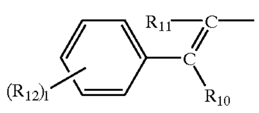

$Q_2$

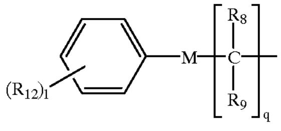

or $Q_3$

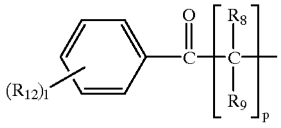

$Q_4$ in which M is oxygen, NH or sulfur, l is an integer of 0 to 5, p is an integer of 0 to 5, and q is an integer of 1 to 5;

$R_{12}$ is halogen, cyano, nitro, pentafluorosulfanyl ($F_5S$), $C_1$–$C_8$ alkyl, $C_1$–$C_3$ haloalkyl, $C_1$–$C_7$ alkoxy, $C_1$–$C_3$ haloalkoxy, $C_1$–$C_3$ alkylthio, $C_1$–$C_3$ haloalkylthio, $C_3$–$C_6$ alkenyloxy, $C_3$–$C_6$ haloalkenyloxy, $C_1$–$C_3$ hydroxyalkyl, $C_2$–$C_4$ alkenyl, $C_2$–$C_4$ haloalkenyl, $C_2$–$C_4$ alkynyl, $C_2$–$C_4$ alkynyloxy, $C_2$–$C_4$ haloalkynyl, $C_2$–$C_4$ haloalkynyloxy, $C_2$–$C_4$ alkoxyalkyl, $C_2$–$C_4$ alkylthioalkyl, $C_3$–$C_6$ cycloalkyl, $C_5$–$C_6$ cycloalkenyl, $C_2$–$C_5$ alkoxycarbonyl, $C_3$–$C_6$ cycloalkyloxy, $C_5$–$C_6$ cycloalkenyloxy, phenyl optionally substituted with halogen, $C_1$–$C_4$ alkyl, $C_1$–$C_3$ haloalkyl, $C_1$–$C_3$ alkoxy or $C_1$–$C_3$ haloalkoxy, phenoxy optionally substituted with halogen, $C_1$–$C_4$ alkyl, $C_1$–$C_3$ haloalkyl, $C_1$–$C_3$ alkoxy or $C_1$–$C_3$ haloalkoxy, benzyl optionally substituted with halogen, $C_1$–$C_4$ alkyl, $C_1$–$C_3$ haloalkyl, $C_1$–$C_3$ alkoxy or $C_1$–$C_3$ haloalkoxy, benzyloxy optionally substituted with halogen, $C_1$–$C_4$ alkyl, $C_1$–$C_3$ haloalkyl, $C_1$–$C_3$ alkoxy or $C_1$–$C_3$ haloalkoxy;

or when l is an integer of 2 to 5, adjacent two $R_{12}$ are combined together at their ends to form trimethylene or tetramethylene, methylenedioxy optionally substituted with halogen or $C_1$–$C_3$ alkyl, or ethylenedioxy optionally substituted with halogen or $C_1$–$C_3$ alkyl; and $R_8$, $R_9$, $R_{10}$ and $R_{11}$ are independently hydrogen, $C_1$–$C_3$ alkyl or trifluoromethyl.

The present invention further provides compounds of the general formula:

[III]

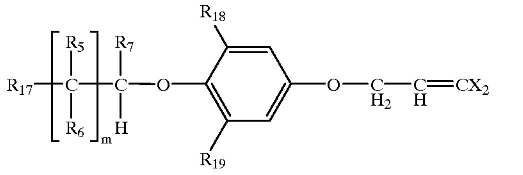

which are useful as intermediates for the production of some of the present compounds, wherein X's are independently chlorine or bromine; $R_{18}$ and $R_{19}$ are independently halogen or $C_1$–$C_3$ alkyl; $R_{17}$ is amino or carboxyl; $R_5$, $R_6$ and $R_7$ are independently hydrogen, $C_1$–$C_3$ alkyl or trifluoromethyl; and m is an integer of 0 to 4. More particularly, the present invention provides phenol compounds of the general formula:

[IV]

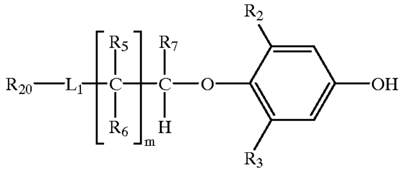

wherein $R_{20}$ is $Q_1$ as defined above, or 2-pyridyl, 2-pyrazinyl, 2-indolyl, 2-pyrrolyl, 2-quinolyl, 2-thienyl, 3-thienyl, 2-furyl, 3-furyl, 3-pyridyl or 4-pyridyl, each of which may be optionally substituted with $(R_{16})_s$ in which $R_{16}$ is halogen, nitro, cyano, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, ($C_1$–$C_2$ alkyl)aminocarbonyl, [di($C_1$–$C_2$ alkyl) amino]-carbonyl, phenyl optionally substituted with halogen, $C_1$–$C_4$ alkyl, $C_1$–$C_3$ haloalkyl, $C_1$–$C_4$ alkoxy or $C_1$–$C_3$ haloalkoxy, benzyl optionally substituted with halogen, $C_1$–$C_4$ alkyl, $C_1$–$C_3$ haloalkyl, $C_1$–$C_4$ alkoxy or $C_1$–$C_3$ haloalkoxy, phenoxy optionally substituted with halogen, $C_1$–$C_4$ alkyl, $C_1$–$C_3$ haloalkyl, $C_1$–$C_4$ alkoxy or $C_1$–$C_3$ haloalkoxy, benzyloxy optionally substituted with halogen, $C_1$–$C_4$ alkyl, $C_1$–$C_3$ haloalkyl, $C_1$–$C_4$ alkoxy or $C_1$–$C_3$ haloalkoxy, or pyridyloxy optionally substituted with halogen, $C_1$–$C_4$ alkyl, $C_1$–$C_3$ haloalkyl, $C_1$–$C_4$ alkoxy or $C_1$–$C_3$ haloalkoxy; and s is an integer of 0 to 7;

$R_2$ and $R_3$ are independently halogen, $C_1$–$C_3$ haloalkyl or $C_1$–$C_3$ alkyl;

$R_5$, $R_6$ and $R_7$ are independently hydrogen, $C_1$–$C_3$ alkyl or trifluoromethyl;

$L_1$ is C═W, C(═W)$NR_{131}$ or $SO_2NR_{131}$ in which W is oxygen or sulfur, and $R_{131}$ is hydrogen or $C_1$–$C_3$ alkyl.

As more specific examples of these phenol compounds, the present invention provides phenol compounds wherein $R_{20}$ is $Q_1$ in which p=0 or $R_1$ as defined above in which the 5- or 6-membered heterocyclic group is 2-pyridyl, 2-pyrazinyl, 2-indolyl, 2-pyrrolyl, 2-quinolyl, 2-thienyl, 3-thienyl, 2-furyl, 3-furyl, 3-pyridyl or 4-pyridyl; and phenol compounds wherein $R_{20}$ is $Q_1$ in which p=0 or $R_1$ as defined above in which the 5- or 6-membered heterocyclic group is 2-pyridyl, 2-pyrazinyl, 2-indolyl, 2-pyrrolyl, 2-quinolyl, 2-thienyl, 3-thienyl, 2-furyl, 3-furyl, 3-pyridyl or 4-pyridyl, and $L_1$ is C(═W)$NR_{131}$ or $SO_2NR_{131}$; and phenol compounds, wherein $R_{20}$ is $Q_1$ in which p=0 or $R_1$ as defined above in which the 5- or 6-membered heterocyclic group is 2-pyridyl, 2-pyrazinyl, 2-indolyl, 2-pyrrolyl, 2-quinolyl, 2-thienyl, 3-thienyl, 2-furyl, 3-furyl, 3-pyridyl or 4-pyridyl; $R_2$ and $R_3$ are halogen or $C_1$–$C_3$ alkyl; and $L_1$ is C(═W)$NR_{131}$ or $SO_2NR_{131}$; and the following compounds:

3,5-dichloro-4-(3-(N-(4-trifluoromethylphenyl) carbamoyl)propyloxy)phenol;

3,5-dichloro-4-(4-(N-(4-trifluoromethylphenyl) carbamoyl)butyloxy)phenol;

3,5-dichloro-4-(3-(N-(5-trifluoromethyl-2-pyridyl) carbamoyl)propyloxy)-phenol; and 3,5-dichloro-4-(4-(N-(5-trifluoromethyl-2-pyridyl) carbamoyl)butyloxy)-phenol.

DETAILED DESCRIPTION OF THE INVENTION

The variables in the above formulas for the present compounds and their intermediates can take the following specific examples.

Examples of the substituent on the optionally substituted heterocyclic group represented by $R_1$ are those of the formula: $(Ri_6)_s$ in which $R_{16}$ is halogen, nitro, cyano, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, ($C_1$–$C_2$ alkyl) aminocarbonyl, [di($C_1$–$C_2$ alkyl)-amino]carbonyl, phenyl optionally substituted with halogen, $C_1$–$C_4$ alkyl, $C_1$–$C_3$ haloalkyl, $C_1$–$C_4$ alkoxy or $C_1$–$C_3$ haloalkoxy, benzyl optionally substituted with halogen, $C_1$–$C_4$ alkyl, $C_1$–$C_3$ haloalkyl, $C_1$–$C_4$ alkoxy or $C_1$–$C_3$ haloalkoxy, phenoxy optionally substituted with halogen, $C_1$–$C_4$ alkyl, $C_1$–$C_3$ haloalkyl, $C_1$–$C_4$ alkoxy or $C_1$–$C_3$ haloalkoxy, benzyloxy optionally substituted with halogen, $C_1$–$C_4$ alkyl, $C_1$–$C_3$ haloalkyl, $C_1$–$C_4$ alkoxy or $C_1$–$C_3$ haloalkoxy, or pyridyloxy optionally substituted with halogen, $C_1$–$C_4$ alkyl, $C_1$–$C_3$ haloalkyl, $C_1$–$C_4$ alkoxy or $C_1$–$C_3$ haloalkoxy; and s is an integer of 0 to 7.

Examples of the halogen atom represented by $R_2$, $R_3$, $R_4$, $R_{12}$, $R_{16}$, $R_{18}$ or $R_{19}$, or present in $R_{12}$ or $R_{16}$, are fluorine, chlorine, bromine and iodine.

Examples of the $C_1$–$C_{10}$ alkyl group represented by $R_1$, $R_{13}$ or $R_{14}$ are methyl, ethyl, n-propyl, isopropyl, n-butyl, isobutyl, sec-butyl, tert-butyl, n-pentyl, isopentyl, neopentyl, tert-pentyl, n-hexyl, n-heptyl, isohexyl, n-octyl, n-nonyl, n-decyl, 1-ethylpropyl, 2-ethylbutyl, 1-methylpentyl, 1-ethylbutyl, 3-methylpentyl, 1,3-dimethylbutyl, 1-methylheptyl and 1-methyloctyl.

Examples of the $C_1$–$C_3$ alkyl group represented by $R_2$, $R_3$, $R_4$, $R_5$, $R_6$, $R_7$, $R_8$, $R_9$, $R_{10}$, $R_{11}$, $R_{15}$, $R_{18}$ or $R_{19}$ are methyl, ethyl, n-propyl and isopropyl.

Examples of the $C_1$–$C_8$ alkyl group represented by $R_{12}$ are methyl, ethyl, n-propyl, isopropyl, n-butyl, isobutyl, sec-butyl, tert-butyl, n-pentyl, isopentyl, neo-pentyl, tert-pentyl, 1-ethylpentyl, n-hexyl, isohexyl, 2-ethylbutyl, 1-methylpentyl, 1-ethylbutyl, 3-methylpentyl, 1,3-dimethylbutyl, n-heptyl, n-octyl and 1-methylheptyl.

Examples of the $C_1$–$C_2$ alkyl group present in $R_{16}$ are methyl and ethyl.

Examples of the $C_1$–$C_5$ haloalkyl group represented by $R_1$, $R_{13}$ or $R_{14}$ are trifluoromethyl, difluoromethyl, bromodifluoromethyl, 2,2,2-trifluoroethyl, perfluoroethyl, 2-fluoroethyl, 2-chloroethyl, 2-bromoethyl, 2-iodoethyl, 2,2-dichloroethyl, 2-bromo-1,1,2,2-tetrafluoroethyl, 1,1,2,2-tetrafluoroethyl, 2-chloro-1,1,2-trifluoroethyl, 2-bromo-1,1,2-trifluoroethyl, 2,2,2-trichloroethyl, 2,2,2-tribromoethyl, 3-chloropropyl, 3-bromopropyl, 3-fluoropropyl, 3-iodopropyl, 3,3,3-trifluoropropyl, 2,2,3,3,3-pentafluoropropyl, 1,1,2,3,3,3-hexafluoropropyl, 2-chloropropyl, 1-chloro-1-methylethyl, 1-bromo-1-methylethyl, 2-fluoro-1-(fluoromethyl)ethyl, 2-chloro-1-(chloromethyl)ethyl, 2-bromo-1-(bromomethyl)ethyl, 2,2,2-trifluoro-1-(trifluoromethyl)ethyl, 2,3-dibromopropyl, 4-fluorobutyl, 4-bromobutyl, 4-chlorobutyl, 4-iodobutyl, 2-(bromomethyl)-propyl, 3-chloro-2,2-dimethyl-n-propyl, 3-bromo-2,2-dimethylpropyl, 2,2,3,4,4,4-hexafluorobutyl, 3-bromo-(1-bromomethyl)propyl and 2,2,3,3,4,4,5,5-octafluoropentyl.

Examples of the $C_1$–$C_3$ haloalkyl group represented by $R_2$, $R_3$, $R_4$, $R_{12}$ or $R_{16}$, or present in $R_{12}$ or $R_{16}$, are trifluoromethyl, difluoromethyl, bromodifluoromethyl, 2,2,2-trifluoroethyl, 2-fluoroethyl, 2-chloroethyl, 2-bromoethyl, 1-fluoroethyl, 1-chloroethyl, 1-bromoethyl, 2,2,3,3,3-pentafluoropropyl, 3,3,3-trifluoropropyl, 1-fluoropropyl, 2-chloropropyl and 3-bromopropyl.

Examples of the $C_2$–$C_{10}$ alkenyl group represented by $R_1$, $R_{13}$ or $R_{14}$ are vinyl, allyl, homoallyl, isopropenyl, 2-butenyl, 1-methyl-2-propenyl, prenyl, 3-methyl-3-butenyl, 1-ethyl-2-propenyl, 2-ethyl-2-propenyl, 2-pentenyl, 2-methyl-2-butenyl, 1-methyl-2-butenyl, 2-methyl-3-butenyl, 4-pentenyl, 1-methyl-3-butenyl, 1-ethyl-2-propenyl, 1-propyl-2-propenyl, 3-hexenyl, 2-isopropyl-2-propenyl, 2-ethyl-2-butenyl, 2-methyl-2-pentenyl, 1-ethyl-2-butenyl, 1-methyl-4-pentenyl, 1,3-dimethyl-2-butenyl, 2-hexenyl, 4-hexenyl, 5-hexenyl, 1-n-propyl-2-propenyl, 1-allyl-3-butenyl, 2-heptenyl, 1,5-dimethyl-4-hexenyl, 1-pentyl-2-propenyl, 1,7-dimethyl-6-octenyl and geranyl.

Examples of the $C_2$–$C_6$ haloalkenyl group represented by $R_1$, $R_{13}$ or $R_{14}$ are 2-chloroethenyl, 2,2-dichloroethenyl, 3-chloro-2-propenyl, 3-bromo-2-propenyl, 2-chloro-2-propenyl, 2-bromo-2-propenyl, 3,3-dichloro-2-propenyl, 3,3-dibromo-2-propenyl, 3,3-difluoro-2-propenyl, 2-chloromethyl-2-propenyl, 4-chloro-2-butenyl, 4-chloro-2-butenyl, 3-chloro-4,4,4-trifluoro-2-butenyl, 4-bromo-3-fluoro-4,4-difluoro-2-butenyl, 3,4,4,4-tetrafluoro-2-butenyl, 4,4-dichloro-3-butenyl, 4,4-dibromo-3-butenyl, 4,4,4-trifluoro-3-butenyl, 3-chloro-2-butenyl and 6,6-dichloro-5-hexenyl.

Examples of the $C_2$–$C_4$ alkenyl group represented by $R_{12}$ or $R_{16}$ are vinyl, isopropenyl, 1-propenyl, 2-ethyl-1-propenyl, 1-methyl-1-propenyl, allyl, 2-methylpropenyl and 2-butenyl.

Examples of the $C_2$–$C_4$ haloalkenyl group represented by $R_{12}$ or $R_{16}$ are 2,2-dichloroethenyl, 2,2-dibromoethenyl, 3,3-dichloroallyl, 3,3-dibromoallyl, 2,3-dichloroallyl, 2,3-dibromoallyl, 2-chloro-2-propenyl, 3-chloro-2-propenyl, 2-bromo-2-propenyl and 3-chloro-2-butenyl.

Examples of the $C_3$–$C_9$ alkynyl group represented by $R_{12}$, $R_{13}$ or $R_{14}$ are 2-propynyl, 1-methyl-2-propynyl, 2-butynyl, 3-butynyl, 2-methyl-3-butynyl, 1-methyl-3-butynyl, 2-pentynyl, 4-pentynyl, 3-pentynyl, 1-ethyl-2-propynyl, 2-hexynyl, 3-hexynyl, 5-hexynyl, 1-pentyl-2-propynyl and 3-nonynyl.

Examples of the $C_3$–$C_5$ haloalkynyl group represented by $R_1$, $R_{13}$ or $R_{14}$ are 3-chloro-2-propynyl, 3-bromo-2-propynyl, 4-chloro-2-butynyl, 3-chloro-1-methyl-2-propynyl, 3-bromo-1-methyl-2-propynyl, 4-chloro-3-butynyl, 4-bromo-3-butynyl, 4-chloro-2-methyl-3-butynyl, 4-bromo-2-methyl-3-butynyl, 1-methyl-4-chloro-3-butynyl, 1-methyl-4-bromo-3-butynyl, 5-chloro-4-pentynyl, 5-bromo-4-pentynyl, 1-ethyl-3-chloro-2-propynyl and 1-ethyl-3-bromo-2-propynyl.

Examples of the $C_2$–$C_4$ alkynyl group represented by $R_{12}$ or $R_{16}$ are ethynyl, 1-propynyl, 2-propynyl and 1-methyl-2-propynyl.

Examples of the $C_2$–$C_4$ haloalkynyl group represented by $R_{12}$ or $R_{16}$ are chloroethynyl, bromoethynyl, iodoethynyl, 3-chloro-2-propynyl, 3-bromo-2-propynyl, 3-iodo-2-propynyl, 1-methyl-3-chloro-2-propynyl, 1-methyl-3-bromo-2-propynyl and 1-methyl-3-iodo-2-propynyl.

Examples of the $C_2$–$C_4$ alkynyloxy group represented by $R_{12}$ are ethynyloxy, 1-propynyloxy, 2-propynyloxy and 1-methyl-2-propynyloxy.

Examples of the $C_2$–$C_4$ haloalkynyloxy group represented by $R_{12}$ are chloroethynyloxy, 3-chloro-2-propynyloxy, 3-bromo-2-propynyloxy, 1-methyl-3-chloro-2-propynyloxy and 1-methyl-3-bromo-2-propynyloxy.

Examples of the $C_2$–$C_7$ alkoxyalkyl group represented by $R_1$ are methoxymethyl, 2-methoxyethyl, ethoxymethyl, isopropoxymethyl, 2-propoxymethyl, 1-methoxyethyl, 2-ethoxyethyl, 1-ethoxyethyl, 3-methoxypropyl, 2-methoxypropyl, 1-methoxypropyl, 2-methoxy-1-methylethyl, 2-propoxyethyl, 2-ethoxypropyl, 2-ethoxy-1-methylethyl, 2-methoxybutyl, 2-methoxy-1-ethylethyl, 3-ethoxypropyl, 3-methoxy-n-butyl, 3-methoxy-2-methylpropyl, 3-methoxy-1-methylpropyl, 2-isopropoxyethyl, 3-methoxybutyl, 3-methyl-3-methoxybutyl, 2-butoxyethyl and 2-butoxy-1-methylethyl.

Examples of the $C_2$–$C_4$ alkoxyalkyl group represented by $R_{12}$ are methoxymethyl, ethoxymethyl, n-propoxymethyl, isopropoxymethyl, 2-methoxyethyl, 1-methoxyethyl, 2-ethoxyethyl, 1-ethoxyethyl, 3-methoxypropyl, 2-methoxypropyl, 1-methoxypropyl and 2-methoxy-1-methylethyl.

Examples of the $C_2$–$C_7$ alkylthioalkyl group represented by $R_1$ are methylthiomethyl, ethylthiomethyl, 2-methylthioethyl, 1-methylthioethyl, propylthiomethyl, isopropylthiomethyl, 2-ethylthioethyl, 1-ethylthioethyl, 3-(methylthio)propyl, 2-(methylthio)propyl, 1-(methylthio)propyl, 1-methyl-2-methylthioethyl, 2-isopropylthioethyl, 2-(propylthio)ethyl, 2-methylthio-1-methylpropyl, 2-(methylthio)butyl, 1-ethyl-2-methylthioethyl, 2-(ethylthio)propyl, 2-ethylthio-1-methylethyl, 3-(ethylthio)propyl, 3-(methylthio)butyl, 2-methyl-3-(methylthio)propyl, 1-methyl-3-(methylthio)propyl, 2-tert-butylthioethyl, 2-isobutylthioethyl, 2-sec-butylthioethyl, 3-(tert-butylthio)propyl, 3-(isobutylthio)propyl and 3-(sec-butylthio)propyl.

Examples of the $C_2$–$C_4$ alkylthioalkyl group represented by $R_{12}$ are methylthiomethyl, ethylthiomethyl, propylthiomethyl, isopropylthiomethyl, 2-methylthioethyl, 1-methylthioethyl, 2-ethylthioethyl, 1-ethylthioethyl, 3-methylthiopropyl, 2-methylthiopropyl, 1-methylthiopropyl and 2-methylthio-1-methylethyl.

Examples of the $C_3$–$C_6$ cycloalkyl group optionally substituted with $C_1$–$C_4$ alkyl, $C_1$–$C_4$ alkoxy or $C_1$–$C_3$ haloalkoxy, which is represented by $R_1$, are cyclopropyl, cyclobutyl, 2-methoxycyclopentyl, 2-ethoxycyclopentyl, 2-propoxycyclopentyl, 2-isopropoxycyclopentyl, 2-butoxycyclopentyl, 2-isobutoxycyclopentyl, 2-sec-butoxycyclopentyl, 2-tert-butoxycyclopentyl, cyclopentyl, 3-methylcyclopentyl, 2-methylcyclopentyl, 3-methoxycyclohexyl, 3-ethoxycyclohexyl, 3-propoxycyclohexyl, 3-isopropoxycyclohexyl, 3-butoxycyclohexyl, 3-isobutoxycyclohexyl, 3-sec-butoxycyclohexyl, 3-tert-butoxycyclohexyl, 4-methoxycyclohexyl, 4-ethoxycyclohexyl, 4-propoxycyclohexyl, 4-isopropoxycyclohexyl, 4-butoxycyclohexyl, 4-isobutoxycyclohexyl, 4-sec-butoxycyclohexyl and 4-tert-butoxycyclohexyl.

Examples of the $C_4$–$C_9$ cycloalkylalkyl group optionally substituted with $C_1$–$C_4$ alkyl, which is represented by $R_1$, are cyclopropylmethyl, cyclobutylmethyl, 1-cyclopropylethyl, 2-methylcyclopropanemethyl, 2-(2-methylcyclopropyl)ethyl, cyclopentylniethyl, cyclohexylmethyl, 2-cyclohexylethyl, 3-cyclopentylpropyl and 3-cyclohexylpropyl.

Examples of the $C_5$–$C_6$ cycloalkenyl group optionally substituted with $C_1$–$C_4$ alkyl, which is represented by $R_1$, are 2-cyclohexenyl, 3,5,5-trimethyl-2-cyclohexenyl, 3-methyl-2-cyclohexenyl, 3-cyclohexenyl, 2-cyclopentenyl and 3-cyclopentenyl.

Examples of the $C_6$–$C_8$ cycloalkenylalkyl group optionally substituted with $C_1$–$C_4$ alkyl, which is represented by $R_1$, are (1-cyclopentenyl)methyl, (3-cyclohexenyl)-methyl and 2-(3-cyclohexenyl)ethyl.

Examples of the $C_3$–$C_6$ cycloalkyl group represented by $R_{12}$ or $R_{16}$ are cyclopropyl, cyclobutyl, cyclopentyl and cyclohexyl.

Examples of the $C_5$–$C_6$ cycloalkenyl group represented by $R_{12}$ are 1-cyclopentenyl, 2-cyclopentenyl, 3-cyclopentenyl, 1-cyclohexenyl, 2-cyclohexenyl and 3-cyclohexenyl.

Examples of the $C_3$–$C_6$ cycloalkyloxy group represented by $R_{12}$ are cyclopropyloxy, cyclobutyloxy, cyclopentyloxy and cyclohexyloxy.

Examples of the $C_5$–$C_6$ cycloalkenyloxy group represented by $R_{12}$ are 1-cyclopentenyloxy, 2-cyclopentenyloxy, 3-cyclopentenyloxy, 1-cyclohexenyloxy, 2-cyclohexenyloxy and 3-cyclohexenyloxy.

Examples of the $C_1$–$C_3$ alkoxy group present in $R_1$ or $R_{12}$ are methoxy, ethoxy, n-propoxy and isopropoxy.

Examples of the $C_1$–$C_7$ alkoxy group represented by $R_{12}$ are methoxy, ethoxy, 2-propoxy, isopropoxy, n-butoxy, sec-butoxy, isobutoxy, tert-butoxy, n-pentyloxy, isopentyloxy, neopentyloxy, tert-pentyloxy, (1-ethylpropyl)oxy, n-hexyloxy and n-heptyloxy.

Examples of the $C_1$–$C_3$ haloalkoxy group represented by $R_{12}$ or $R_{16}$, or present in $R_{12}$ or $R_{16}$, are trifluoromethoxy, difluoromethoxy, bromodifluoromethoxy, 2-fluoroethoxy, 2,2,2-trifluoroethoxy, 2-chloroethoxy, 2-bromoethoxy, 2-chloro-1,1,2-trifluoroethoxy, 2-bromo-1,1,2-trifluoroethoxy, 1,1,2,2-tetrafluoroethoxy, 1,2,2,3,3,3-hexafluoropropoxy, 3-fluoro-n-propoxy, 3-chloropropoxy, 3-bromopropoxy, 2,2,3,3,3-pentafluoropropoxy, 3,3,3-trifluoropropoxy and 1,1,2,2,2-pentafluoroethoxy.

Examples of the $C_1$–$C_3$ alkylthio group represented by $R_{12}$ or $R_{16}$ are methylthio, ethylthio, n-propylthio and isopropylthio.

Examples of the $C_1$–$C_3$ haloalkylthio group represented by $R_{12}$ or $R_{16}$ are trifluoromethylthio, difluoromethylthio, bromodifluoromethylthio, 2,2,2-trifluoroethylthio, 2-chloro-1,1,2-trifluoroethylthio, 2-bromo-1,1,2-trifluoroethylthio, 1,1,2,2-tetrafluoroethylthio, 2-chloroethylthio, 2-fluoroethylthio, 2-bromoethylthio, 3-fluoropropylthio, 3-chloro-n-propylthio, (3-bromopropyl)thio, 2,2,3,3,3-pentafluoropropylthio and 3,3,3-trifluoropropylthio.

Examples of the $C_3$–$C_6$ alkenylthio group represented by $R_{12}$ are allyloxy, 2-methylallyloxy, 2-butenyloxy, 3-methyl-2-butenyloxy, 2-methyl-2-butenyloxy, 2-pentenyloxy and 2-hexenyloxy.

Examples of the $C_3$–$C_6$ haloalkenyloxy group represented by $R_{12}$ are 3,3-dichloroallyloxy, 3,3-dibromoallyloxy, 2,3-dichloroallyloxy, 2,3-dibromoallyloxy, 2-chloro-2-propenyloxy, 3-chloro-2-propenyloxy, 2-bromo-2-propenyloxy and 3-chloro-2-butenyloxy.

Examples of the $C_1$–$C_3$ hydroxyalkyl group represented by $R_{12}$ are hydroxymethyl, 2-hydroxyethyl, 1-hydroxyethyl, 3-hydroxypropyl, 2-hydroxypropyl and 1-hydroxypropyl.

Examples of the $C_2$–$C_5$ alkoxycarbonyl group represented by $R_{12}$ are methoxycarbonyl, ethoxycarbonyl, n-propoxycarbonyl, isopropoxycarbonyl, n-butoxycarbonyl, isobutoxycarbonyl, sec-butoxycarbonyl and tert-butoxycarbonyl.

Examples of the $C_1$–$C_4$ alkyl group represented by $R_{16}$, or present in $R_1$, $R_{12}$ or $R_{16}$, are methyl, ethyl, n-propyl, isopropyl, n-butyl, isobutyl, sec-butyl and tert-butyl.

Examples of the $C_1$–$C_4$ alkoxy group represented by $R_{16}$, or present in $R_{16}$, are methoxy, ethoxy, n-propoxy, isopropoxy, n-butoxy, sec-butoxy, isobutoxy and tert-butoxy.

Examples of the $C_1$–$C_2$ alkylsulfinyl group represented by $R_{16}$ are methylsulfinyl and ethylsulfinyl.

Examples of the $C_1$–$C_2$ alkylsulfonyl group represented by $R_{16}$ are methylsulfonyl and ethylsulfonyl.

Examples of the $C_1$–$C_2$ haloalkylsulfinyl group represented by $R_{16}$ are trifluoromethylsulfinyl, 2,2,2-trifluoroethylsulfinyl and perfluoroethylsulfinyl.

Examples of the $C_1$–$C_2$ haloalkylsulfonyl group represented by $R_{16}$ are trifluoromethylsulfonyl, 2,2,2-trifluoroethylsulfonyl and perfluoroethylsulfonyl.

Examples of the ($C_1$–$C_2$ alkyl)aminocarbonyl group represented by $R_{16}$ are methylaminocarbonyl and ethylaminocarbonyl.

Examples of the [di($C_1$–$C_2$ alkyl)amino]carbonyl group represented by $R_{16}$ are dimethylaminocarbonyl, N-methyl-N-ethylaminocarbonyl and diethylaminocarbonyl.

Examples of the heterocyclic ring in the optionally substituted heterocyclic group represented by $R_1$ are hexamethylenimine, heptamethylenimine, 5- and 6-membered heterocyclic rings containing at least one oxygen, sulfur or nitrogen atom. Specific examples thereof include isoxazole, isothiazole, thiazole, 1,3,4-thiadiazole, pyrrole, furan, thiophene, pyrazole, imidazole, 1,2,3-triazole, 1,2,4-triazole, 1,2,3,4-tetrazole, pyridine, pyridazine, pyrimidine, pyrazine, 1,2,4-triazine, 1,3,5-triazine, indole, benzodioxane, pyrrolidine, 2,3-dihydro-4H-pyran-4-one, chromone, morpholine, 2-pyrroline, 3-pyrroline, 1,2,3,6-tetrahydropyrrolidine, piperazine, thiomorpholine, thiazolidine, benzofuran, thianaphthalene, imidazole, benzimidazole, benzotriazole, benzisoxazole, benzoxazole, benzothiazole, quinoline, isoquinoline, quinoxaline, quinazole, piperidine, piperazine, tetrahydrofuran, tetrahydropyran and pyrazoline.

The following are preferred examples of the present compounds:

dihalopropene compounds wherein $R_{13}$ and $R_{14}$ are independently hydrogen or $C_1$–$C_3$ alkyl;

dihalopropene compounds wherein $R_1$ is $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl or $C_3$–$C_5$ haloalkynyl;

dihalopropene compounds wherein L is $C({=}W)NR_{13}$;

dihalopropene compounds wherein L is $WC({=}W_2)NR_{13}$;

dihalopropene compounds wherein $R_1$ is $Q_1$, $Q_2$, $Q_3$ or $Q_4$;

dihalopropene compounds wherein $R_1$ is $Q_1$;

dihalopropene compounds wherein $R_1$ is $Q_1$, and L is C=W, $C({=}W)NR_{13}$ or $SO_2NR_3$;

dihalopropene compounds wherein $R_1$ is $Q_1$, and L is $C({=}W)NR_{13}$ or $SO_2NR_{13}$;

dihalopropene compounds wherein $R_1$ is $Q_1$, and L is $C({=}W)NR_{13}$;

dihalopropene compounds wherein $R_1$ is $Q_1$ in which p=0, and L is C=W, $C({=}W)NR_{13}$ or $SO_2NR_{13}$;

dihalopropene compounds wherein $R_1$ is $Q_1$ in which p=0, and L is $C({=}W)NR_{13}$ or $SO_2NR_{13}$;

dihalopropene compounds wherein $R_1$ is $Q_1$ in which p=0, and L is $C({=}W)NR_{13}$;

dihalopropene compounds wherein $R_2$, $R_3$ and $R_4$ are independently halogen or $C_1$–$C_3$ alkyl;

dihalopropene compounds wherein $R_2$ and $R_3$ are both chlorine, and $R_4$ is hydrogen;

dihalopropene compounds wherein Y and Z are both oxygen;

dihalopropene compounds wherein $R_5$, $R_6$ and $R_7$ are independently hydrogen or $C_1$–$C_3$alkyl; and dihalopropene compounds wherein $R_5$, $R_6$ and $R_7$ are all hydrogen.

The following are other preferred examples of the present compounds:

dihalopropene compounds wherein $R_1$ is a 5- or 6-membered heterocyclic group containing at least one oxygen, sulfur or nitrogen atom and optionally substituted with $(R_{16})_s$; and more particularly, dihalopropene compounds wherein the 5- or 6-membered heterocyclic group is 2-pyridyl, 2-pyrazinyl, 2-indolyl, 2-pyrrolyl, 2-quinolyl, 3-pyridyl, 4-pyridyl, 2-thienyl, 3-thienyl, 2-furyl or 3-furyl;

dihalopropene compounds wherein the 5- or 6-membered heterocyclic group is 2-furyl, 3-furyl, 2-thienyl, 3-thienyl, 2-pyrazinyl, 2-indolyl, 2-pyrrolyl, 2-quinolyl, 2-pyridyl, 3-pyridyl or 4-pyridyl, and L is C=W, $C({=}W)NR_{13}$ or $SO_2NR_{13}$;

dihalopropene compounds wherein the 5- or 6-membered heterocyclic group is 2-furyl, 3-furyl, 2-thienyl, 3-thienyl, 2-pyrazinyl, 2-indolyl, 2-pyrrolyl, 2-quinolyl, 2-pyridyl, 3-pyridyl or 4-pyridyl, and L is $C({=}W)NR_{13}$ or $SO_2NR_{13}$;

dihalopropene compounds wherein the 5- or 6-membered heterocyclic group is 2-furyl, 3-furyl, 2-thienyl, 3-thienyl, 2-pyrazinyl, 2-indolyl, 2-pyrrolyl, 2-quinolyl, 2-pyridyl, 3-pyridyl or 4-pyridyl, and L is $C({=}W)NR_{13}$; and dihalopropene compounds wherein the 5- or 6-membered heterocyclic group is 1-pyrrolidinyl or 1-piperidyl, and L is C=W.

The present compounds can be produced, for example, by the following production processes A–N.

(Production process A)

In this process, a compound of the general formula:

[V]

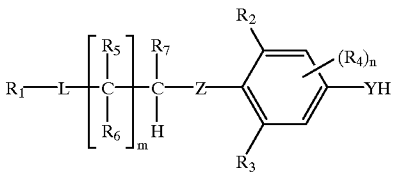

wherein $R_1$, $R_2$, $R_3$, $R_4$, $R_5$, $R_6$, $R_7$, L, Y, Z, m and n are each as defined above, is reacted with a compound of the general formula:

$$L_2—CH_2CH{=}CX_2 \qquad [VI]$$

wherein X is as defined above, and $L_2$ is halogen (e.g., chlorine, bromine, iodine), mesyloxy or tosyloxy.

The reaction is preferably effected in an inert solvent in the presence of a suitable base.

Examples of the solvent which can be used are ketones such as acetone, methyl ethyl ketone and cyclohexanone; ethers such as 1,2-dimethoxyethane, tetrahydrofuran, dioxane and dialkyl (e.g., $C_1$–$C_4$) ether (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$), such as sodium methoxide, sodium ethoxide and potassium tert-butoxide; and organic bases such as triethylamine and pyridine. If necessary, catalysts such as ammonium salts (e.g., benzyltriethylammonium chloride) may be added to the reaction system at a ratio of 0.01 to 1 mole per mole of the compound of general formula [V].

The reaction temperature is usually set within the range of −20° C. to +150° C. or the boiling point of a solvent used in the reaction, preferably −5° C. to +100° C. or the boiling point of a solvent used in the reaction.

The molar ratio of the starting materials and bases to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process B for the present compounds wherein Y is oxygen)

In this process, a compound of general formula [V] is reacted with an alcohol compound of the general formula:

$HO—CH_2CH=CX_2$ [VII]

wherein X is as defined above.

The reaction is preferably effected in the presence of a suitable dehydrating agent in an inert solvent, if necessary.

Examples of the dehydrating agent which can be used are dicyclohexylcarbodiimide, and dialkyl(e.g., $C_1$–$C_4$) azodicarboxylates (e.g., diethylazodicarboxylate, diisopropylazodicarboxylate)-trialkyl(e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of −20° C. to +200° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process C for the present compounds wherein Y is oxygen)

In this process, an aldehyde compound of the general formula:

[VIII]

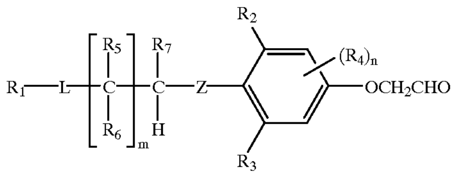

wherein $R_1$, $R_2$, $R_3$, $R_4$, $R_5$, $R_6$, $R_7$, L, Z, m and n are each as defined above, is reacted with carbon tetrachloride or carbon tetrabromide.

The reaction is preferably effected in the presence of a suitable trialkylphosphine or triarylphosphine, and if necessary, in the presence of metal zinc, in an inert solvent.

Examples of the solvent which can be used are hydrocarbons such as benzene, xylene and toluene; ethers such as diethyl ether, diisopropyl ether, tetrahydrofuran and dioxane; and halogenated hydrocarbons (exclusive of carbon tetrabromide and carbon tetrachloride) such as dichloromethane, 1,2-dichloroethane and chlorobenzene.

The reaction temperature is usually set within the range of −30° C. to +150° C. or the boiling point of a solvent used in the reaction.

Examples of the trialkyl(e.g., $C_1$–$C_{20}$)phosphine or triarylphosphine, which can be used in the reaction, are triphenylphosphine and trioctylphosphine. The metal zinc which is used, if necessary, is preferably in dust form.

The molar ratio of the starting materials and reagents to be used in the reaction can be freely determined, but the ratio is preferably such that carbon tetrabromide or tetrachloride, trialkylphosphine or triarylphosphine, and zinc are 2 moles, 2 or 4 moles (2 moles when zinc is used), and 2 moles, respectively, per mole of the aldehyde compound of general formula [VIII], or it is favorable to effect the reaction at a ratio closer thereto.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process D for the present compounds wherein Y and Z are both oxygen)

In this process, a compound of the general formula:

[IX]

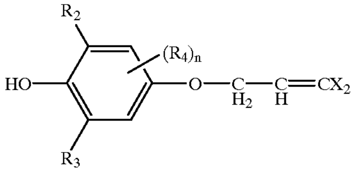

wherein $R_2$, $R_3$, $R_4$, X and n are each as defined above, is reacted with a compound of the general formula:

[X]

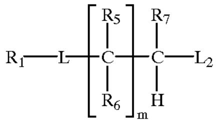

wherein $R_1$, $R_5$, $R_6$, $R_7$, L, $L_2$ and m are each as defined above.

The reaction is preferably effected in the presence of a suitable base in an inert solvent.

Examples of the solvent which can be used are ketones such as acetone, methyl ethyl ketone and cyclohexanone; ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine. If necessary, catalysts such as ammonium salts (e.g., benzyltriethylammonium chloride) may be added to the reaction system at a ratio of 0.01 to 1 mole per mole of the compound of general formula [IX].

The reaction temperature is usually set within the range of −20° C. to +150° C. or the boiling point of a solvent used in the reaction, preferably −5° C. to +100° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process E for the present compounds wherein Y and Z are both oxygen)

In this process, a compound of general formula [IX] is reacted with a compound of the general formula:

[XI]

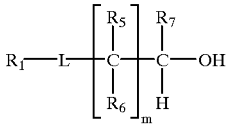

wherein $R_1$, $R_5$, $R_6$, $R_7$, L and m are as defined above.

The reaction is preferably effected in the presence of a suitable dehydrating agent in an inert solvent, if necessary.

Examples of the dehydrating agent which can be used are dicyclohexylcarbodiimide, and dialkyl(e.g., $C_1$–$C_4$) azodicarboxylates (e.g., diethylazodicarboxylate, diisopropylazodicarboxylate)-trialkyl(e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of −20° C. to +200° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process F for the present compounds wherein L is —C(═O)—$NR_{13}$—)

In this process, an amine compound of the general formula:

[XII]

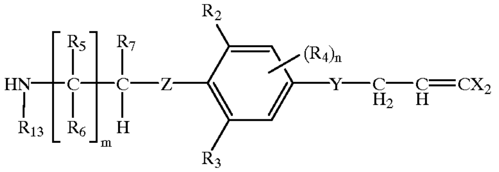

wherein $R_2$, $R_3$, $R_4$, $R_5$, $R_6$, $R_7$, $R_{13}$, X, Y, Z, m and n are each as defined above, is reacted with a carboxylic acid compound of the general formula:

$R_1$—C(═O)—V [XIII]

wherein $R_1$ is as defined above, and V is chlorine, bromine, hydroxyl, methoxy, ethoxy, propoxy or 1-imidazolyl.

(i) In the case where V in general formula [XIII] is chlorine, bromine or 1-imidazolyl, examples of the reaction solvent which can be used are ethers such as diethyl ether, tetrahydrofuran and dioxane; aromatic hydrocarbons such as benzene, toluene, xylene, chlorobenzene and pyridine; hydrocarbons such as n-hexane, n-heptane and cyclohexane; halogenated hydrocarbons such as methylene chloride, chloroform, carbon tetrachloride and 1,2-dichloroethane; esters such as ethyl acetate and methyl acetate; water; nitriles such as acetonitrile; polar solvents such as N,N-dimethylformamide, N,N-dimethylacetamide, N-methylpyrrolidone and dimethylsulfoxide; and mixtures thereof.

The reaction temperature is usually set within the range of −20° C. to +150° C. or the boiling point of a solvent used in the reaction, preferably 0° C. to 50° C.

The reaction is usually effected in the presence of a base such as sodium hydroxide, potassium hydroxide, sodium carbonate, potassium carbonate, triethylamine or pyridine at a ratio of 1 to 10 moles per mole of the compound of general formula [XIII].

When two phase reaction is effected with water as a solvent, the use of a phase transfer catalyst such as tetra-n-butylammonium bromide or benzyltriethylammonium chloride makes it possible to raise the reaction rate.

(ii) In the case where V in general formula [XIII] is hydroxyl, methoxy, ethoxy or propoxy, the reaction is usually effected without any solvent, or in a polar solvent such as N,N-dimethylformamide, N,N-dimethylacetamide, N-methylpyrrolidone or dimethylsulfoxide, or in an aromatic hydrocarbon solvent such as benzene, toluene, xylene or chlorobenzene, at a reaction temperature of 50° to 250° C.

If necessary, as a reaction catalyst, an acidic substance such as sulfuric acid, benzenesulfonic acid, p-toluenesulfonic acid or active silica gel, or a basic substance such as pyridine, triethylamine, sodium methoxide, sodium ethoxide or active alumina can be used at a weight which is 0.0001 to 1 time as much as the weight of the carboxylic acid compound of general formula [XIII].

The molar ratio of the materials and dehydrating agents to be used in the reaction can be freely determined, but it is favorable to effect the reaction at an equimolar ratio or a ratio closer thereto.

(iii) In the case where V in general formula [XIII] is hydroxyl, the following process can be used in the production.

That is, a carboxylic acid compound of general formula [XIII] is usually reacted with an amine compound of general formula [XII] in the presence of an inert organic solvent or without any solvent, thereby causing condensation by dehydration to give the desired compound of the present invention. Examples of the dehydrating agent are carbodiimides such as dicyclohexylcarbodiimide and 1-ethyl-3-(3-dimethylaminopropyl)carbodiimide; and inorganic dehydrating agents such as silicon tetrachloride. Examples of the inert organic solvent are non-aromatic hydrocarbons such as n-pentane, n-hexane, n-heptane and cyclohexane; aromatic hydrocarbons such as benzene, toluene and xylene; chlorinated hydrocarbons such as methylene chloride, chloroform, carbon tetrachloride, 1,2-dichloroethane, chlorobenzene and o-dichlorobenzene; esters such as ethyl acetate and methyl acetate; amides such as N,N-dimethylformamide, N,N-dimethylacetamide and N-methylpyrrolidone; nitrites such as acetonitrile; ethers such as diethyl ether, tetrahydrofuran and dioxane; and pyridine.

The reaction temperature is usually set within the range of −20° C. to +150° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction in case (i), (ii) or (iii), the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process G for the present compounds wherein L is $—NR_{13}—C—(=O)—$)

In this process, a compound of the general formula:

[XIV]

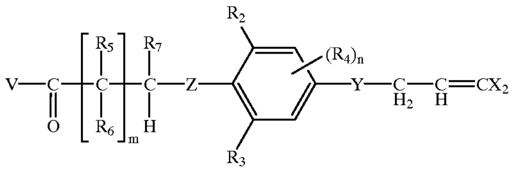

wherein $R_2$, $R_3$, $R_4$, $R_5$, $R_6$, $R_7$, X, Y, Z, V, m and n are each as defined above, is reacted with a compound of the general formula:

$R_1—NH—R_{13}$ or $R_{20}—H$ [XV]

wherein $R_1$ and $R_{13}$ are each as defined above, and $R_{20}$–H is a 5- or 6-membered heterocyclic group optionally substituted with $(R_{16})_s$ containing an NH moiety, or a 5- or 6-membered heterocyclic group containing at least one oxygen, sulfur or nitrogen atom and optionally substituted with $(R_{16})$s containing an NH moiety (e.g., pyrrole, piperidine, 2,6-dihydropyrrole, morpholine), in which $(R_{16})_s$ is as defined above.

(i) In the case where V in general formula [XIV] is chlorine, bromine or 1-imidazolyl, examples of the reaction solvent which can be used are ethers such as diethyl ether, tetrahydrofuran and dioxane; aromatic hydrocarbons such as benzene, toluene, xylene, chlorobenzene and pyridine; hydrocarbons such as n-hexane, n-heptane and cyclohexane; halogenated hydrocarbons such as methylene chloride, chloroform, carbon tetrachloride and 1,2-dichloroethane; esters such as ethyl acetate and methyl acetate; water; nitriles such as acetonitrile; polar solvents such as N,N-dimethylformamide, N,N-dimethylacetamide, N-methylpyrrolidone and dimethylsulfoxide; and mixtures thereof.

The reaction temperature is usually set within the range of −20° C. to +150° C. or the boiling point of a solvent used in the reaction, preferably 0° C. to 5020 C.

The reaction is usually effected in the presence of a base such as sodium hydroxide, potassium hydroxide, sodium carbonate, potassium carbonate, triethylamine or pyridine at a ratio of 1 to 10 moles per mole of the compound of general formula [XIV].

When two phase reaction is effected with water as a solvent, the use of a phase transfer catalyst such as tetra-n-butylammonium bromide or benzyltriethylammonium chloride makes it possible to raise the reaction rate.

(ii) In the case where V in general formula [XIV] is hydroxyl, methoxy, ethoxy or propoxy, the reaction is usually effected without any solvent, or in a polar solvent such as N,N-dimethylformamide, N,N-dimethylacetamide, N-methylpyrrolidone or dimethylsulfoxide, or in an aromatic hydrocarbon solvent such as benzene, toluene, xylene, or chlorobenzene, at a reaction temperature of 50° to 250° C.

If necessary, as a reaction catalyst, an acidic substance such as sulfuric acid, benzenesulfonic acid, p-toluenesulfonic acid or active silica gel, or a basic substance such as pyridine, triethylamine, sodium methoxide, sodium ethoxide or active alumina can be used at a weight which is 0.0001 to 1 time as much as the weight of the carboxylic acid compound of general formula [XIV].

The molar ratio of the materials to be used in the reaction can be freely determined, but it is favorable to effect the reaction at an equimolar ratio or a ratio closer thereto.

(iii) In the case where V in general formula [XIV] is hydroxyl, the following process can be used in the production.

That is, a compound of general formula [XIV] is usually reacted with an amine compound of general formula [XV] in the presence of an inert organic solvent or without any solvent, thereby causing condensation by dehydration to give the desired compound of the present invention. Examples of the dehydrating agent are carbodiimides such as dicyclohexylcarbodiimide and 1-ethyl-3-(3-dimethylaminopropyl)carbodiimide; and inorganic dehydrating agents such as silicon tetrachloride. Examples of the inert organic solvent are non-aromatic hydrocarbons such as n-pentane, n-hexane, n-heptane and cyclohexane; aromatic hydrocarbons such as benzene, toluene, xylene, chlorobenzene, pyridine and o-dichlorobenzene; chlorinated hydrocarbons such as methylene chloride, chloroform, carbon tetrachloride and 1,2-dichloroethane; esters such as ethyl acetate and methyl acetate; amides such as N,N-dimethylformamide, N,N-dimethylacetamide and N-methylpyrrolidone; nitrites such as acetonitrile; and ethers such as diethyl ether, tetrahydrofuran and dioxane.

The reaction temperature is usually set within the range of −20° C. to +150° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction in case (i), (ii) or (iii), the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process H for the present compounds wherein L is —C(═S)—$NR_{13}$— or —$NR_{13}$—C(═S)—)

In this process, the present compounds wherein L is —C(═O)—$NR_{13}$— or -$NR_{13}$—C(=O)—are reacted with phosphorus pentasulfide or the Lawesson's Reagent.

Examples of the solvent which can be used are aromatic hydrocarbons such as benzene, toluene, xylene, chlorobenzene, pyridine and quinoline. If necessary, a mixture of these solvents can be used.

The reaction temperature is usually set within the range of 0° C. to 150° C. or the boiling point of a solvent used in the reaction, preferably 20° C. to 150° C. or the boiling point of a solvent used in the reaction.

The molar ratio of the starting materials to be used in the reaction can be freely determined, but it is preferred that phosphorus pentasulfide or the Lawesson's Reagent is used at a ratio of 0.2 to 20 moles or 0.5 to 50 moles, respectively, per mole of the present compounds wherein L is —C(═O)—$NR_{13}$—or —$NR_{13}$—C(═O)—.

(Production process I for the present compounds wherein L is —$SO_2$—$NR_{13}$—)

In this process, an amine compound of general formula [XII] is reacted with a sulfonic acid compound of the general formula:

$R_1$—$SO_2$—$L_3$ [XVI]

wherein $R_1$ is as defined above, and $L_3$ is chlorine or bromine.

Examples of the solvent which can be used are ethers such as diethyl ether, tetrahydrofuran and dioxane; aromatic hydrocarbons such as benzene, toluene, xylene, chlorobenzene and pyridine; hydrocarbons such as n-hexane, n-heptane and cyclohexane; halogenated hydrocarbons such as methylene chloride, chloroform, carbon tetrachloride and 1,2-dichloroethane; esters such as ethyl acetate and methyl acetate; water; nitrites such as acetonitrile; polar solvents such as N,N-dimethylformamide, N,N-dimethylacetamide, N-methylpyrrolidone and dimethylsulfoxide; and mixtures thereof.

The reaction temperature is usually set within the range of −20° C. to +150° C. or the boiling point of a solvent used in the reaction, preferably 0° C. to 50° C.

The reaction is usually effected in the presence of a base, such as sodium hydroxide, potassium hydroxide, sodium carbonate, potassium carbonate, triethylamine or pyridine, at a ratio of 1 to 10 moles per mole of the compound of general formula [XVI].

When two phase reaction is effected with water as a solvent, the use of a phase transfer catalyst such as tetra-n-butylammonium bromide or benzyltriethylammonium chloride makes it possible to raise the reaction rate.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process J for the present compounds wherein L is —$NR_{13}$—$SO_2$—)

In this process, a sulfonic acid compound of the general formula:

[XVII]

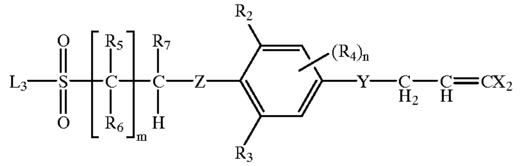

wherein $R_2$, $R_3$, $R_4$, $R_5$, $R_6$, $R_7$, X, Y, Z, $L_3$, m and n are each as defined above, is reacted with the compound of general formula [XV].

Examples of the solvent which can be used are ethers such as diethyl ether, tetrahydrofuran and dioxane; aromatic hydrocarbons such as benzene, toluene, xylene, chlorobenzene and pyridine; hydrocarbons such as n-hexane, n-heptane and cyclohexane; halogenated hydrocarbons such as methylene chloride, chloroform, carbon tetrachloride and 1,2-dichloroethane; esters such as ethyl acetate and methyl acetate; water; nitriles such as acetonitrile; polar solvents such as N,N-dimethylformamide, N,N-dimethylacetamide, N-methylpyrrolidone and dimethylsulfoxide; and mixtures thereof.

The reaction temperature is usually set within the range of −20° C. to +150° C. or the boiling point of a solvent used in the reaction, preferably 0° C. to 50° C.

The reaction is usually effected in the presence of a base, such as sodium hydroxide, potassium hydroxide, sodium carbonate, potassium carbonate, triethylamine or pyridine, at a ratio of 1 to 10 moles per mole of the compound of general formula [XVII].

When two phase reaction is effected with water as a solvent, the use of a phase transfer catalyst such as tetra-n-butylammonium bromide or benzyltriethylammonium chloride makes it possible to raise the reaction rate.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process K for the present compounds wherein L is —$NR_{13}$—C(═$W_1$)W—)

(The first step of production process K)

In this process, a compound of the general formula:

[XVIII]

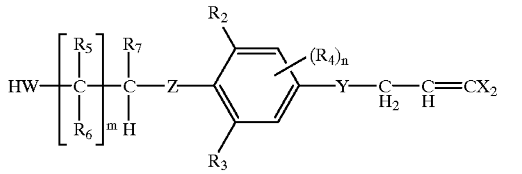

wherein $R_2$, $R_3$, $R_4$, $R_5$, $R_6$, $R_7$, W, X, Y, Z, m and n are each as defined above, is reacted with a (thio)isocyanate compound of the general formula:

$R_1$—N═C═$W_1$ [XIX]

wherein $R_1$ and $W_1$ are each as defined above, to give a carbamic acid derivative of the general formula:

[XX]

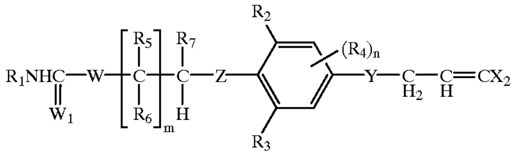

wherein $R_1$, $R_2$, $R_3$, $R_4$, $R_5$, $R_6$, $R_7$, W, $W_1$, X, Y, Z, m and n are each as defined above.

The reaction is preferably effected, if necessary, in the presence of an appropriate catalyst in a solvent having no influence thereon.

Examples of the solvent which can be used are hydrocarbons such as benzene and toluene; ethers such as diethyl ether, tetrahydrofuran and dioxane; polar solvents such as N,N-dimethylformamide, dimethylsulfoxide and hexamethylphosphoric acid triamide; halogenated hydrocarbons such as methylene chloride, chloroform, 1,2-dichloroethane and chlorobenzene; acetonitrile; and nitromethane. If necessary, a mixture of these solvents can be used.

Examples of the catalyst which can be used are organic bases such as triethylamine, pyridine and sodium acetate; and acids such as aluminum chloride, hydrogen chloride and boron trifluoride-ether complex ($BF_3$—$(C_2H_5)_2O$).

The reaction temperature is usually set within the range of −20° C. to the boiling point of a solvent used in the reaction, preferably −5° C. to the boiling point of a solvent used in the reaction.

The molar ratio of the materials to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention (wherein $R_{13}$ is H) can be isolated. Further, purification may be carried out, if necessary, by an ordinary technique such as chromatography, distillation or recrystallization.

(The second step of production process K)

In this process, a carbamic acid derivative of general formula [XX] is reacted with a halogenated compound of the general formula:

$$R_{13}—L_4 \qquad [XXI]$$

wherein $R_{13}$ is as defined above (however, it does not represent hydrogen) and $L_4$ is halogen (e.g., chlorine, bromine, iodine), to give the present compounds (wherein $R_{13}$ is not hydrogen).

The reaction is preferably effected in the presence of an appropriate catalyst in a solvent having no influence thereon.

Examples of the solvent which can be used are ketones such as acetone and methyl ethyl ketone; hydrocarbons such as benzene and toluene; ethers such as diethyl ether, tetrahydrofuran and dioxane; halogenated hydrocarbons such as methylene chloride, chloroform, 1,2-dichloroethane and chlorobenzene; acetonitrile; nitromethane; and pyridine. If necessary, a mixture of these solvents can be used.

Examples of the base which can be used are carbonates of alkali metals, such as potassium carbonate; hydrides of alkali metals, such as sodium hydride; and organic bases such as sodium methoxide, sodium ethoxide, triethylamine and pyridine.

The reaction temperature is usually set within the range of −10° C. to the boiling point of a solvent used in the reaction.

The molar ratio of the materials to be used in the reaction can be freely determined, but it is preferred that the halogenated compound of general formula [XXI] and the base are used at ratios of 1 to 2 moles and 0.9 to 20 moles, respectively, per mole of the carbamic acid derivative of general formula [XX].

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process L for the present compounds wherein L is —WC(=$W_1$)—$NR_{13}$—)

In this process, an amine compound of general formula [XII] is reacted with a compound of the general formula:

$$R_1—W—C(=W_1)—L_3 \qquad [XXII]$$

wherein $R_1$, W, $W_1$ and $L_3$ are each as defined above.

The reaction is preferably effected in the presence of an appropriate catalyst in a solvent having no influence thereon.

Examples of the base which can be used are carbonates of alkali metals, such as potassium carbonate; and organic bases such as triethylamine and pyridine. If necessary, a catalyst such as ammonium salts (e.g., benzyltriethylammonium chloride) may be added to the reaction system.

Examples of the solvent which can be used are ketones such as acetone and methyl ethyl ketone; hydrocarbons such as benzene and toluene; ethers such as diethyl ether, tetrahydrofuran and dioxane; halogenated hydrocarbons such as methylene chloride, chloroform, 1,2-dichloroethane and chlorobenzene; acetonitrile; and nitromethane. If necessary, a mixture of these solvents or a mixture of these solvents and water can be used.

The reaction temperature is usually set within the range of −20° C. to the boiling point of a solvent used in the reaction, preferably −5° C. to the boiling point of a solvent used in the reaction.

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

(Production process M for the present compounds wherein L is —$NR_{14}$—C(=W)$NR_{13}$—)

(The first step of production process M)

In this process, an amine compound of general formula [XII] is reacted with a (thio)isocyanate compound of general formula [XIX] to give an urea derivative compound of the general formula:

[XXIII]

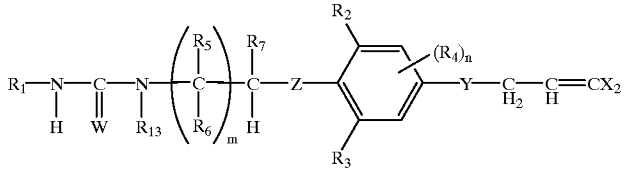

wherein $R_1$, $R_2$, $R_3$, $R_4$, $R_5$, $R_6$, $R_7$, $R_{13}$, W, X, Y, Z, m and n are each as defined above.

Examples of the solvent which can be used are hydrocarbons such as benzene and toluene; ethers such as diethyl ether, tetrahydrofuran and dioxane; polar solvents such as N,N-dimethylformamide, dimethylsulfoxide and hexamethylphosphoric acid triamide; halogenated hydrocarbons such as methylene chloride, chloroform, 1,2-dichloroethane and chlorobenzene; acetonitrile; and nitromethane. If necessary, a mixture of these solvents can be used.

The reaction temperature is usually set within the range of −20° C. to the boiling point of a solvent used in the reaction, preferably −5° C. to the boiling point of a solvent used in the reaction.

The molar ratio of the materials to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention (wherein $R_{14}$ is H) can be isolated. Further, purification may be carried out, if necessary, by an ordinary technique such as chromatography, distillation or recrystallization.

(The second step of production process M)

In this process, an urea derivative compound of general formula [XXIII] is reacted with a compound of the general formula:

$$R_{14}—L_4 \qquad [XXIV]$$

wherein $R_{14}$ and $L_4$ are each as defined above, to give the present compounds (wherein $R_{14}$ is not hydrogen).

The reaction is preferably effected in the presence of an appropriate catalyst in a solvent having no influence thereon.

Examples of the solvent which can be used are ketones such as acetone and methyl ethyl ketone; hydrocarbons such as benzene and toluene; ethers such as diethyl ether, tetrahydrofuran and dioxane; halogenated hydrocarbons such as methylene chloride, chloroform, 1,2-dichloroethane and chlorobenzene; acetonitrile; nitromethane; and pyridine. If necessary, a mixture of these solvents can be used.

Examples of the base which can be used are carbonates of alkali metals, such as potassium carbonate; hydrides of alkali metals, such as sodium hydride; and organic bases such as sodium methoxide, sodium ethoxide, triethylamine and pyridine.

The reaction temperature is usually set within the range of −10° C. to the boiling point of a solvent used in the reaction.

The molar ratio of the materials to be used in the reaction can be freely determined, but it is preferred that the compound of general formula [XXIV] and the base are used at ratios of 1 to 2 moles and 0.9 to 20 moles, respectively, per mole of the urea derivative compound of general formula [XXIII].

After completion of the reaction, the reaction mixture is subjected to ordinary post-treatments such as organic solvent extraction and concentration, and the desired compound of the present invention can be isolated. Further, purification may be carried out, if necessary, by an ordinary technique such as chromatography, distillation or recrystallization.

When any one of the present compounds has an asymmetric carbon atom, it is to be construed to include its optically active isomers (i.e., (+)-form and (−)-form) having biological activity and their mixtures at any ratio. When any one of the present compounds exhibits geometrical isomerism, it is to be construed to include its geometrical isomers (i.e., cis-form and trans-form) and their mixtures at any ratio.

The following are specific examples of the present compounds; however, the present invention is not limited to these examples.

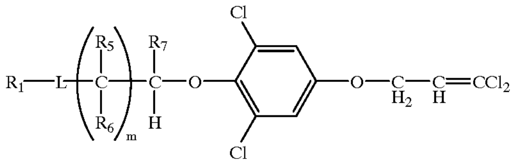

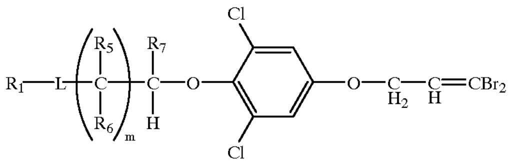

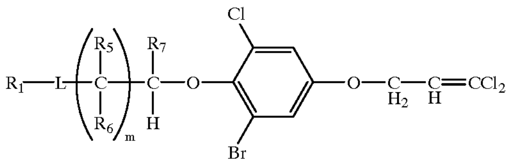

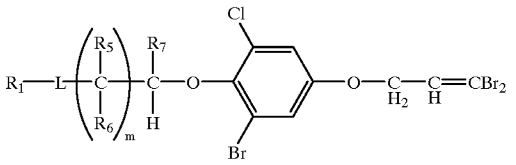

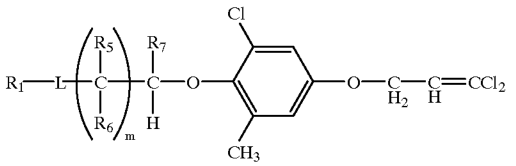

-continued
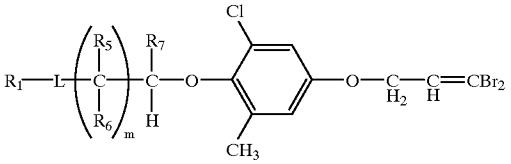
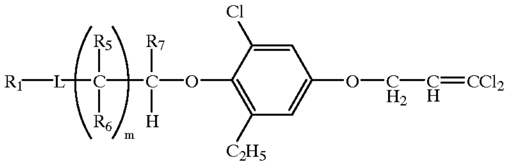
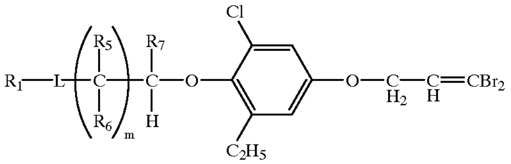
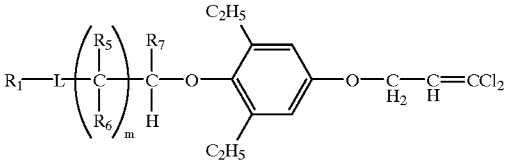
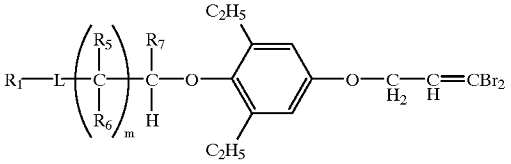
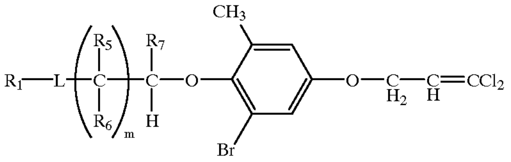
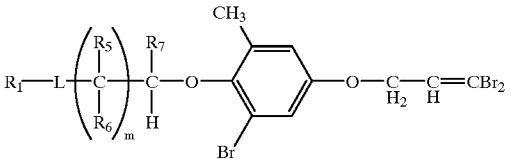
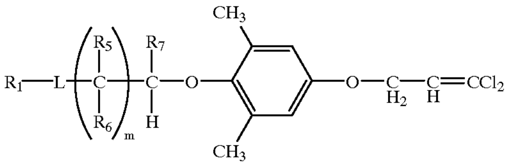
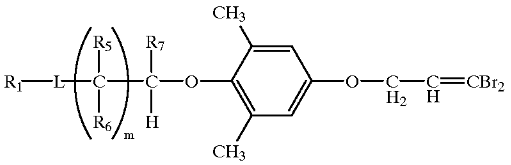
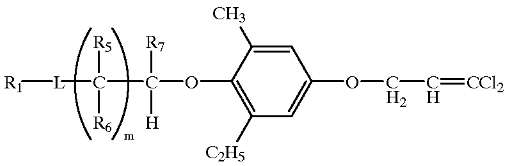
-continued
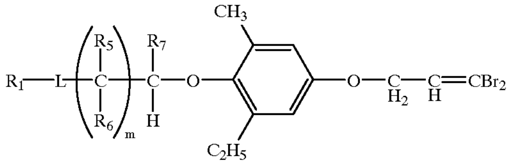
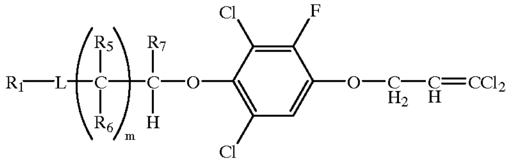
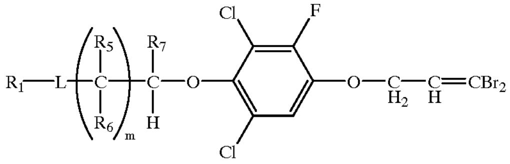
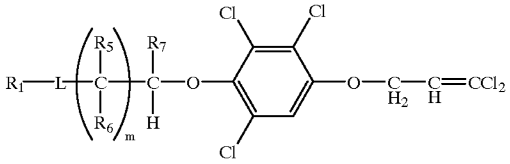
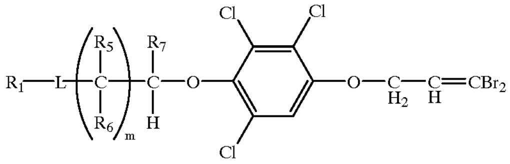
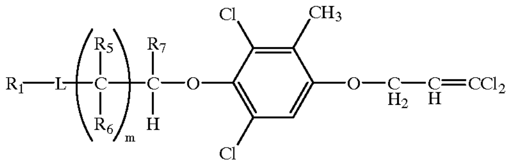
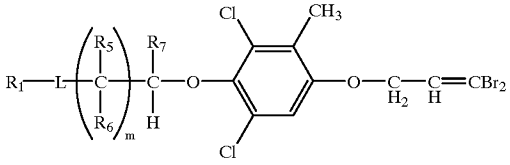
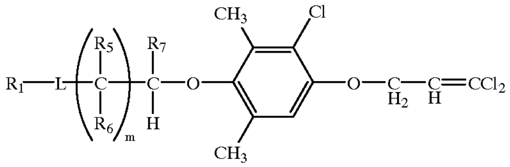
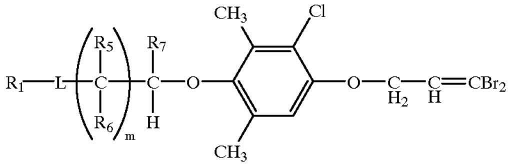
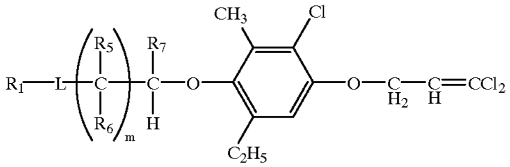

-continued
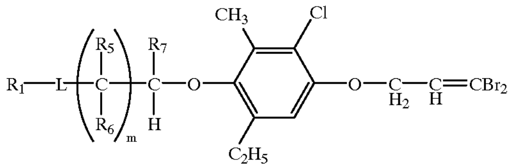
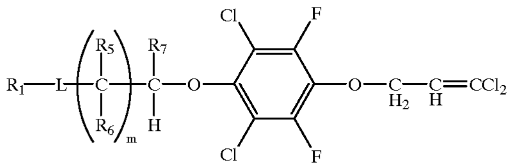
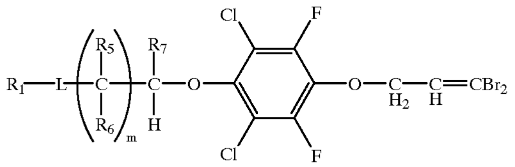
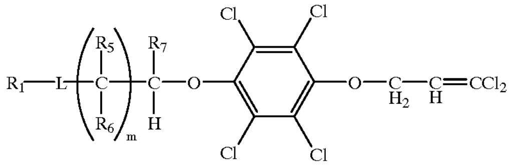
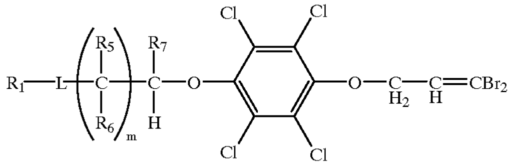
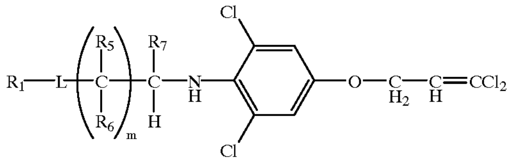
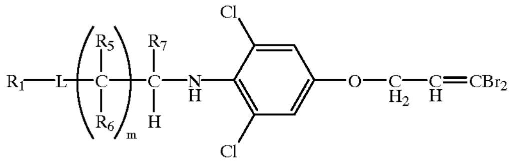
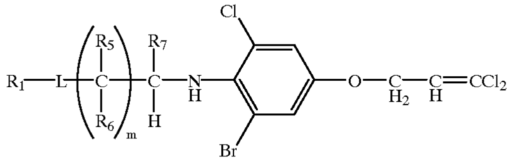
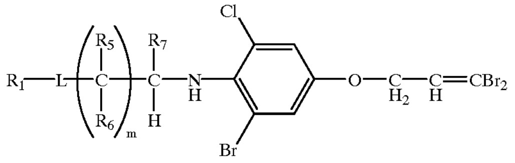
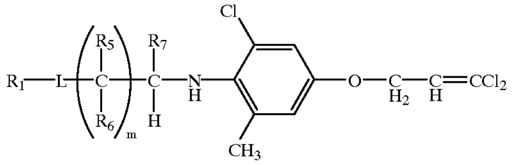
-continued
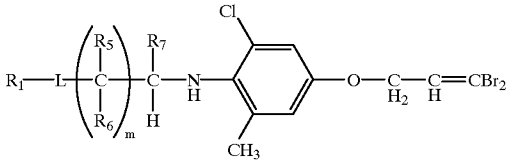
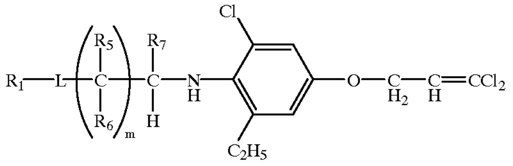
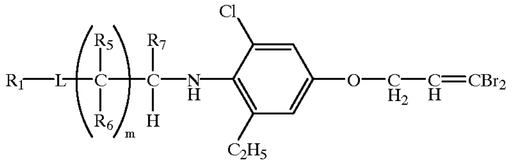
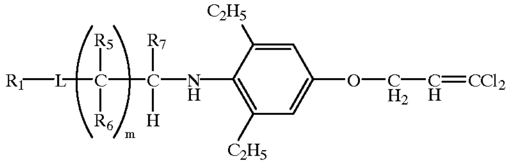
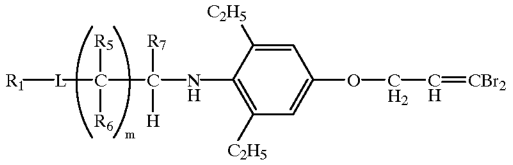
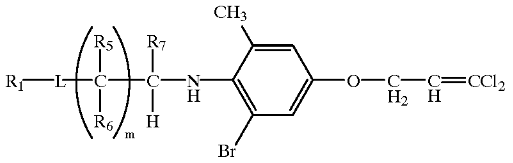
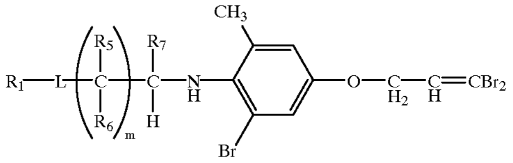
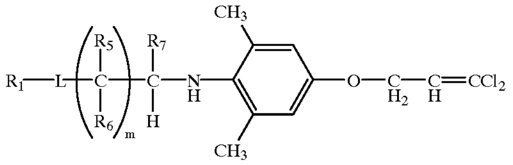
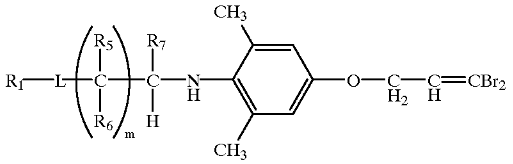
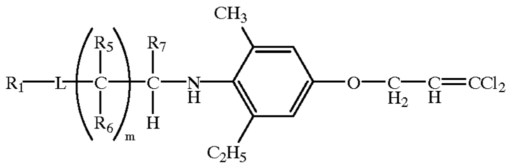

-continued
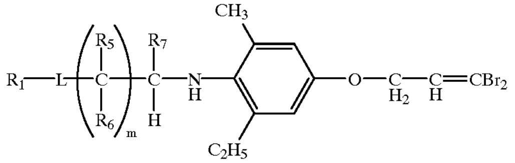
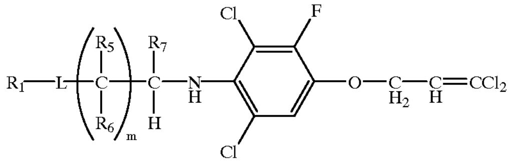
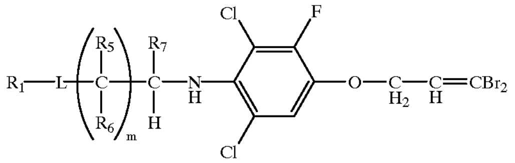
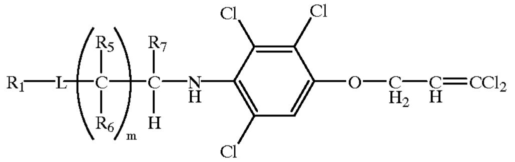
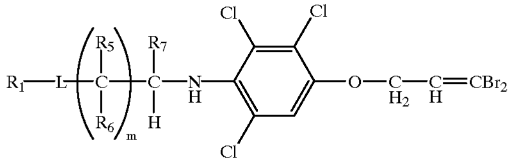
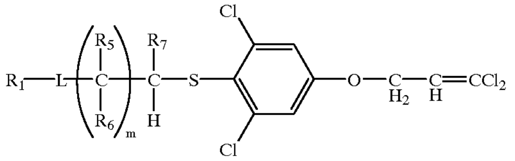
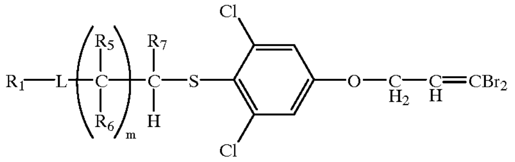
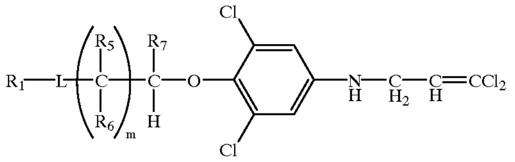
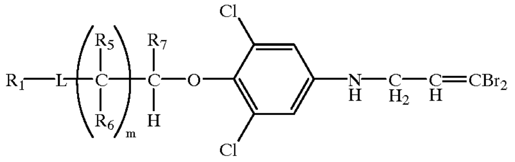
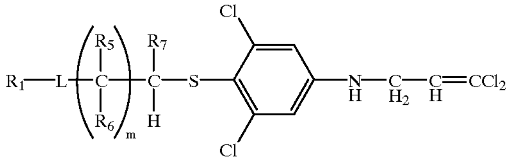
-continued
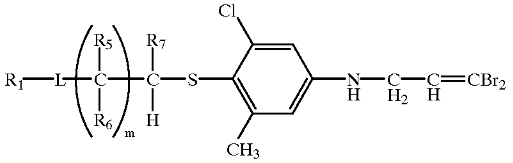
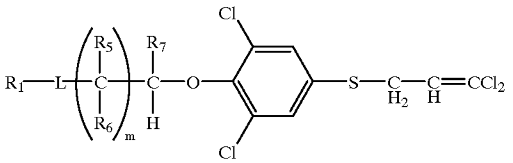
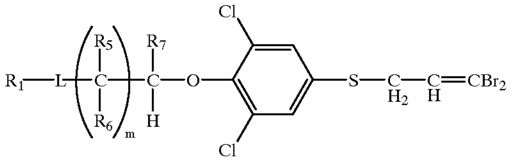
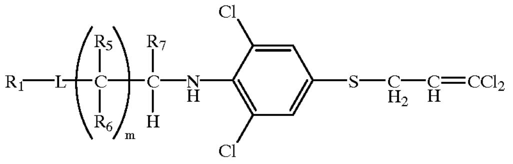
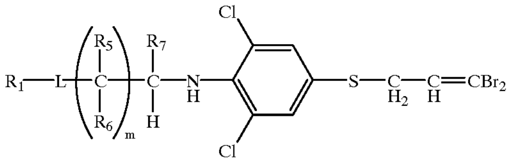
wherein 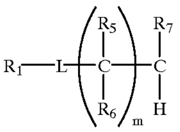 =
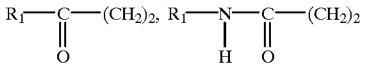
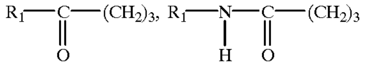
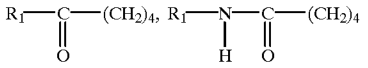
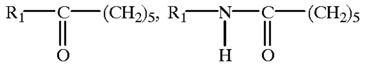
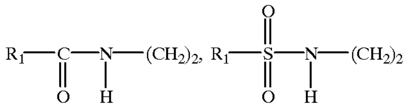
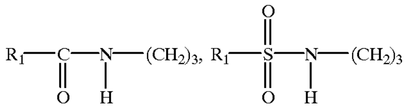
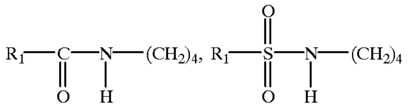
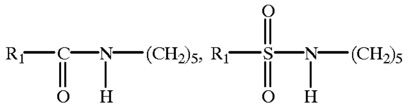

-continued
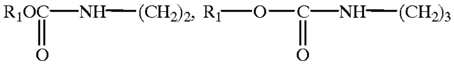
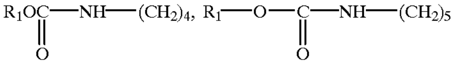
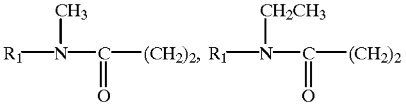
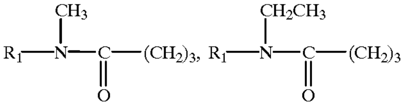
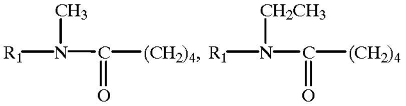
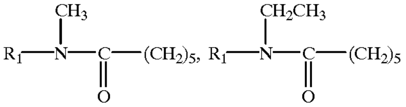
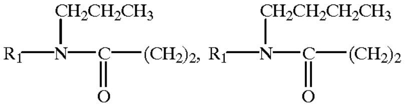
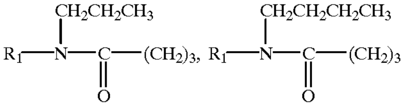
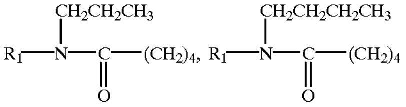
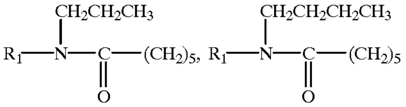
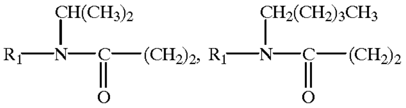
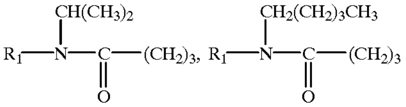
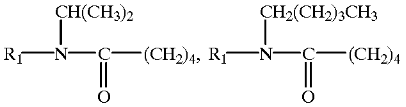
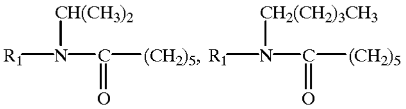
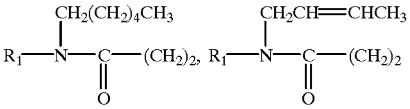
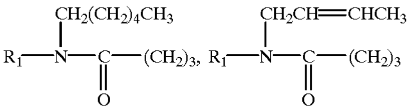
-continued
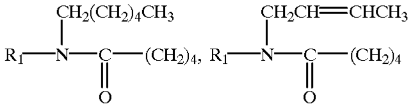
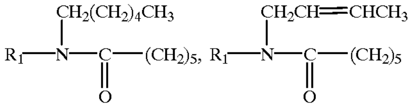
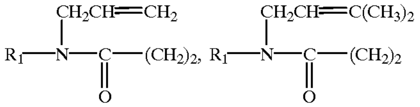
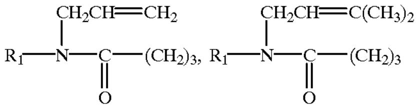
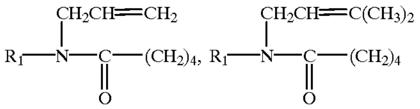
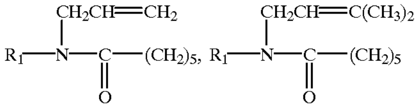
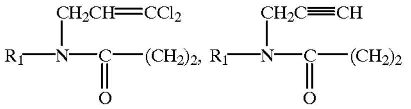
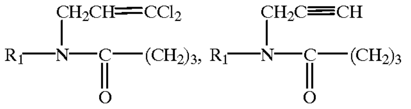
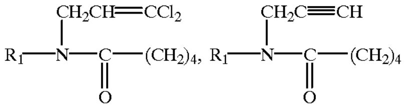
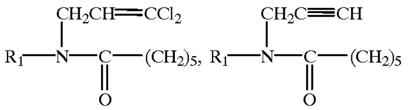
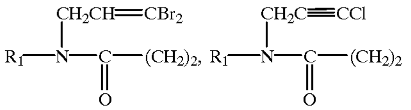
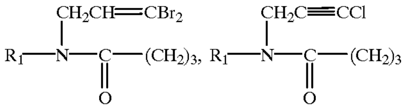
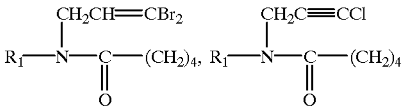
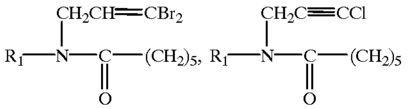
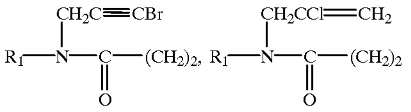

-continued

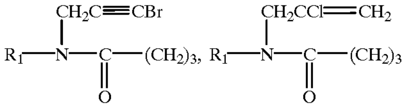

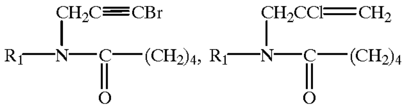

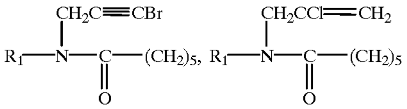

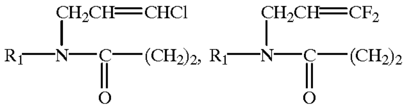

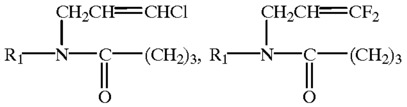

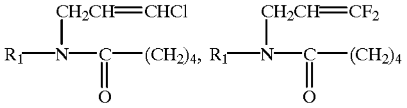

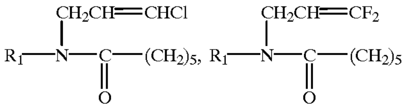

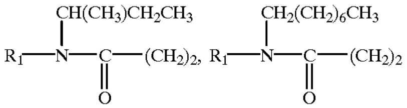

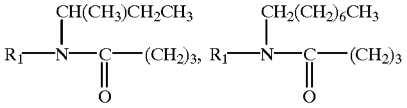

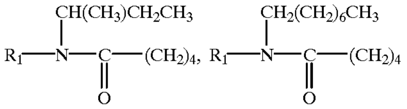

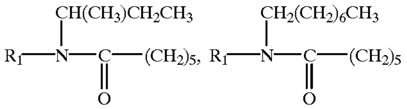

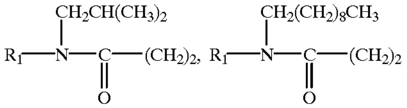

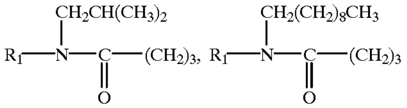

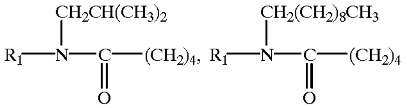

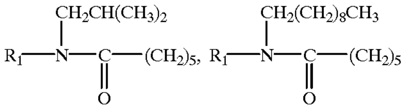

-continued

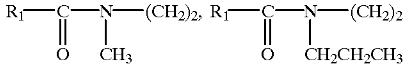

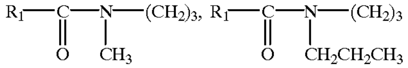

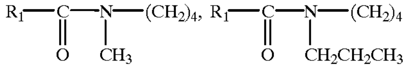

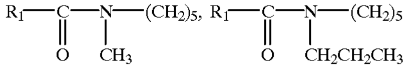

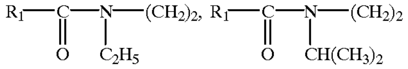

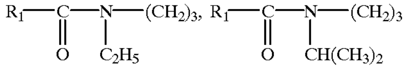

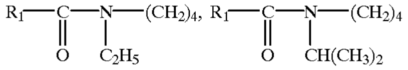

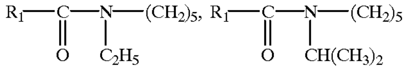

(in which $R_1$ is as defined in table 1 to 7)

TABLE 1

| $R^1$ | $R^1$ |
|---|---|
| $CH_3$— | $(CH_3)_2CHCH_2CH(CH_3)$— |
| $C_2H_5$— | $CH_3(CH_2)_5CH(CH_3)$— |
| $CH_3CH_2CH_2$— | $CH_3(CH_2)_6CH(CH_3)$— |
| $(CH_3)_2CH$— | $CF_3$— |
| $CH_3(CH_2)_2CH_2$— | $CF_2H$— |
| $(CH_3)_2CHCH_2$— | $CF_2Br$— |
| $CH_3CH_2CH(CH_3)$— | $CF_3CH_2$— |
| $(CH_3)_3C$— | $CF_3CF_2$— |
| $CH_3(CH_2)_3CH_2$— | $FCH_2CH_2$— |
| $(CH_3)_2CHCH_2CH_2$— | $ClCH_2CH_2$— |
| $(CH_3)_3CCH_2$— | $BrCH_2CH_2$— |
| $CH_3CH_2C(CH_3)_2$— | $ICH_2CH_2$— |
| $CH_3(CH_2)_4CH_2$— | $(Cl)_2CHCH_2$— |
| $(CH_3)_2CHCH_2CH_2CH_2$— | $BrCF_2CF_2$— |
| $CH_3(CH_2)_5CH_2$— | $CF_2HCF_2$— |
| $CH_3(CH_2)_6CH_2$— | $CFClHCF_2$— |
| $CH_3(CH_2)_7CH_2$— | $CF_2BrCFH$— |
| $CH_3(CH_2)_8CH_2$— | $ClCH_2CH_2CH_2$— |
| $(C_2H_5)_2CH$— | $BrCH_2CH_2CH_2$— |
| $(C_2H_5)_2CHCH_2$— | $FCH_2CH_2CH_2$— |
| $CH_3(CH_2)_3CH(CH_3)$— | $ICH_2CH_2CH_2$— |
| $CH_3(CH_2)_2CH(C_2H_5)$— | $CF_3CH_2CH_2$— |
| $CH_3CH_2CH(CH_3)(CH_2)_2$— | $CF_3CF_2CH_2$— |

TABLE 2

| | |
|---|---|
| $CF_3CFHCF_2$— | $CF_3CH(CF_3)$— |
| $FCH_2(CH_2)_3$— | $CH_2$=CH— |
| $BrCH_2(CH_2)_3$— | CHCl=CH— |
| $ClCH_2(CH_2)_3$— | $CCl_2$=CH— |
| $ICH_2(CH_2)_3$— | $CH_2$=$CHCH_2$— |
| $ClC(CH_3)_2CH_2$— | $CH_2$=$CHCH_2CH_2$— |
| $FCH_2(CH_2)_4$— | $(CH_3)_2C$=$CH(CH_2)_2(CH_3)C$=$CHCH_2$— |
| $BrCH_2(CH_2)_4$— | $(CH_2$=CH$)(CH_3CH_2CH_2)$CH— |
| $ClCH_2(CH_2)_4$— | $(CH_2$=$CHCH_2)_2$CH— |
| $ICH_2(CH_2)_4$— | $CH_2$=$C(CH_3)CH_2$— |
| $CH_3CHClCH_2$— | $(CH_3)_2C$=$CHCH_2$— |
| $CH_3CH(CH_2Br)CH_2$— | CH=$C(CH_3)CH_2CH_2$— |
| $CH_2ClC(CH_3)_2CH_2$— | $(CH_2$=CH$)(CH_3CH_2)$CH— |
| $CH_2BrC(CH_3)_2CH_2$— | ClCH=$CHCH_2$— |
| $CH_2BrCHBrCH_2$— | $CH_3CH$=$CHCH_2$— |
| $CCl_3CH_2$— | |

TABLE 2-continued

| | |
|---|---|
| $CBr_3CH_2$— | $BrCH=CHCH_2$— |
| $CF_2HCF_2CH_2$— | $CH_2=CClCH_2$— |
| $CF_3CFHCF_2CH_2$— | $CH_2=CBrCH_2$— |
| $CF_2H(CF_2)_3CH_2$— | $CH_2=C(CH_2Cl)CH_2$— |
| $CH_2ClCH(CH_3)$— | $ClCH_2CH=CHCH_2$— |
| $CH_2BrCH(CH_3)$— | $CH_3CH_2CH=CHCH_2CH_2$— |
| $CH_2FCH(CH_2F)$— | $ClCH_2CH=CHCH_2$— |
| $CH_2ClCH(CH_2Cl)$— | $(Cl_2)C=CHCH_2$— |
| $CH_2BrCH(CH_2Br)$— | $(Br_2)C=CHCH_2$— |
| $CH_2BrCH_2CH(CH_2Br)$— | $(F_2)C=CHCH_2$— |

TABLE 3

| | |
|---|---|
| $(CF_3)(Cl)C=CHCH_2$— | $CH_2=CHCH(CH_3CH_2CH_2)$— |
| $(F)(CF_2Br)C=CHCH_2$— | $(CH_3)_2=CH(CH_2)_2CH(CH_3)$— |
| $(CF_3)(F)C=CHCH_2$— | $CH_3(CH_2)_3CH_2CH(CH=CH_2)$— |
| $(Cl)_2C=CHCH_2CH_2$— | $(CH_3)_2C=CH(CH_2)_2$ |
| $(Br)_2C=CHCH_2CH_2$— | —$CH(CH_3)CH_2CH_2$— |
| $CH_2=C(CH(CH_3)_2)CH_2$— | $(CH_3)(Cl)C=CHCH_2$— |
| $CH_3CH=C(C_2H_5)CH_2$— | $(Cl)_2C=CH(CH_2)_3CH_2$— |
| $CH_2=C(C_2H_5)CH_2$— | $CH\equiv CCH(CH_3)$— |
| $C_2H_5CH=C(CH_3)CH_2$— | $CH_3C\equiv CCH_2$— |
| $C_2H_5CH=CHCH_2$— | $HC\equiv CCH_2$— |
| $CH_3CH=C(CH_3)CH_2$— | $HC\equiv CCH_2CH_2$— |
| $CH_3(CH_2)_3CH=CHCH_2$— | $CH_3CH_2CH_2C\equiv CCH_2$— |
| $CH_2=CHCH(CH_3)$— | $CH_3CH_2C\equiv CCH_2CH_2$— |
| $CH_3CH=CHCH(CH_3)$— | $HC\equiv CCH(CH_3)CH_2$— |
| $CH_3CH=CHCH(C_2H_5)$— | $HC\equiv CCH(CH_3(CH_2)_4)$— |
| $CH_2=CHCH_2CH_2CH(CH_3)$— | $HC\equiv CCH_2CH(CH_3)$— |
| $(CH_3)_2C=CHCH(CH_3)$— | $CH_3CH_2C\equiv CCH_2$— |
| $CF_3CH=CHCH_2$— | $HC\equiv CCH_2CH_2CH_2$— |
| $CH_2=CHCH(CH_3)CH_2$— | $CH_3C\equiv CCH_2CH_2$— |
| $CH_2=CHCH_2CH_2CH_2$— | $HC\equiv CCH(C_2H_5)$— |
| $CH_2=CHCH_2(CH_3)CH$— | $HC\equiv CCH_2CH_2CH_2CH_2$— |
| $CH_2=CHCH(C_2H_5)$— | $CH_3(CH_2)_4C\equiv CCH_2CH_2$— |
| $CH_3(CH_2)_2CH=CHCH_2$— | |
| $CH_3CH=CH(CH_2)_2CH_2$— | $ClC\equiv CCH(CH_3)$— |
| $CH_2=CH(CH_2)_3CH_2$— | $BrC\equiv CCH(CH_3)$— |

TABLE 4

| | |
|---|---|
| $ClC\equiv CCH_2$— | $CH_2(CH_3O)CH_2CH_2$— |
| $BrC\equiv CCH_2$— | $CH_3CH(CH_3O)CH_2$— |
| $ClC\equiv CCH_2CH_2$— | $CH_3CH_2CH(CH_3O)$— |
| $BrC\equiv CCH_2CH_2$— | $CH_3OCH_2CH(CH_3)$— |
| $ClC\equiv CCH(CH_3)CH_2$— | $CH_3(CH_2)_2OCH_2CH_2$— |
| $BrC\equiv CCH(CH_3)CH_2$— | $CH_3CH_2OCH(CH_3)CH_2$— |
| $ClC\equiv CCH_2CH(CH_3)$— | $CH_3CH_2OCH_2CH(CH_3)$— |
| $BrC\equiv CCH_2CH(CH_3)$— | $CH_3OCH(C_2H_5)CH_2$— |
| $ClC\equiv CCH_2CH_2CH_2$— | $CH_3OCH_2CH(C_2H_5)$— |
| $BrC\equiv CCH_2CH_2CH_2$— | $C_2H_5OCH_2CH_2CH_2$— |
| $ClC\equiv CCH(C_2H_5)$— | $CH_3OCH(CH_3)CH_2CH_2$— |
| $BrC\equiv CCH(C_2H_5)$— | $CH_3OCH_2CH(CH_3)CH_2$— |
| $CH_3(CH_2)_3OCH_2CH(CH_3)$— | $CH_3OCH_2CH_2CH(CH_3)$— |
| $CH_3(CH_2)_3OCH_2CH_2$— | $CH_3SCH_2(CH_2)_2CH_2$— |
| $(CH_3)_2CHOCH_2CH_2$— | $CH_3SCH_2$— |
| $(CH_3)_2(CH_3O)CCH_2CH_2$— | $CH_3CH_2SCH_2$— |
| $CH_3(CH_3O)CHCH_2CH_2$— | $CH_3CH_2CH_2SCH_2$— |
| $CH_3OCH_2CH_2$— | $(CH_3)_2CHSCH_2$— |
| $CH_3CH_2OCH_2$— | $CH_3SCH_2CH_2$— |
| $CH_3OCH_2$— | $CH_3SCH(CH_3)$— |
| $(CH_3)_2CHOCH_2$— | $CH_3CH_2SCH_2CH_2$— |
| $CH_3CH_2CH_2OCH_2$— | $CH_3CH_2SCH(CH_3)$— |
| $CH_3CH(OCH_3)$— | $CH_3SCH_2CH_2CH_2$— |
| $CH_3CH_2OCH_2CH_2$— | $CH_3S(CH_3)CHCH_2$— |
| $CH_3CH(OC_2H_5)$— | $CH_3SCH(CH_3CH_2)$— |

TABLE 5

| | |
|---|---|
| $CH_3SCH_2CH(CH_3)$— | 3-sec-butyloxycyclohexyl |
| $(CH_3)_2CHSCH_2CH_2$— | |
| $CH_3CH_2CH_2SCH_2CH_2$— | 3-tert-butyloxycyclohexyl |
| $CH_3SCH(CH_3)C(CH_3)H$— | |

TABLE 5-continued

| | |
|---|---|
| $CH_3SCH(C_2H_5)CH_2$— | 4-methoxycyclohexyl |
| $CH_3SCH_2CH(C_2H_5)$— | 4-ethoxycyclohexyl |
| $CH_3CH_2SCH(CH_3)CH_2$— | 4-propoxycyclohexyl |
| $CH_3CH_2SCH_2CH(CH_3)$— | 4-isopropoxycyclohexyl |
| $CH_3CH_2SCH_2CH_2CH_2$— | 4-butoxycyclohexyl |
| $CH_3SCH(CH_3)CH_2CH_2$— | 4-isobutyloxycyclohexyl |
| $CH_3SCH_2CH(CH_3)CH_2$— | 4-sec-butyloxycyclohexyl |
| $CH_3SCH_2CH_2CH(CH_3)$— | 4-tert-butyloxycyclohexyl |
| $(CH_3)_3CSCH_2CH_2$— | |
| $(CH_3)_2CHCH_2SCH_2CH_2$— | 2-methoxycyclopentyl |
| $CH_3CH_2CH(CH_3)SCH_2CH_2$— | 2-ethoxycyclopentyl |
| $(CH_3)_3CSCH_2CH_2CH_2$— | 2-propoxycyclopentyl |
| $(CH_3)_2CHCH_2SCH_2CH_2CH_2$— | 2-isopropoxycyclopentyl |
| $CH_3CH_2CH(CH_3)SCH_2CH_2CH_2$— | 2-butoxycyclopentyl |
| 3-methoxycyclohexyl | 2-isobutyloxycyclopentyl |
| 3-ethoxycyclohexyl | 2-sec-butyloxycyclopentyl |
| 3-propoxycyclohexyl | 2-tert-butyloxycyclopentyl |
| 3-isopropoxycyclohexyl | |
| 3-butoxycyclohexyl | cyclopropyl |
| 3-isobutyloxycyclohexyl | cyclobutyl |
| | cyclopentyl |

TABLE 6

| | |
|---|---|
| cyclohexyl | 3-(difluorobromomethoxy)-cyclohexyl |
| 2,3-dimethylcyclohexyl | 4-(difluorobromomethoxy)-cyclohexyl |
| 2-ethylcyclohexyl | 3-(difluorobromomethoxy)-cyclopentyl |
| 3,3,5,5-tetramethyl-cyclohexyl | 3-(2,2,2-trifluoroethoxy)-cyclohexyl |
| 3,4-dimethylcyclohexyl | 4-(2,2,2-trifluoroethoxy)-cyclohexyl |
| 3,5-dimethylcyclohexyl | 3-(2,2,2-trifluoroethoxy)-cyclopentyl |
| 4-ethylcyclohexyl | 3-(1,1,2,2,2-pentafluoro-ethoxy)cyclohexyl |
| 2-methylcyclohexyl | 4-(1,1,2,2,2-pentafluoro-ethoxy)cyclohexyl |
| 3-methylcyclohexyl | 3-(1,1,2,2,2-pentafluoro-ethoxy)cyclopentyl |
| 4-methylcyclohexyl | 3-(2-chloroethoxy)-cyclohexyl |
| 3-methylcyclopentyl | 3-(2-chloroethoxy)-cyclopentyl |
| 2-methylcyclopentyl | 4-(2-chloroethoxy)-cyclohexyl |
| 3-(trifluoromethoxy)-cyclohexyl | 3-(2-bromoethoxy)-cyclohexyl |
| 4-(trifluoromethoxy)-cyclohexyl | |
| 3-(trifluoromethoxy)-cyclopentyl | |
| 3-(difluoromethoxy)-cyclohexyl | |
| 4-(difluoromethoxy)-cyclohexyl | |
| 3-(difluoromethoxy)-cyclopentyl | |

TABLE 7

| | |
|---|---|
| 3-(2-bromoethoxy)-cyclopentyl | 3-(1,2,2,3,3,3-hexa-fluoropropoxy)cyclopentyl |
| 4-(2-bromoethoxy)-cyclohexyl | 4-(1,2,2,3,3,3-hexa-fluoropropoxy)cyclohexyl |
| 3-(2-chloro-1,1,2-tri-fluoroethoxy)cyclohexyl | 2-cyclohexylethyl |
| | cyclobutylmethyl |
| 3-(2-chloro-1,1,2-tri-fluoroethoxy)cyclopentyl | cyclopropylmethyl |

TABLE 7-continued

| | |
|---|---|
| 4-(2-chloro-1,1,2-trifluoroethoxy)cyclohexyl | 1-cyclopropylethyl |
| | cyclohexylmethyl |
| 3-(2-bromo-1,1,2-trifluoroethoxy)cyclohexyl | cyclopentylmethyl |
| 3-(2-bromo-1,1,2-trifluoroethoxy)cyclopentyl | 2-methylcyclopropanemethyl |
| 4-(2-bromo-1,1,2-trifluoroethoxy)cyclohexyl | 3-cyclopentylpropyl |
| | 3-cyclohexylpropyl |
| 3-(1,1,2,2-tetrafluoroethoxy)cyclohexyl | 2-(2-methylcyclopropyl)ethyl |
| 3-(1,1,2,2-tetrafluoroethoxy)cyclopentyl | 2-cyclohexenyl |
| 4-(1,1,2,2-tetrafluoroethoxy)cyclohexyl | 3,5,5-trimethyl-2-cyclohexenyl |
| 3-(1,2,2,3,3,3-hexafluoropropoxy)cyclohexyl | 3-methyl-2-cyclohexenyl |
| | 2-(3-cyclohexenyl)ethyl |
| | (3-cyclohexenyl)methyl |
| | (1-cyclopentenyl)methyl |
| | 2-cyclopentenyl |
| | 3-cyclopentenyl |
| | 3-cyclohexenyl |

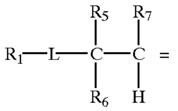

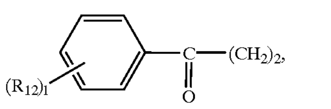

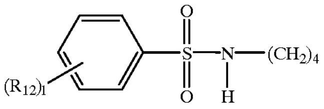

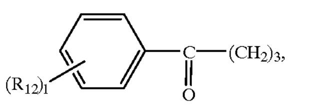

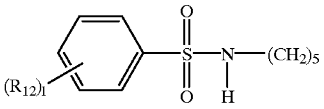

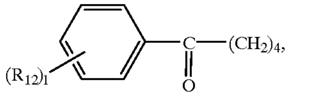

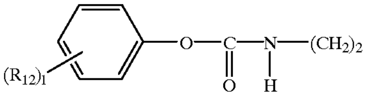

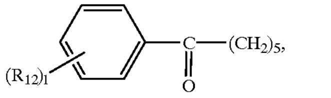

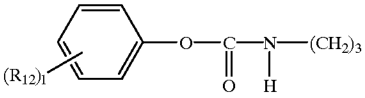

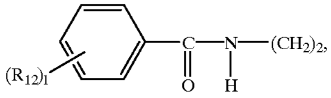

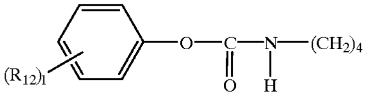

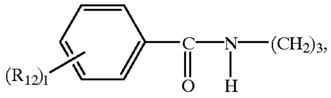

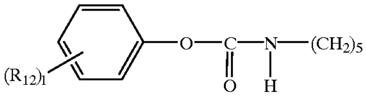

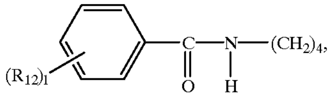

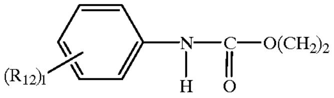

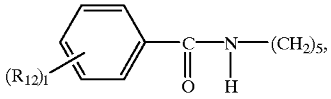

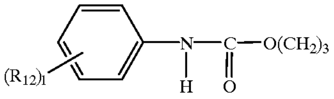

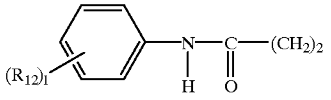

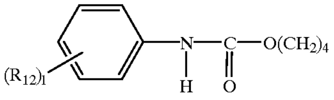

-continued

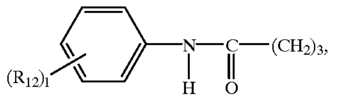
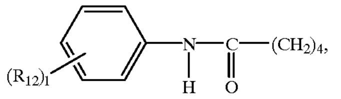
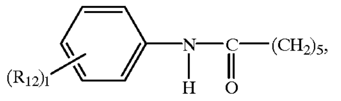
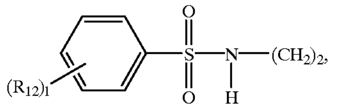
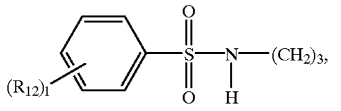
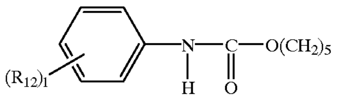
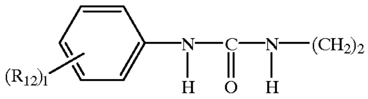
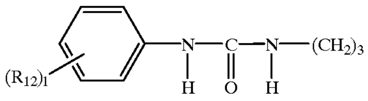
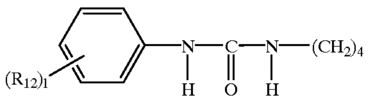
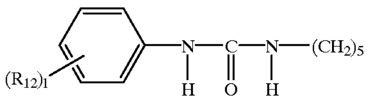

(in which $(R_{12})_l$ is as defined in Tables 8 to 21).

TABLE 8

| $(R_{12})_l$ | $(R_{12})_l$ |
|---|---|
| H | $3-OCH_2C_6H_5$ |
| $2-CH_3$ | $3-OCF_3$ |
| 2-F | $3-OCF_2CF_2H$ |
| $2-CF_3$ | $3-NO_2$ |
| 2-Cl | $3-OC_6H_4$ (p-$CH_3$) |
| 2-Br | $3-OC_6H_4$ (p-$C(CH_3)_3$) |
| 2-I | $3-OC_6H_4$ (m-$CF_3$) |
| $2-OCH_3$ | $3-OC_6H_4$ (p-Cl) |
| $2-OCH_2CH_3$ | $3-OC_6H_3$ (3,4-$Cl_2$) |
| $2-C_6H_5$ | $3-OC_6H_3$ (3,5-$Cl_2$) |
| $2-NO_2$ | $3-OC_6H_4$ (p-$OCH_3$) |
| $2-C_6H_4$ (p-$CF_3$) | 3-CN |
| $2-CH_2C_6H_5$ | $3-CH_3$ |
| $2-OC_6H_5$ | $3-CH_2CH_3$ |
| 2-CN | $3-CH_2CH_2CH_3$ |
| $3-CH_3$ | $3-CH(CH_3)_2$ |
| 3-F | $3-C(CH_3)_3$ |
| $3-CF_3$ | $3-OCF_2Br$ |
| 3-Cl | $3-OCF_2H$ |
| 3-Br | $3-OCF_2CFHCF_3$ |
| 3-I | $3-OCH_2CF_2$ |
| $3-OCH_3$ | $3-OCH_2CH_3$ |
| $3-OC_6H_5$ | $3-OCH_2CH_2CH_3$ |

TABLE 9

| |
|---|
| $3-OCH_2(CH_2)_2CH_3$ |
| $3-OCH(CH_3)_2$ |
| $3-OCH(CH_3)CH_2CH_3$ |
| $3-OCH_2CH(CH_3)CH_3$ |
| $3-OC(CH_3)_3$ |
| $3-OCH_2CH{=}CH_2$ |
| $3-OCH_2CH{=}C(Cl)_2^-$ |
| $3-OCH_2CH{=}C(Br)_2$ |
| $3-OCH_2CH{=}CH(Cl)$ |
| $3-OCH_2C(Cl){=}CH(Cl)$ |
| $3-OCH_2CH{=}(CH_3)_2$ |
| $3-OCH_2CH{=}CH(CH_3)$ |
| $3-OCH_2C(CH_3){=}CH_2$ |
| $3-OCH_2CBr{=}CH(Br)$ |
| $3-CH_2OH$ |
| $3-CH_2OCH_3$ |
| $3-CH_2OCH_2CH_3$ |
| $3-CH_2OCH_2CH_2CH_3$ |
| $3-CH_2OCH(CH_3)_2$ |
| $3-OCH_2C{\equiv}CH$ |
| $3-OCH_2C{\equiv}C{-}Cl$ |
| $3-OCH_2C{\equiv}C{-}Br$ |
| $3-OCH_2C{\equiv}C{-}CH_3$ |
| $3-OCH(CH_3)C{\equiv}CH$ |
| 3-cyclopentyl |
| 3-cyclohexyl |
| 3-(3-cyclopentenyl) |
| 3-(4-cyclopentenyl) |
| 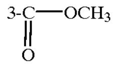 |
| 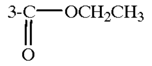 |
| 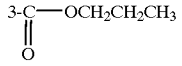 |
| 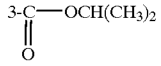 |
| 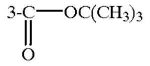 |
| 3-cyclopropyloxy |
| 3-cyclobutyloxy |
| 3-cyclopentyloxy |
| 3-cyclohexyloxy |
| 3-(3-cyclohexenyl) |
| 3-(4-cyclohexenyl) |
| 3-(5-cyclohexenyl) |
| 3-(3-cyclopentenyloxy) |
| 3-(4-cyclopentenyloxy) |

TABLE 10

| | |
|---|---|
| 3-(3-cyclohexenyloxy) | 3-$OCH_2C_6H_4$ (m-$CH_3$) |
| 3-(4-cyclohexenyloxy) | 3-$OCH_2C_6H_4$ (m-$CF_3$) |
| 3-(5-cyclohexenyloxy) | 3-$SCF_2CF_2H$ |
| 3-$CH_2C_6H_5$ | 3-$SCH_3$ |
| 3-$OCH_2CH{=}C(Cl)(CH_3)$ | 3-$SCH_2CH_3$ |
| 3-$OCH_2CH{=}C(CH_3)(CF_3)$ | 3-$OCH_2C(Cl){=}CH_2$ |
| 3-$OC_6H_4$ (o-Cl) | 4-$CH_3$ |
| 3-$OC_6H_4$ (o-F) | 4-$CH_2CH_3$ |
| 3-$OC_6H_4$ (o-$CH_3$) | 4-$CH(CH_3)_2$ |
| 3-$OC_6H_4$ (m-Cl) | 4-$C(CH_3)_3$ |
| 3-$OC_6H_4$ (m-F) | 4-$CH_2(CH_2)_2CH_3$ |
| 3-$OC_6H_4$ (m-$CH_3$) | 4-F |
| 3-$OCH_2C_6H_4$ (o-Cl) | 4-$CF_3$ |
| 3-$OCH_2C_6H_4$ (o-F) | 4-Cl |
| 3-$OCH_2C_6H_4$ (o-Br) | 4-Br |
| 3-$OCH_2C_6H_4$ (o-$CH_3$) | 4-$OCH_3$ |
| 3-$OCH_2C_6H_4$ (o-$CF_3$) | 4-$OCH_2CH_3$ |
| 3-$OCH_2C_6H_4$ (m-Cl) | 4-$OCH_2(CH_2)_2CH_3$ |
| 3-$OCH_2C_6H_4$ (m-F) | 4-$OCF_3$ |
| 3-$OCH_2C_6H_4$ (m-Br) | 4-$C_6H_5$ |
| 3-$OCH_2C_6H_4$ (m-$CH_3$) | 4-$OCH_2C_6H_5$ |
| 3-$OCH_2C_6H_4$ (m-$CF_3$) | 4-$OCH_2CH_2CH_3$ |
| 3-$OCH_2C_6H_4$ (p-Cl) | 4-$OCF_3$ |
| 3-$OCH_2C_6H_4$ (p-Br) | 4-$SCH_3$ |
| 3-$OCH_2C_6H_4$ (p-F) | 4-$NO_2$ |

TABLE 11

| | |
|---|---|
| 4-$OC_6H_5$ | 4-$OCH_2CH{=}CH(Cl)$ |
| 4-$CH_2(CH_2)_3CH_3$ | 4-$OCH_2C(Cl){=}CH(Cl)$ |
| 4-$CH_2(CH_2)_4CH_3$ | 4-$OCH_2CH{=}C(CH_3)_2$ |
| 4-$CH_2(CH_2)_5CH_3$ | 4-$OCH_2CH{=}CH(CH_3)$ |
| 4-$CH_2(CH_2)_6CH_3$ | 4-$OCH_2C(CH_3){=}CH_2$ |
| 4-$CH{=}CH_2$ | 4-$OCH_2C(Cl){=}CH_2$ |
| 4-I | 4-$OCH_2C(Br){=}CH_2(Br)$ |
| 4-$OCH_2(CH_2)_3CH_3$ | 4-$CH_2OH$ |
| 4-$OCH_2(CH_2)_4CH_3$ | 4-$CH_2OCH_3$ |
| 4-$OCH_2(CH_2)_5CH_3$ | 4-$CH_2OCH_2CH_3$ |
| 4-$OCH(CH_3)_2$ | 4-$CH_2OCH_2CH_2CH_3$ |
| 4-(2-cyclohexenyl) | 4-$CH_2OCH(CH_3)_2$ |
| 4-$SCH_2CH_3$ | 4-$OCH_2C{\equiv}CH$ |
| 4-$C_6H_4$(p-$CH_2CH_3$) | 4-$OCH_2C{\equiv}C{-}Cl$ |
| 4-CN | 4-$OCH_2C{\equiv}C{-}Br$ |
| 4-$OCF_2Br$ | 4-$OCH_2C{\equiv}C{-}CH_3$ |
| 4-$OCF_2H$ | 4-$OCH(CH_3)C{\equiv}CH$ |
| 4-$OCF_2CFHCF_3$ | 4-cyclopentyl |
| 4-$OCH_2CF_3$ | 4-cyclohexyl |
| 4-$OCF_2CF_2H$ | 4-(3-cyclopentenyl) |
| 4-$SCF_2CF_2H$ | 4-(4-cyclopentenyl) |
| 4-$SCH(CH_3)_2$ | 4-$\overset{\overset{O}{\|}}{C}OCH_3$ |
| 4-$OCH_2CH{=}CH_2$ | |
| 4-$OCH_2CH{=}C(Cl)_2$ | |
| 4-$OCH_2CH{=}C(Br)_2$ | |

TABLE 12

| |
|---|
| 4-$\overset{\overset{O}{\|}}{C}OCH_2CH_3$ |
| 4-$\overset{\overset{O}{\|}}{C}OCH_2CH_2CH_3$ |
| 4-$\overset{\overset{O}{\|}}{C}OCH(CH_3)_2$ |
| 4-$\overset{\overset{O}{\|}}{C}OC(CH_3)_3$ |
| 4-cyclopropyloxy |

TABLE 12-continued

| |
|---|
| 4-cyclobutyloxy |
| 4-cyclopentyloxy |
| 4-cyclohexyloxy |
| 4-(3-cyclohexenyl) |
| 4-(4-cyclohexenyl) |
| 4-(5-cyclohexenyl) |
| 4-(3-cyclopentenyloxy) |
| 4-(4-cyclopentenyloxy) |
| 4-(3-cyclohexenyloxy) |
| 4-(4-cyclohexenyloxy) |
| 4-(4-cyclohexenyloxy) |
| 4-(5-cyclohexenyloxy) |
| 4-$CH_2C_6H_5$ |
| 4-$OCH_2CH{=}C(Cl)CH_3$ |
| 4-$OCH_2CH{=}C(CH_3)CF_3$ |
| 4-$OC_6H_4$(o-Cl) |
| 4-$OC_6H_4$(o-F) |
| 4-$OC_6H_4$(o-$CH_3$) |
| 4-$OC_6H_4$(m-Cl) |
| 4-$OC_6H_4$(m-F) |
| 4-$OC_6H_4$(m-$CH_3$) |
| 4-$OCH_2C_6H_4$(o-Cl) |
| 4-$OCH_2C_6H_4$(o-F) |
| 4-$OCH_2C_6H_4$(o-Br) |
| 4-$OCH_2C_6H_4$(o-$CH_3$) |
| 4-$OCH_2C_6H_4$(o-$CF_3$) |
| 4-$OCH_2C_6H_4$(m-Cl) |
| 4-$OCH_2C_6H_4$(m-F) |
| 4-$OCH_2C_6H_4$(m-Br) |
| 4-$OCH_2C_6H_4$(m-$CH_3$) |
| 4-$OCH_2C_6H_4$(m-$CF_3$) |
| 4-$OCH_2C_6H_4$(p-Cl) |
| 4-$OCH_2C_6H_4$(p-Br) |
| 4-$OCH_2C_6H_4$(p-F) |
| 4-$OCH_2C_6H_4$(p-$CH_3$) |
| 4-$OCH_2C_6H_4$(p-$CF_3$) |
| 4-$SCF_2CF_2H$ |
| 4-$OCH_2C(Cl){=}CH_2$ |

TABLE 13

| | |
|---|---|
| 2,6-$F_2$ | 3-$CH_3$, 4-$NO_2$ |
| 2,3-$F_2$ | 3-$NO_2$, 4-$CH_3$ |
| 2-F, 6-Cl | 2-$NO_2$, 4-Cl |
| 2,6-$Cl_2$ | 3-$NO_2$, 4-Cl |
| 2,3-$(OCH_3)_2$ | 2-Cl, 5-$NO_2$ |
| 2,4-$(CH_3)_2$ | 2-$NO_2$, 5-Cl |
| 2,4-$(CH_3)_2$ | 3-$OCH_3$, 4-$NO_2$ |
| 2,5-$(CH_3)_2$ | 2-$CH_3$, 3-F |
| 3,4-$F_2$ | 2-F, 3-$CF_3$ |
| 2,4-$F_2$ | 2,3-$Cl_2$ |
| 2,5-$F_2$ | 2,6-$(OCH_3)_2$ |
| 2,4-$Cl_2$ | 2-Cl, 6-$NO_2$ |
| 3,4-$Cl_2$ | 2-$NO_2$, 3-$OCH_3$ |
| 2,5-$Cl_2$ | 2,6-$(NO_2)_2$ |
| 2,4-$(OCH_3)_2$ | 2-Cl, 5-$CF_3$ |
| 2,5-$(OCH_3)_2$ | 3-Cl, 4-F |
| 2-$OCH_3$, 5-Br | 2-Cl, 4-F |
| 3,4-$OCH_2O$— | 3-Br, 4-F |
| 3,5-$(CH_3)_2$ | 2-$OCH_3$, 5-Br |
| 3,5-$(CF_3)_2$ | 3,4-$OCH_2CH_2O$— |
| 3,5-$F_2$ | 3-$NO_2$, 5-Cl |
| 3,5-$Cl_2$ | 2,4-$(NO_2)_2$ |
| 3,5-$(OCH_3)_2$ | 3,5-$(OCH_2C_6H_5)_2$ |
| 2-$CH_3$, 4-$C_6H_5$ | 3,4-$(OCH_2C_6H_5)_2$ |
| 2-$NO_2$, 4-Cl | 2-F, 6-$CF_3$ |
| 2-$NO_2$, 5-$CH_3$ | 2-F, 3-$CF_3$ |

TABLE 14

| | |
|---|---|
| 2,6-$(CF_3)_2$ | 2-$CH_3$, 5-$NO_2$ |
| 2-$NO_2$, 6-$CH_3$ | 2-$NO_2$, 4-$CF_3$ |
| 2-$NO_2$, 3-$CH_3$ | 2-F, 5-$NO_2$ |
| 2-$CH_3$, 3-$NO_2$ | 2-Cl, 4-$NO_2$ |

TABLE 14-continued

| | |
|---|---|
| 2-NO$_2$, 3-Cl | 3-NO$_2$, 4-F |
| 2-Cl, 3-NO$_2$ | 2-Br, 5-NO$_2$ |
| 2-Br, 3-NO$_2$ | 3-NO$_2$, 4-OCH$_3$ |
| 2-NO$_2$, 3-OCH$_3$ | 3,5-(C(CH$_3$)$_3$)$_2$ |
| 2-CH$_3$, 5-F | 2,3-(CH$_3$)$_2$, 4-OCH$_3$ |
| 3-F, 4-CH$_3$ | 3-CH$_3$, 2,4-(OCH$_3$)$_2$ |
| 3-Br, 4-CH$_3$ | 2,3,4-(OCH$_3$)$_2$ |
| 2,4-(CF$_3$)$_2$ | 3,4,5-(OCH$_3$)$_3$ |
| 3-I, 4-CH$_3$ | 2,3,4,5,6-F$_5$ |
| 2-Cl, 5-CF$_3$ | 2,4,6-(CH$_3$)$_3$ |
| 2,5-(CF$_3$)$_2$ | 2,3,5-Cl$_3$ |
| 2-F, 4-CF$_3$ | 3,4-(OCH$_3$)$_2$, 5-Br |
| 2-Cl, 4-F | 2,4,6-(OCH$_3$)$_3$ |
| 3-OCH$_3$, 4-CH$_3$ | 2,4-(OCH$_3$)$_2$, 5-Br |
| 2-OCH$_3$, 4-Cl | 2-Br, 4,5-(OCH$_3$)$_2$ |
| 2-OCH$_3$, 5-Cl | 2,4,5-(OCH$_3$)$_3$ |
| 2-Br, 5-OCH$_3$ | 2-NO$_2$, 3,4-(OCH$_3$)$_2$ |
| 3,4-(OCH$_2$CH$_3$)$_2$ | 2-NO$_2$, 3,4-OCH$_2$O— |
| 2-Cl, 5-SCH$_3$ | 2,5-Cl$_2$, 4-CHF$_2$ |
| 2-OCH$_3$, 4-SCH$_3$ | 2,3,4-F$_3$ |
| 3-CH$_3$, 4-NO$_2$ | 2,3,6-Cl$_3$ |

TABLE 15

| | |
|---|---|
| 2,3,5,6-F$_4$ | 3-Cl, 4-OCH$_2$CF$_3$ |
| 2,3,6-F$_3$ | 3-Cl, 4-OC$_6$H$_5$ |
| 2,4,6-F$_3$ | 3-Cl, 4-OCH$_2$C$_6$H$_5$ |
| 3,4,5-F$_3$ | 3-Cl, 4-cyclopentyloxy |
| 2,4,6-Cl$_3$ | 3-Cl, 4-cyclohexyloxy |
| 2,3,5-Cl$_3$ | 3-Br, 4-OCH$_3$ |
| 2,3,5-I$_3$ | 3-Br, 4-OCH$_2$CH$_3$ |
| 2,4,5-F$_3$ | 3-Br, 4-OCH$_2$CH$_2$CH$_3$ |
| 2,4-Cl$_2$, 5-F | 3-Br, 4-OCH(CH$_3$)$_2$ |
| 2,3,4,5-F$_4$ | 3-Br, 4-OCH$_2$(CH$_2$)$_2$CH$_3$ |
| 2,3,5,6-F$_4$, 4-CH$_3$ | 3-Br, 4-OCH(CH$_3$)CH$_2$CH$_3$ |
| 2,3,5,6-F$_4$, 4-Br | 3-Br, 4-OCH$_2$CH(CH$_3$)$_2$ |
| 3-Cl, 4-OCH$_3$ | 3-Br, 4-OC(CH$_3$)$_3$ |
| 3-Cl, 4-OCH$_2$CH$_3$ | 3-Br, 4-OCF$_3$ |
| 3-Cl, 4-OCH$_2$CH$_2$CH$_3$ | 3-Br, 4-OCF$_2$Br |
| 3-Cl, 4-OCH(CH$_3$)$_2$ | 3-Br, 4-OCF$_2$H |
| 3-Cl, 4-OCH$_2$(CH$_2$)$_2$CH$_3$ | 3-Br, 4-OCF$_2$CF$_2$H |
| 3-Cl, 4-OCH(CH$_3$)CH$_2$CH$_3$ | 3-Br, 4-OCF$_2$CFHCF$_3$ |
| 3-Cl, 4-OCH$_2$CH(CH$_3$)$_2$ | 3-Br, 4-OCH$_2$CF$_3$ |
| 3-Cl, 4-OC(CH$_3$)$_3$ | 3-Br, 4-OC$_6$H$_5$ |
| 3-Cl, 4-OCF$_3$ | 3-Br, 4-OCH$_2$C$_6$H$_5$ |
| 3-Cl, 4-OCF$_2$Br | 3-Br, 4-cyclopentyloxy |
| 3-Cl, 4-OCF$_2$H | 3-Br, 4-cyclohexyloxy |
| 3-Cl, 4-OCF$_2$CF$_2$H. | 3-F, 4-OCH$_3$ |
| 3-Cl, 4-OCF$_2$CFHCF$_3$ | 3-F, 4-OCH$_2$CH$_3$ |

TABLE 16

| | |
|---|---|
| 3-F, 4-OCH$_2$CH$_2$CH$_3$ | 3-CH$_3$, 4-OCF$_3$ |
| 3-F, 4-OCH(CH$_3$)$_2$ | 3-CH$_3$, 4-OCF$_2$Br |
| 3-F, 4-OCH$_2$(CH$_2$)$_2$CH$_3$ | 3-CH$_3$, 4-OCF$_2$H |
| 3-F, 4-OCH(CH$_3$)CH$_2$CH$_3$ | 3-CH$_3$, 4-OCF$_2$CF$_2$H |
| 3-F, 4-OCH$_2$CH(CH$_3$)$_2$ | 3-CH$_3$, 4-OCF$_2$CFHCF$_3$ |
| 3-F, 4-OC(CH$_3$)$_3$ | 3-CH$_3$, 4-OCH$_2$CF$_3$ |
| 3-F, 4-OCF$_3$ | 3-CH$_3$, 4-OC$_6$H$_5$ |
| 3-F, 4-OCF$_2$Br | 3-CH$_3$, 4-OCH$_2$C$_6$H$_5$ |
| 3-F, 4-OCF$_2$H | 3-CH$_3$, 4-cyclopentyloxy |
| 3-F, 4-OCF$_2$CF$_2$H | 3-CH$_3$, 4-cyclohexyloxy |
| 3-F, 4-OCF$_2$CFHCF$_3$ | 3-OCH$_3$, 4-OCH$_3$ |
| 3-F, 4-OCH$_2$CF$_3$ | 3-OCH$_3$, 4-OCH$_2$CH$_3$ |
| 3-F, 4-OC$_6$H$_5$ | 3-OCH$_3$, 4-OCH$_2$CH$_2$CH$_3$ |
| 3-F, 4-OCH$_2$C$_6$H$_5$ | 3-OCH$_3$, 4-OCH(CH$_3$)$_2$ |
| 3-F, 4-cyclopentyloxy | 3-OCH$_3$, 4-OCH$_2$(CH$_2$)$_2$CH$_3$ |
| 3-F, 4-cyclohexyloxy | 3-OCH$_3$, 4-OCH(CH$_3$)CH$_2$CH$_3$ |
| 3-CH$_3$, 4-OCH$_3$ | 3-OCH$_3$, 4-OCH$_2$CH(CH$_3$)$_2$ |
| 3-CH$_3$, 4-OCH$_2$CH$_3$ | 3-OCH$_3$, 4-OC(CH$_3$)$_3$ |
| 3-CH$_3$, 4-OCH$_2$CH$_2$CH$_3$ | 3-OCH$_3$, 4-OCF$_3$ |
| 3-CH$_3$, 4-OCH(CH$_3$)$_2$ | 3-OCH$_3$, 4-OCF$_2$Br |
| 3-CH$_3$, 4-OCH$_2$(CH$_2$)$_2$CH$_3$ | 3-OCH$_3$, 4-OCF$_2$H |
| 3-CH$_3$, 4-OCH(CH$_3$)CH$_2$CH$_3$ | 3-OCH$_3$, 4-OCF$_2$CF$_2$H |

TABLE 16-continued

| | |
|---|---|
| 3-CH$_3$, 4-OCH$_2$CH(CH$_3$)$_2$ | 3-OCH$_3$, 4-OCF$_2$CFHCF$_3$ |
| 3-CH$_3$, 4-OC(CH$_3$)$_3$ | 3-OCH$_3$, 4-OCH$_2$CF$_3$ |

TABLE 17

| | |
|---|---|
| 3-OCH$_3$, 4-OC$_6$H$_5$ | 4-Cl, 3-OCH$_3$ |
| 3-OCH$_3$, 4-OCH$_2$C$_6$H$_5$ | 4-Cl, 3-OCH$_2$CH$_3$ |
| 3-OCH$_3$, 4-cyclopentyloxy | 4-Cl, 3-OCH$_2$CH$_2$CH$_3$ |
| 3-OCH$_3$, 4-cyclopentyloxy | 4-Cl, 3-OCH(CH$_3$)$_2$ |
| 3-OCH$_2$OCH$_3$, 4-OCH$_3$ | 4-Cl, 3-OCH$_2$(CH$_2$)$_2$CH$_3$ |
| 3-OCH$_2$OCH$_3$, 4-OCH$_2$CH$_3$ | 4-Cl, 3-OCH(CH$_3$)CH$_2$CH$_3$ |
| 3-OCH$_2$OCH$_3$, 4-OCH$_2$CH$_2$CH$_3$ | 4-Cl, 3-OCH$_2$CH(CH$_3$)$_2$ |
| 3-OCH$_2$OCH$_3$, 4-OCH(CH$_3$)$_2$ | 4-Cl, 3-OC(CH$_3$)$_3$ |
| 3-OCH$_2$OCH$_3$, 4-OCH$_2$(CH$_2$)$_2$CH$_3$ | 4-Cl, 3-OCF$_3$ |
| 3-OCH$_2$OCH$_3$, 4-OCH(CH$_3$)CH$_2$CH$_3$ | 4-Cl, 3-OCF$_2$Br |
| 3-OCH$_2$OCH$_3$, 4-OCH$_2$CH(CH$_3$)$_2$ | 4-Cl, 3-OCF$_2$H |
| 3-OCH$_2$OCH$_3$, 4-OC(CH$_3$)$_3$ | 4-Cl, 3-OCF$_2$CF$_2$H |
| 3-OCH$_2$OCH$_3$, 4-OCF$_3$ | 4-Cl, 3-OCF$_2$CFHCF$_3$ |
| 3-OCH$_2$OCH$_3$, 4-OCF$_2$Br | 4-Cl, 3-OCH$_2$CF$_3$ |
| 3-OCH$_2$OCH$_3$, 4-OCF$_2$H | 4-Cl, 3-OC$_6$H$_5$ |
| 3-OCH$_2$OCH$_3$, 4-OCF$_2$CF$_2$H | 4-Cl, 3-OCH$_2$C$_6$H$_5$ |
| 3-OCH$_2$OCH$_3$, 4-OCF$_2$CFHCF$_3$ | 4-Cl, 3-cyclopentyloxy |
| 3-OCH$_2$OCH$_3$, 4-OCH$_2$CF$_3$ | 4-Cl, 3-cyclohexyloxy |
| 3-OCH$_2$OCH$_3$, 4-OC$_6$H$_5$ | 4-Br, 3-OCH$_3$ |
| 3-OCH$_2$OCH$_3$, 4-OCH$_2$C$_6$H$_5$ | 4-Br, 3-OCH$_2$CH$_3$ |
| 3-OCH$_2$OCH$_3$, 4-cyclohexyloxy | 4-Br, 3-OCH$_2$CH$_2$CH$_3$ |
| 3-OCH$_2$OCH$_3$, 4-cyclopentyloxy | 4-Br, 3-OCH(CH$_3$)$_2$ |
| | 4-Br, 3-OCH$_2$(CH$_2$)$_2$CH$_3$ |
| | 4-Br, 3-OCH(CH$_3$)CH$_2$CH$_3$ |
| | 4-Br, 3-OCH$_2$CH(CH$_3$)$_2$ |
| | 4-Br, 3-OC(CH$_3$)$_3$ |

TABLE 18

| | |
|---|---|
| 4-Br, 3-OCF$_3$ | 4-F, 4-OCH$_2$C$_6$H$_5$ |
| 4-Br, 3-OCF$_2$Br | 4-F, 3-cyclopentyloxy |
| 4-Br, 3-OCF$_2$H | 4-F, 3-cyclohexyloxy |
| 4-Br, 3-OCF$_2$CF$_2$H | 4-CH$_3$, 3-OCH$_3$ |
| 4-Br, 3-OCF$_2$CFHCF$_3$ | 4-CH$_3$, 3-OCH$_2$CH$_3$ |
| 4-Br, 3-OCH$_2$CF$_3$ | 4-CH$_3$, 3-OCH$_2$CH$_2$CH$_3$ |
| 4-Br, 3-OC$_6$H$_5$ | 4-CH$_3$, 3-OCH(CH$_3$)$_2$ |
| 4-Br, 3-OCH$_2$C$_6$H$_5$ | 4-CH$_3$, 3-OCH$_2$(CH$_2$)$_2$CH$_3$ |
| 4-Br, 3-cyclopentyloxy | 4-CH$_3$, 3-OCH(CH$_3$)CH$_2$CH$_3$ |
| 4-Br, 3-cyclohexyloxy | 4-CH$_3$, 3-OCH$_2$CH(CH$_3$)$_2$ |
| 4-F, 3-OCH$_3$ | 4-CH$_3$, 3-OC(CH$_3$)$_3$ |
| 4-F, 3-OCH$_2$CH$_3$ | 4-CH$_3$, 3-OCF$_3$ |
| 4-F, 3-OCH$_2$CH$_2$CH$_3$ | 4-CH$_3$, 3-OCF$_2$Br |
| 4-F, 3-OCH(CH$_3$)$_2$ | 4-CH$_3$, 3-OCF$_2$H |
| 4-F, 3-OCH$_2$(CH$_2$)$_2$CH$_3$ | 4-CH$_3$, 3-OCF$_2$CF$_2$H |
| 4-F, 3-OCH(CH$_3$)CH$_2$CH$_3$ | 4-CH$_3$, 3-OCF$_2$CFHCF$_3$ |
| 4-F, 3-OCH$_2$CH(CH$_3$)$_2$ | 4-CH$_3$, 3-OCH$_2$CF$_3$ |
| 4-F, 3-OC(CH$_3$)$_3$ | 4-CH$_3$, 3-OC$_6$H$_5$ |
| 4-F, 3-OCF$_3$ | 4-CH$_3$, 3-OCH$_2$C$_6$H$_5$ |
| 4-F, 3-OCF$_2$Br | 4-CH$_3$, 3-cyclopentyloxy |
| 4-F, 3-OCF$_2$H | 4-CH$_3$, 3-cyclohexyloxy |
| 4-F, 3-OCF$_2$CF$_2$H | 2-Cl, 5-OCH$_3$ |
| 4-F, 3-OCF$_2$CFHCF$_3$ | 2-Cl, 5-OCH$_2$CH$_3$ |
| 4-F, 3-OCH$_2$CF$_3$ | 2-Cl, 5-OCH$_2$CH$_2$CH$_3$ |
| 4-F, 3-OC$_6$H$_5$ | 2-Cl, 5-OCH(CH$_3$)$_2$ |

TABLE 19

| | |
|---|---|
| 2-Cl, 5-OCH$_2$(CH$_2$)$_2$CH$_3$ | 2-Cl, 4-OCF$_2$CF$_2$H |
| 2-Cl, 5-OCH(CH$_3$)CH$_2$CH$_3$ | 2-Cl, 4-OCF$_2$CFHCF$_3$ |
| 2-Cl, 5-OCH$_2$CH(CH$_3$)$_2$ | 2-Cl, 4-OCH$_2$CF$_3$ |
| 2-Cl, 5-OC(CH$_3$)$_3$ | 2-Cl, 4-OC$_6$H$_5$ |
| 2-Cl, 5-OCF$_3$ | 2-Cl, 4-OCH$_2$C$_6$H$_5$ |
| 2-Cl, 5-OCF$_2$Br | 2-Cl, 4-cyclopentyloxy |
| 2-Cl, 5-OCF$_2$H | 2-Cl, 4-cyclohexyloxy |
| 2-Cl, 5-OCF$_2$CF$_2$H | 4-OCH$_3$, 3-OCH$_2$CH$_2$CH$_3$ |
| 2-Cl, 5-OCF$_2$CFHCF$_3$ | 4-OCH$_3$, 3-OCH(CH$_3$)$_2$ |
| 2-Cl, 5-OCH$_2$CF$_3$ | 4-OCH$_3$, 3-OCH$_2$(CH$_2$)$_2$CH$_3$ |

TABLE 19-continued

| | |
|---|---|
| 2-Cl, 5-$OC_6H_5$ | 4-$OCH_3$, 3-$OCH(CH_3)CH_2CH_3$ |
| 2-Cl, 5-$OCH_2C_6H_5$ | 4-$OCH_3$, 3-$OCH_2CH(CH_3)_2$ |
| 2-Cl, 5-cyclopentyloxy | 4-$OCH_3$, 3-$OC(CH_3)_3$ |
| 2-Cl, 5-cyclohexyloxy | 4-$OCH_3$, 3-$OCF_3$ |
| 2-Cl, 4-$OCH_3$ | 4-$OCH_3$, 3-$OCF_2Br$ |
| 2-Cl, 4-$OCH_2CH_3$ | 4-$OCH_3$, 3-$OCF_2H$ |
| 2-Cl, 4-$OCH_2CH_2CH_3$ | 4-$OCH_3$, 3-$OCF_2CF_2H$ |
| 2-Cl, 4-$OCH(CH_3)_2$ | 4-$OCH_3$, 3-$OCF_2CFHCF_3$ |
| 2-Cl, 4-$OCH_2(CH_2)_2CH_3$ | 4-$OCH_3$, 3-$OCH_2CF_3$ |
| 2-Cl, 4-$OCH(CH_3)CH_2CH_3$ | 4-$OCH_3$, 3-$OC_6H_5$ |
| 2-Cl, 4-$OCH_2CH(CH_3)_2$ | 4-$OCH_3$, 3-$OCH_2C_6H_5$ |
| 2-Cl, 4-$OC(CH_3)_3$ | 4-$OCH_3$, 3-cyclopentyloxy |
| 2-Cl, 4-$OCF_3$ | 4-$OCH_3$, 3-cyclohexyloxy |
| 2-Cl, 4-$OCF_2Br$ | 2,5-$(CH_3)_2$, 4-$OCH_3$ |
| 2-Cl, 4-$OCF_2H$ | 2,5-$(CH_3)_2$, 4-$OCH_2CH_3$ |

TABLE 20

| | |
|---|---|
| 2,5-$(CH_3)_2$, 4-$OCH_2CH_2CH_3$ | 3,5-$(CH_3)_2$, 4-$OCH_2(CH_2)_2CH_3$ |
| 2,5-$(CH_3)_2$, 4-$OCH(CH_3)_2$ | 3,5-$(CH_3)_2$, 4-$OCH(CH_3)CH_2CH_3$ |
| 2,5-$(CH_3)_2$, 4-$OCH_2(CH_2)_2CH_3$ | 3,5-$(CH_3)_2$, 4-$OCH_2CH(CH_3)_2$ |
| 2,5-$(CH_3)_2$, 4-$OCH(CH_3)CH_2CH_3$ | 3,5-$(CH_3)_2$, 4-$OC(CH_3)_3$ |
| 2,5-$(CH_3)_2$, 4-$OCH_2CH(CH_3)_2$ | 3,5-$(CH_3)_2$, 4-$OCF_3$ |
| 2,5-$(CH_3)_2$, 4-$OC(CH_3)_3$ | 3,5-$(CH_3)_2$, 4-$OCF_2Br$ |
| 2,5-$(CH_3)_2$, 4-$OCF_3$ | 3,5-$(CH_3)_2$, 4-$OCF_2H$ |
| 2,5-$(CH_3)_2$, 4-$OCF_2Br$ | 3,5-$(CH_3)_2$, 4-$OCF_2CF_2H$ |
| 2,5-$(CH_3)_2$, 4-$OCF_2H$ | 3,5-$(CH_3)_2$, 4-$OCF_2CFHCF_3$ |
| 2,5-$(CH_3)_2$, 4-$OCF_2CF_2H$ | 3,5-$(CH_3)_2$, 4-$OCH_2CF_3$ |
| 2,5-$(CH_3)_2$, 4-$OCF_2CFHCF_3$ | 3,5-$(CH_3)_2$, 4-$OC_6H_5$ |
| 2,5-$(CH_3)_2$, 4-$OCH_2CF_3$ | 3,5-$(CH_3)_2$, 4-$OCH_2C_6H_5$ |
| 2,5-$(CH_3)_2$, 4-$OC_6H_5$ | 3,5-$(CH_3)_2$, 4-cyclopentyloxy |
| 2,5-$(CH_3)_2$, 4-$OCH_2C_6H_5$ | 3,5-$(CH_3)_2$, 4-cyclohexyloxy |
| 2,5-$(CH_3)_2$, 4-cyclopentyloxy | 3,5-$Cl_2$, 4-$OCH_3$ |
| 2,5-$(CH_3)_2$, 4-cyclohexyloxy | 3-$OC_6H_4$ (p-F) |
| 3,5-$(CH_3)_2$, 4-$OCH_3$ | 3,5-$Cl_2$, 4-$OCH_2CH_3$ |
| 3,5-$(CH_3)_2$, 4-$OCH_2CH_3$ | 3,5-$Cl_2$, 4-$OCH_2CH_2CH_3$ |
| 3,5-$(CH_3)_2$, 4-$OCH_2CH_2CH_3$ | 3,5-$Cl_2$, 4-$OCH(CH_3)_2$ |
| 3,5-$(CH_3)_2$, 4-$OCH(CH_3)_2$ | 3,5-$Cl_2$, 4-$OCH_2(CH_2)_2CH_3$ |
| | 3,5-$Cl_2$, 4-$OCH(CH_3)CH_2CH_3$ |

TABLE 21

| | |
|---|---|
| 3,5-$Cl_2$, 4-$OCH_2CH(CH_3)_2$ | 3,5-$Cl_2$, 4-$OC_6H_5$ |
| 3,5-$Cl_2$, 4-$OC(CH_3)_3$ | 3,5-$Cl_2$, 4-$OCH_2C_6H_5$ |
| 3,5-$Cl_2$, 4-$OCF_3$ | 3,5-$Cl_2$, 4-cyclopentyloxy |
| 3,5-$Cl_2$, 4-$OCF_2Br$ | 3,5-$Cl_2$, 4-cyclohexyloxy |
| 3,5-$Cl_2$, 4-$OCF_2H$ | 2-F, 5-$OC_6H_4$ (p-F) |
| 3,5-$Cl_2$, 4-$OCF_2CF_2H$ | 2-Br, 5-$(OC_6H_5)$ |
| 3,5-$Cl_2$, 4-$OCF_2CFHCF_3$ | 4-$OC_6H_4$ (p-$CF_3$) |
| 3,5-$Cl_2$, 4-$OCH_2CF_3$ | 3-$OC_6H_4$ (p-F) |
| 3,4-$OCH_2CH_2O$—, 2-$CH_3$ | |

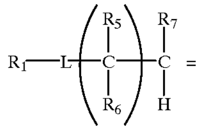

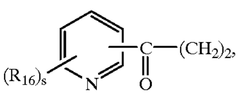
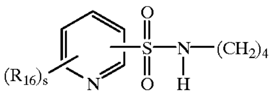

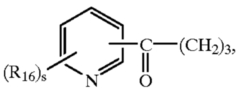
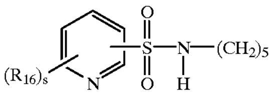

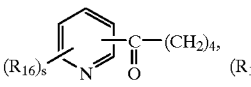
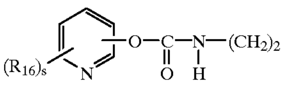

-continued

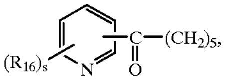
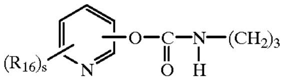

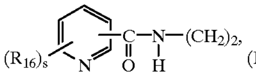
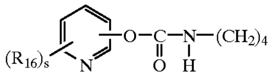

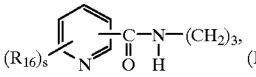
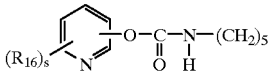

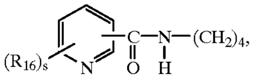
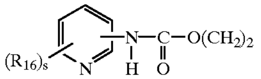

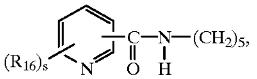
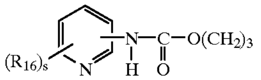

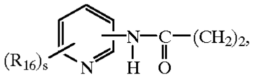
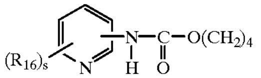

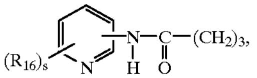
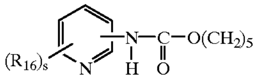

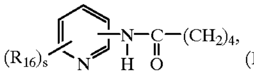
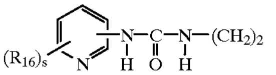

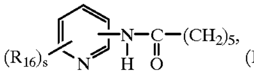
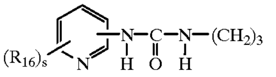

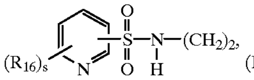
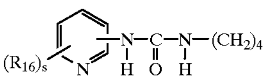

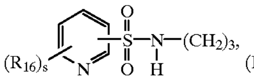
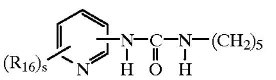

(in which the position of the heterocyclic ring and $(R_{16})_s$ are each as defind in Table 22).

TABLE 22

| Position of heterocyclic ring | $(R_{16})_s$ |
|---|---|
| 3 | H |
| 3 | 6-Cl |
| 3 | 6-Br |
| 3 | 6-I |
| 3 | 6-$CH_3$ |
| 3 | 6-$CF_3$ |
| 3 | 2-Cl, 6-$CH_3$ |
| 3 | 5,6-$Cl_2$ |
| 3 | 5-Br |
| 3 | 5,6-$(OCH_3)_2$ |
| 2 | H |
| 2 | 6-$CH_3$ |
| 2 | 6-Cl |
| 2 | 5-$CF_3$ |
| 2 | 5-Cl |
| 2 | 6-F |
| 2 | 5-Br |
| 2 | 3,5-$(CF_3)_2$ |
| 2 | 4,5-$(CF_3)_2$ |
| 2 | 3,5-$Cl_2$ |
| 2 | 3-Cl, 5-$CF_3$ |
| 4 | H |

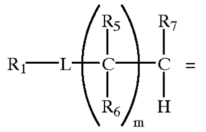

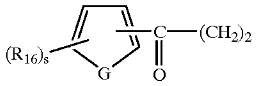

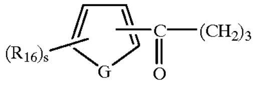

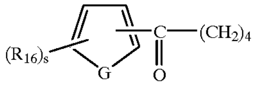

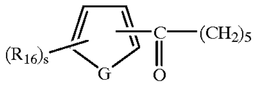

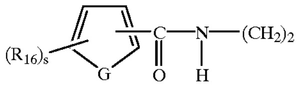

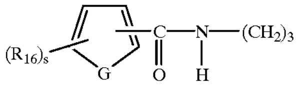

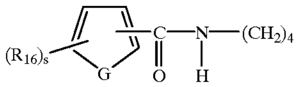

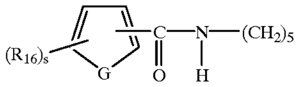

(in which G, the position of the heterocyclic ring and $(R_{16})_s$ are each as definid in Table 23and 24).

TABLE 23

| G | Position of heterocyclic ring | $(R_{16})_s$ |
|---|---|---|
| O | 2 | H |
| O | 2 | 5-$CH_3$ |
| O | 2 | 5-$CH_2OCH_3$ |
| O | 2 | 5-$CH_2CH_3$ |
| O | 2 | 5-$NO_2$ |
| O | 2 | 5-Cl |
| O | 2 | 5-Br |
| O | 3 | H |
| O | 3 | 2-$CH_3$ |
| O | 3 | 2,5-$(CH_3)_2$ |
| O | 3 | 2,4-$(CH_3)_2$ |
| S | 2 | H |
| S | 2 | 5-$CH_3$ |
| S | 2 | 5-Cl |
| S | 2 | 5-Br |
| S | 2 | 5-$NO_2$ |
| S | 2 | 5-$NHCOCH_3$ |
| S | 2 | 5-$NHCOCF_3$ |
| S | 2 | 3-$CH_3$ |
| S | 2 | 4-Br |
| S | 3 | H |
| S | 3 | 2,5-$(CH_3)_2$ |
| NH | 2 | H |

TABLE 24

| G | Position of heterocyclic ring | $(R_{16})_s$ |
|---|---|---|
| NH | 2 | 2,4-$(CH_3)_2$ |
| N | 2 | 1-$CH_3$ |
| NH | 2 | 3,5-$(CH_3)_2$ |
| NH | 2 | 3,4,5-$(CH_3)_3$ |
| NH | 2 | 3,4-$(C_2H_5)_2$, 5-$CH_3$ |
| NH | 3 | H |
| N | 3 | 1-$CH_3$ |
| NH | 3 | 5-Cl |
| N | 2 | 1,2,4-$(CH_3)_3$ |
| N | 2 | 1,3,5-$(CH_3)_3$ |
| N | 2 | 1,3,4,5-$(CH_3)_4$ |
| N | 2 | 3,4-$(C_2H_5)_2$, 1,5-$(CH_3)_2$ |
| N | 3 | 5-Cl, 1-$CH_3$ |

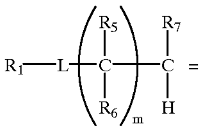

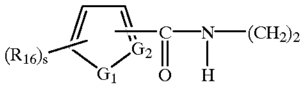

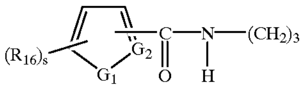

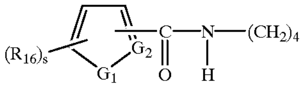

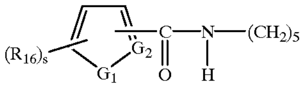

(in which $G_1$, $G_2$, the position of heterocyclic ring and $(R_{16})_s$ are each as defined in Table 25).

TABLE 25

| $G_1$ | $G_2$ | Position of heterocyclic ring | $(R_{16})_s$ |
|---|---|---|---|
| O | N | 3 | H |
| O | N | 3 | 5-Cl |
| O | N | 3 | 5-Br |
| O | N | 5 | H |
| S | N | 3 | H |
| S | N | 3 | 5-Cl |
| S | N | 3 | 5-Br |
| NH | N | 4 | H |
| NH | N | 4 | 3-$CF_3$ |
| N | N | 5 | 1-$C_2H_5$, 3-$CH_3$ |
| NH | N | 5 | 3-$CH_3$ |
| N | N | 4 | 1-$CH_3$ |
| N | N | 4 | 1-$CH_3$, 3-$CF_3$ |
| N | N | 5 | 1,3-$(CH_3)_2$ |
| N | N | 4 | 1-$CH_3$, 5-$NO_2$ |

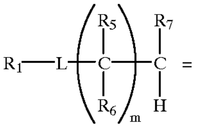
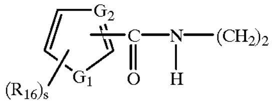
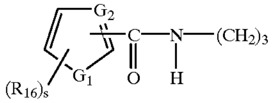
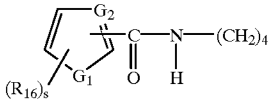
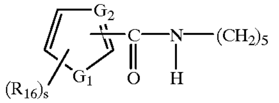
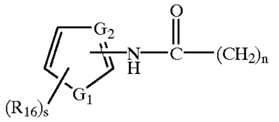
(n = 2, 3, 4 or 5)
(in which $G_1$, $G_2$, the position of heterocyclic ring and $(R_{16})_s$ are each as defined in Table 26).
TABLE 26
| $G_1$ | $G_2$ | Position of heterocyclic ring | $(R_{16})_s$ |
|---|---|---|---|
| S | N | 4 | H |
| S | N | 4 | 2-Cl |
| S | N | 4 | 2-Br |
| S | N | 5 | H |
| S | N | 5 | 2-Cl |
| S | N | 5 | 2-Br |
| S | N | 5 | 4-$CH_3$ |
| NH | N | 5 | 2,4-$(CH_3)_2$ |
| NH | N | 2 | H |
| NH | N | 5 | 3-$CH_3$ |
| N | N | 5 | 1-$C_2H_5$, 3-$CH_3$ |
| N | N | 2 | 1-$CH_3$ |
| N | N | 5 | 1,3-$(CH_3)_2$ |
| S | N | 2 | 5-Br |
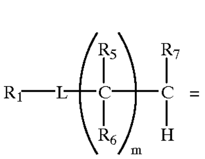
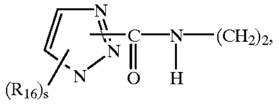
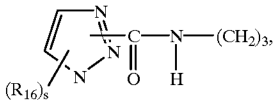
-continued
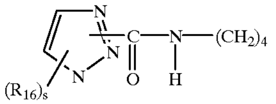
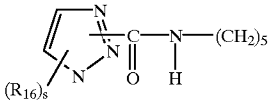
TABLE 27
| Position of heterocyclic ring | $(R_{16})_s$ |
|---|---|
| 3 | H |
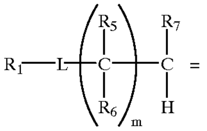
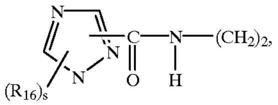
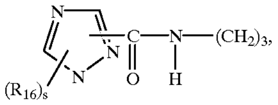
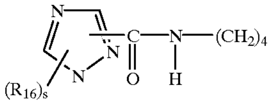
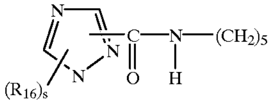
TABLE 28
| Position of heterocyclic ring | $(R_{16})_s$ |
|---|---|
| 3 | 1-H |
| 3 | 1-$C_6H_5$ |
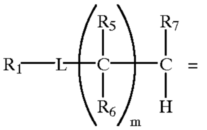
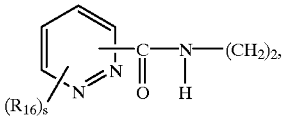
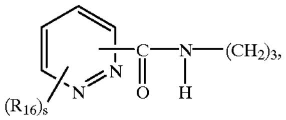

-continued
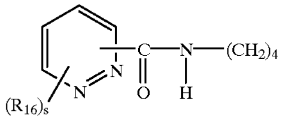
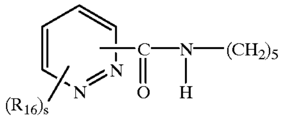
TABLE 29
| Position of heterocyclic ring | $(R_{16})_s$ |
|---|---|
| 3 | 6-Cl |
| 4 | H |
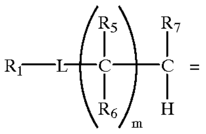
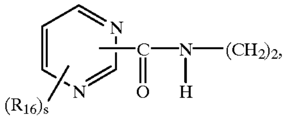
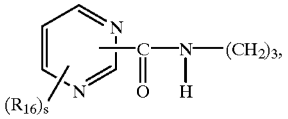
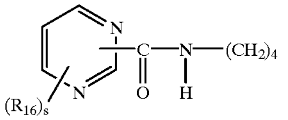
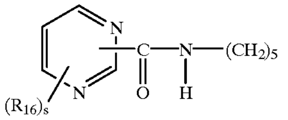
TABLE 30
| Position of heterocyclic ring | $(R_{16})_s$ |
|---|---|
| 2 | 5-Br |
| 5 | 2-Cl |
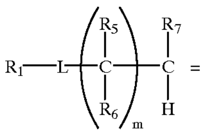
-continued
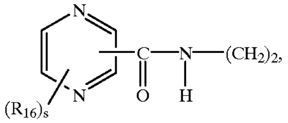
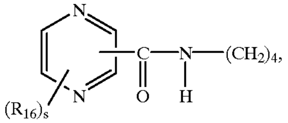
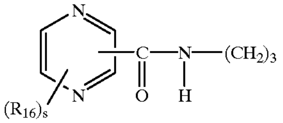
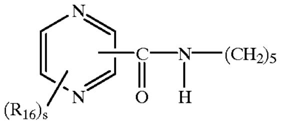
TABLE 31
| Position of heterocyclic ring | $(R_{16})_s$ |
|---|---|
| 2 | H |
| 2 | 5-$CH_3$ |
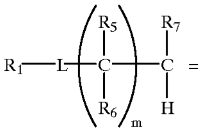
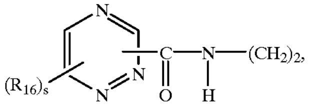
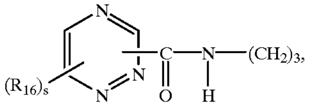
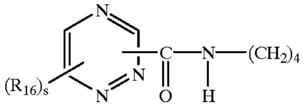
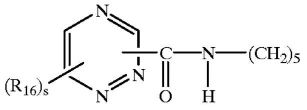
TABLE 32
| Positijon of heterocyclic ring | $(R_{16})_s$ |
|---|---|
| 3 | 5,6-$(CH_3)_2$ |

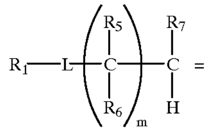
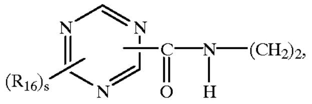
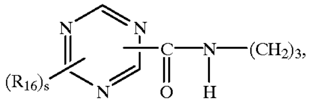
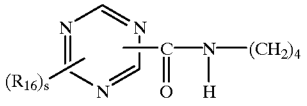
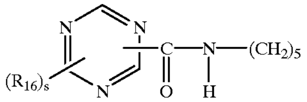
TABLE 33
| Postion of heterocyclic ring | $(R_{16})_S$ |
|---|---|
| 2 | $4,6\text{-}(C_6H_5)_2$ |
| 5 | $4,6\text{-}(CCl_3)_2$ |
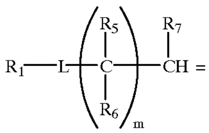
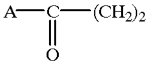
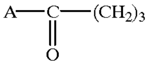
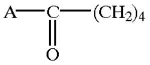
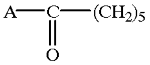
TABLE 34
| A—• | A—• | A—• |
|---|---|---|
| 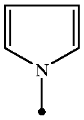 | 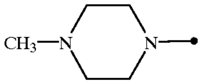 | |
TABLE 34-continued
| A—• | A—• | A—• |
|---|---|---|
| 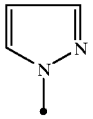 | 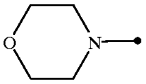 | |
| 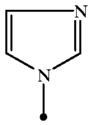 | 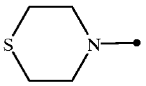 | |
| 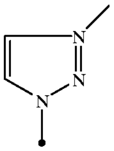 | 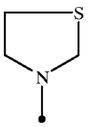 | |
| 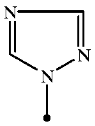 | 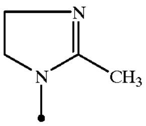 | |
| 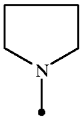 | 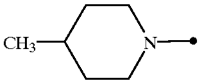 | |
| 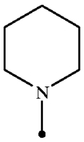 | 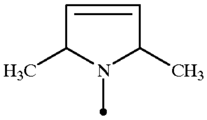 | |
| 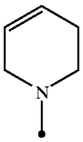 | | |
The compounds of general formula [IV] or [V], which are intermediates for the production of the present compounds, can be produced, for example, according to the following schemes 1 to 4:

SCHEME 1
(when Y and Z are both oxygen)
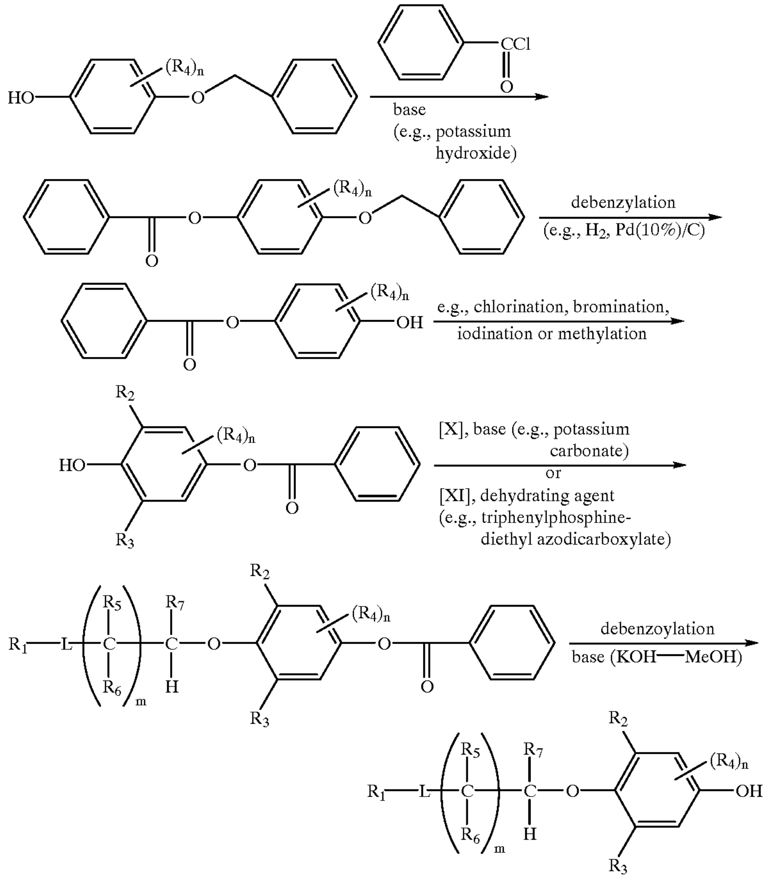
wherein $R_1$, $R_2$, $R_3$, $R_4$, $R_5$, $R_6$, $R_7$, m, n, $L_2$and L are each as defined above.
SCHEME 2
(when Y and Z are not both oxygen)
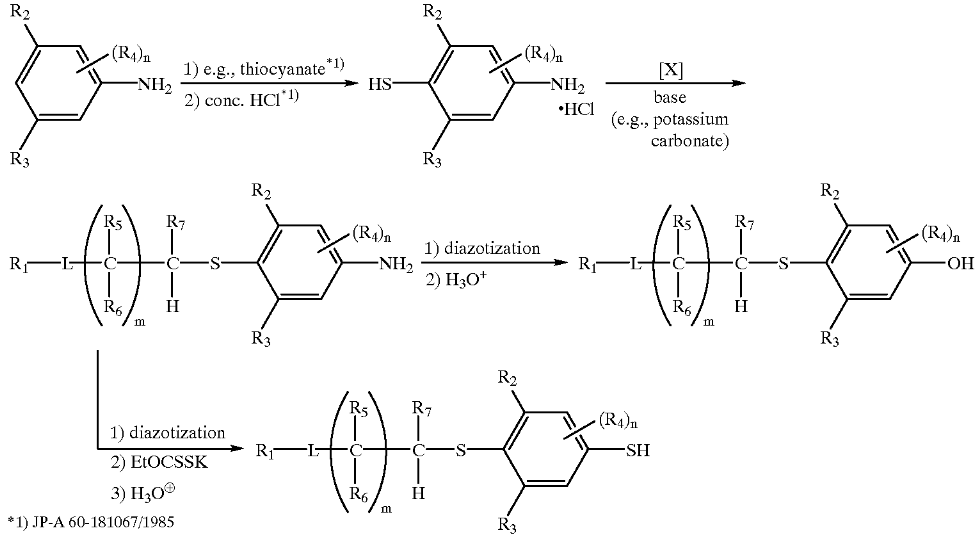
*1) JP-A 60-181067/1985
wherein $R_1$, $R_2$, $R_3$, $R_4$, $R_5$, $R_6$, $R_7$, m, n, $L_2$and L are each as defined above.

SCHEME 3
(when Y and Z are not both oxygen)
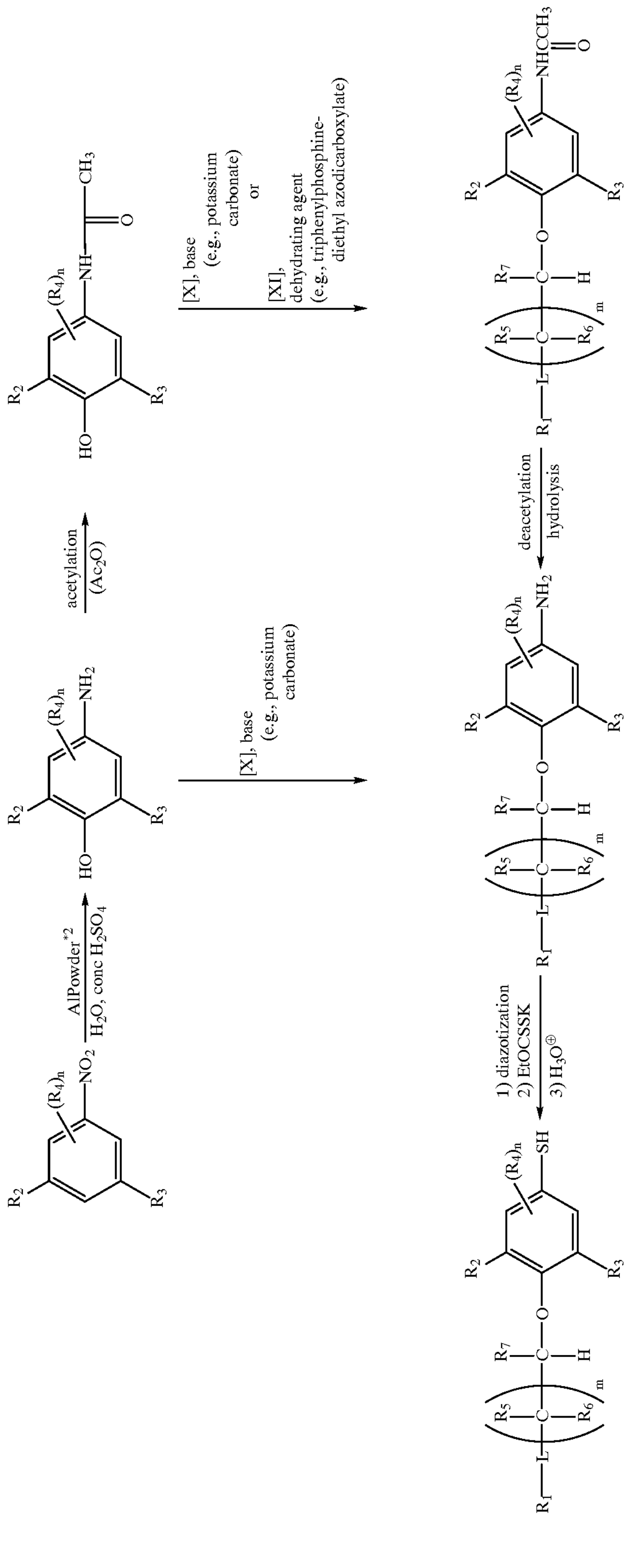
*2) H. J. Shine, "Aromatic Rearrangement", Elsevier, 182(1967)

wherein $R_1$, $R_2$, $R_3$, $R_4$, $R_5$, $R_6$, $R_7$, m, n, $L_2$and L are each as defined above.

SCHEME 4

(when Y is oxygen)

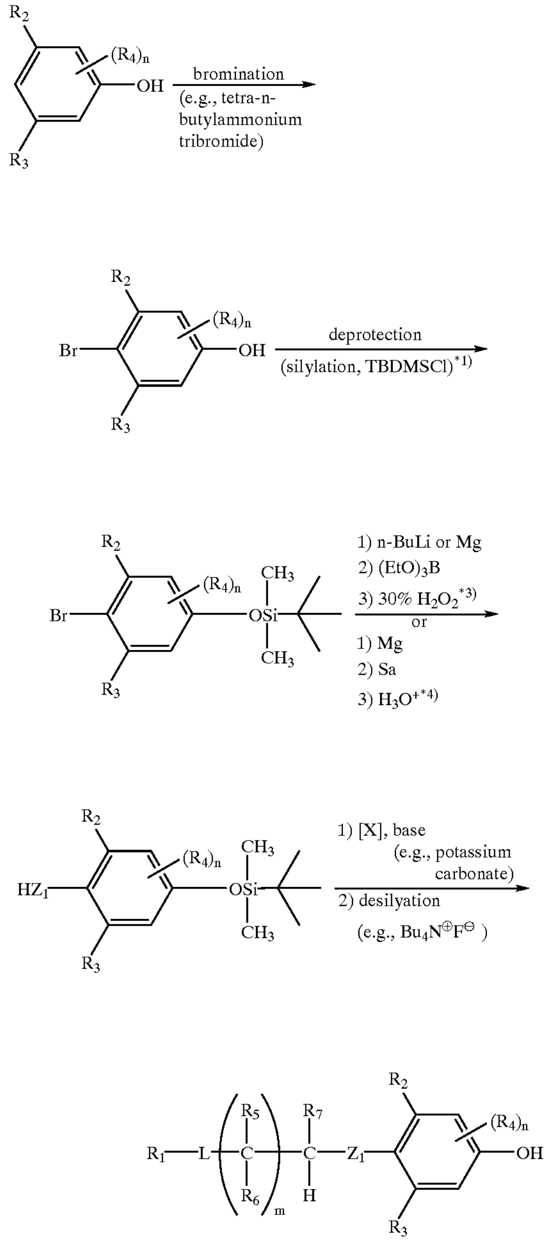

*3): J. Org. Chem., 22, 1001(1957)
*4): Ber., 72, 594(1939)

wherein $R_1$, $R_2$, $R_3$, $R_4$, $R_5$, $R_6$, $R_7$, m, n, $L_2$and L are each as defined above, and $Z_1$ is oxygen or sulfur.

The compounds of general formula [VI] and the alcohol compounds of general formula [VII], which are intermediates for the production of the present compounds, can be obtained from commercial sources or can be produced according to the following scheme 5:

SCHEME 5

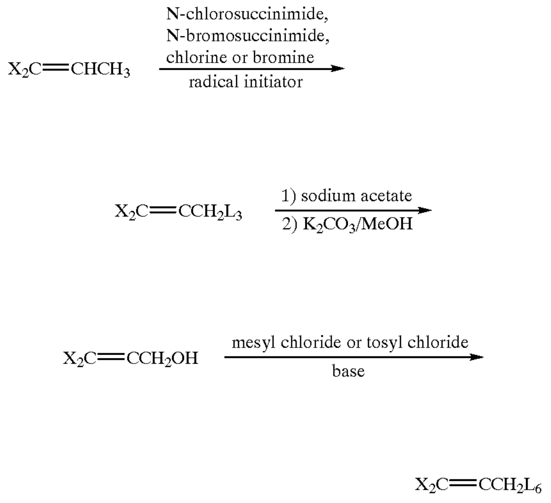

wherein $L_6$ is mesyloxy or tosyloxy, and $L_3$ and X are each as defined above.

The aldehyde compounds of general formula [VIII], which are intermediates for the production of the present compounds, can be produced, for example, according to the following scheme 6:

SCHEME 6

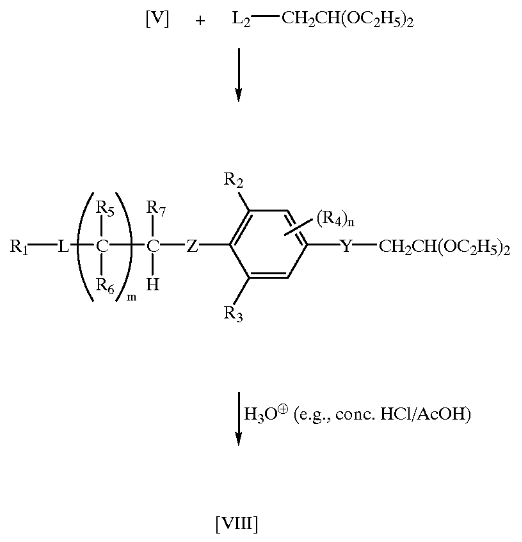

wherein all the symbols are each as defined above.

The compounds of general formula [IX], which are intermediates for the production of the present compounds, can be produced, for example, according to the following scheme 7:

SCHEME 7
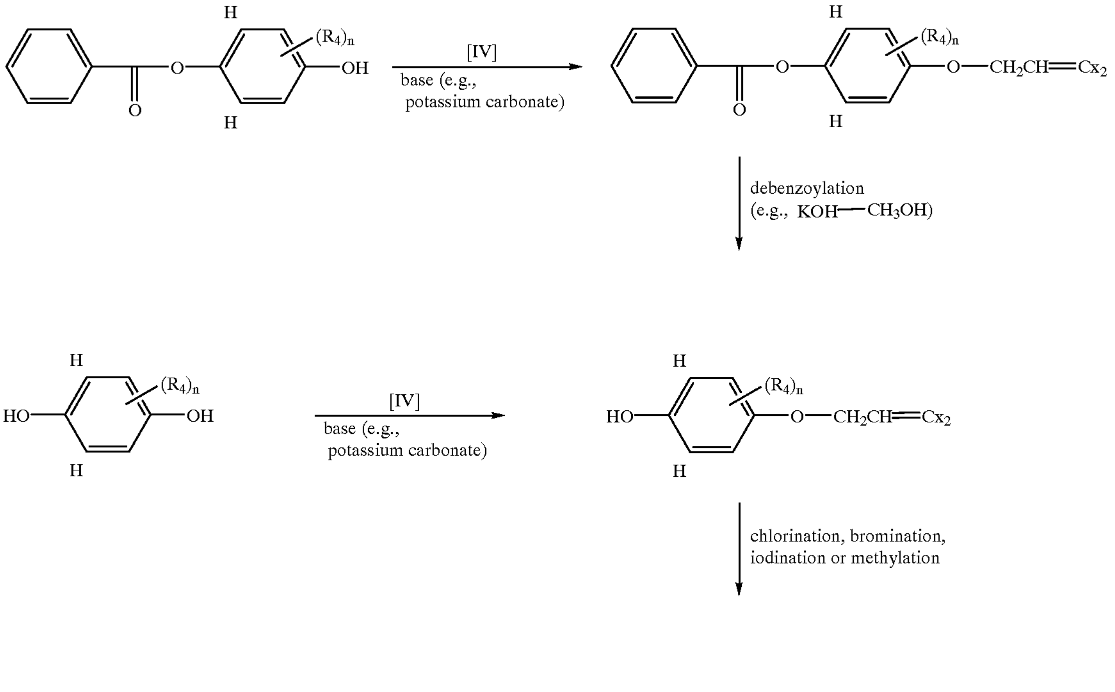
[IX]
The compounds of general formula [XVIII] wherein Y and Z are both oxygen, which are intermediates for the production of the present compounds, can be produced, for example, according to the following schemes 8.1 and 8.2:
SCHEME 8.1
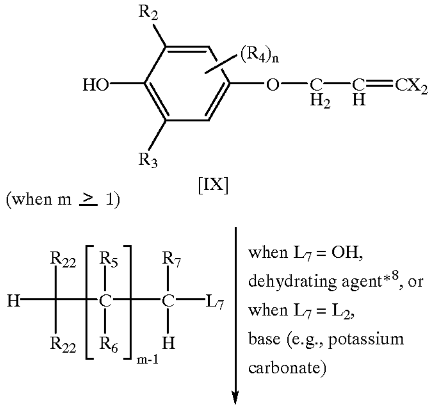
-continued
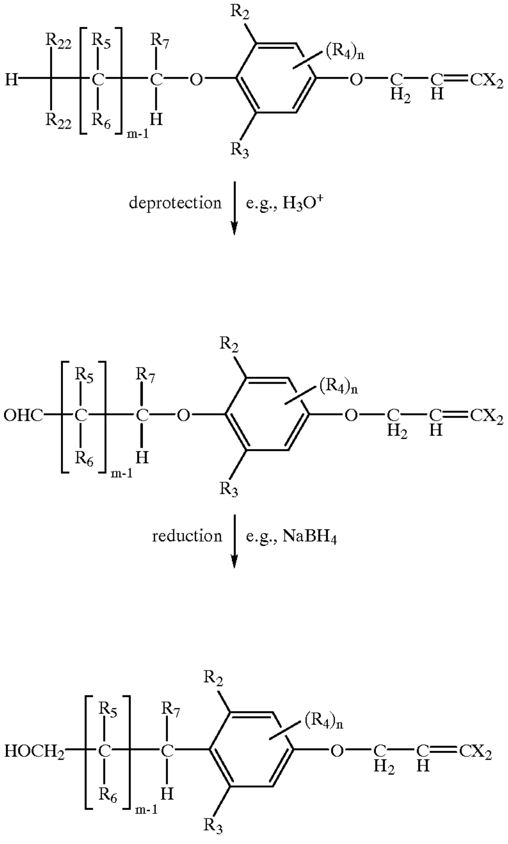

SCHEME 8.2

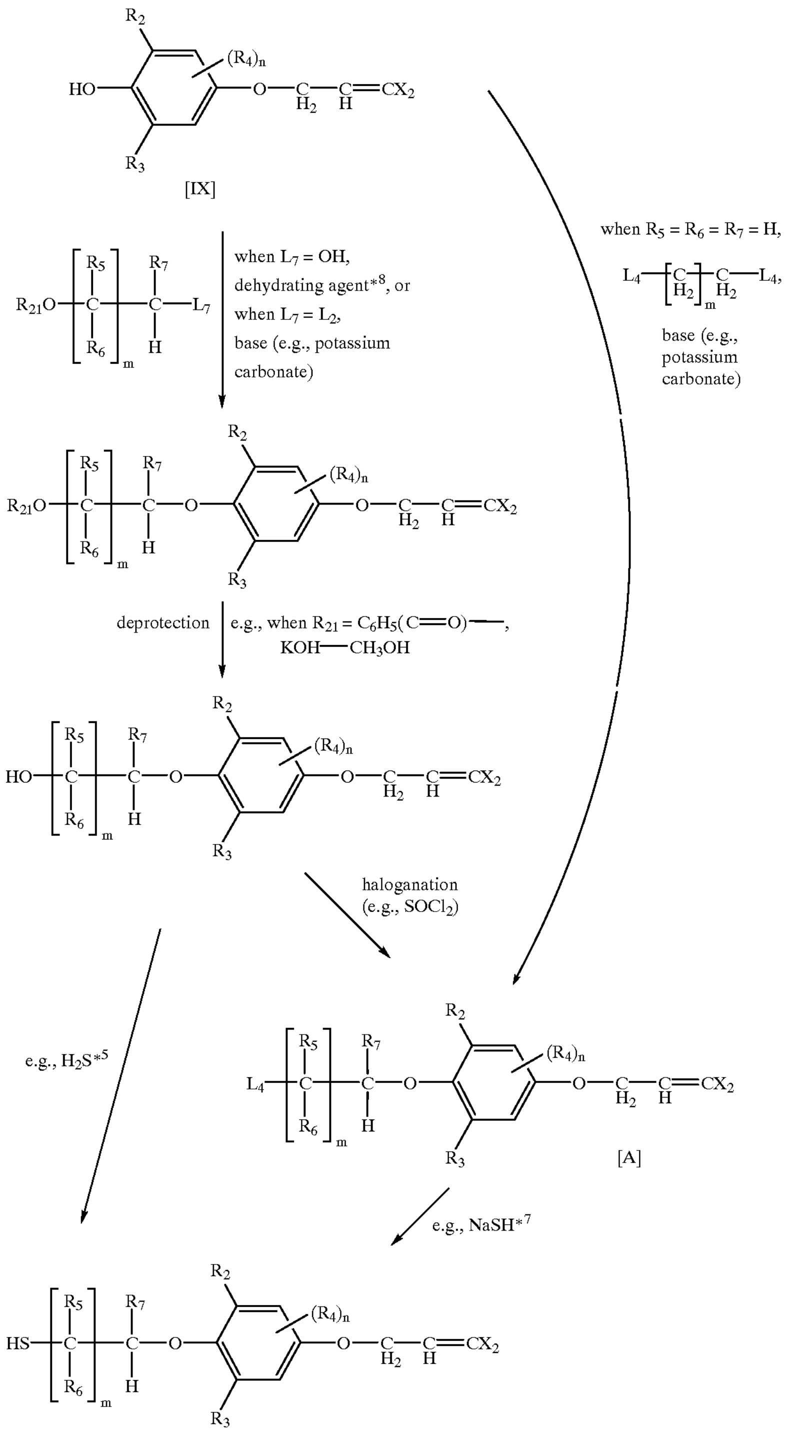

*5): e.g., R.L. Kramer et al., J. Am. Chem. Soc., 43, 880(1921)
*7): e.g., L.M. Ellis et al., J. Am. Chem. Soc., 54, 1674(1932)
*8): e.g., triphenylphosphine diethyl azodicarboxylate wherein $R_2$, $R_3$, $R_4$, $R_5$, $R_6$, $R_7$, X, $L_2$, $L_4$, m and n are each as defined above; $L_7$ hydroxyl, halogen, (e.g., chlorine, bromine, iodine), mesyl or tosyl; $R_{21}$ is a protecting group for alcohols (e.g., benzoyl); and $R_{22}$ is $C_1$–$C_4$ alkoxy (e.g., methoxy, ethoxy).

The compounds of general formula [II], [XIII], [XIV] or [XVII], which are intermediates for the production of the present compounds, can be produced, for example, according to the following schemes 9.1, 9.2 and 10:

SCHEME 9.1
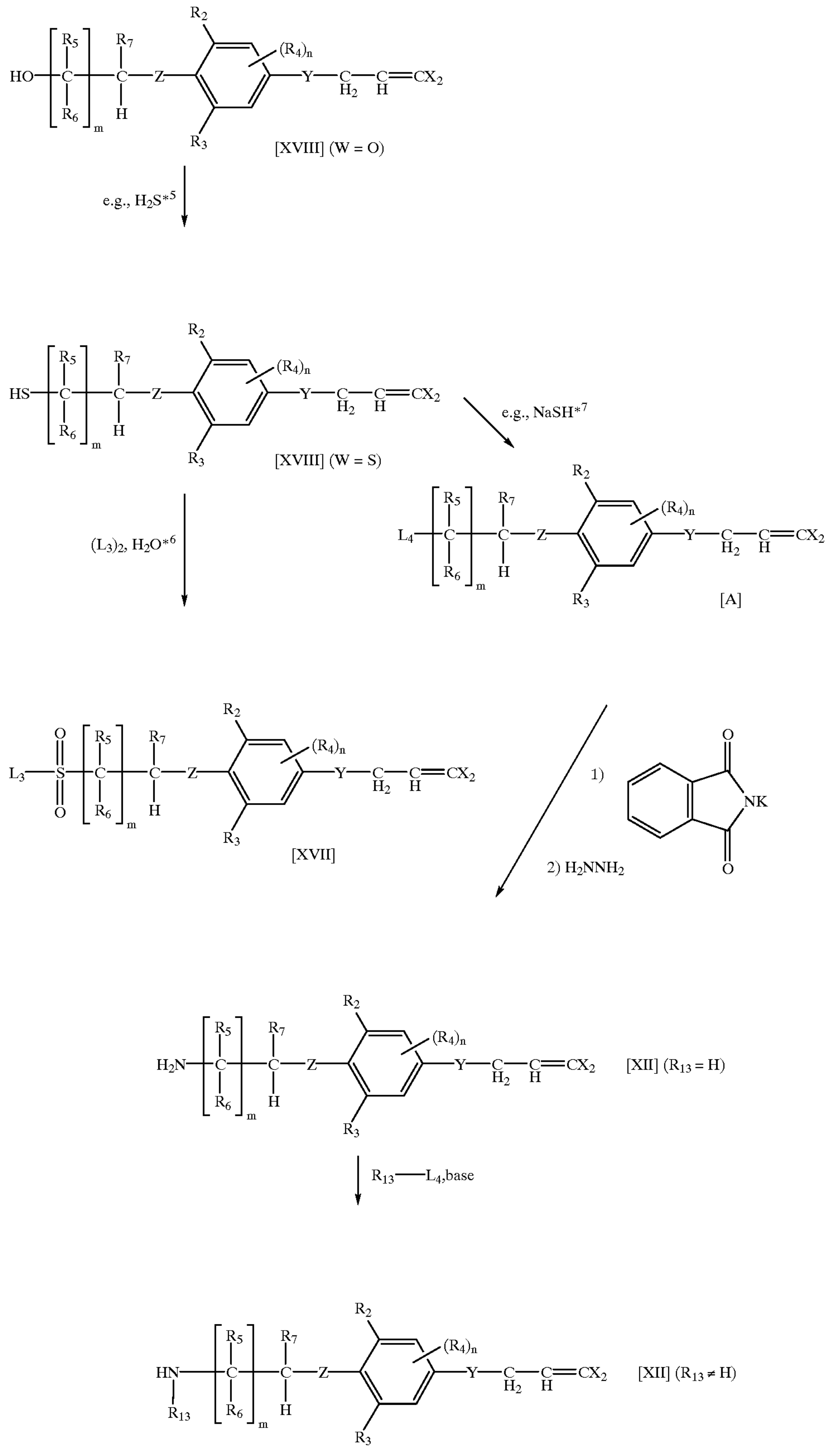

SCHEME 9.2

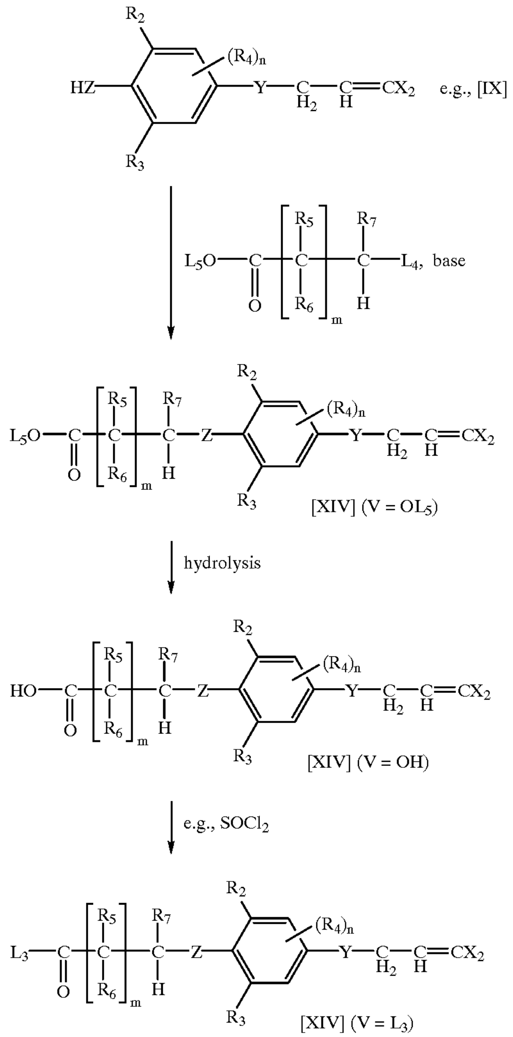

*5): e.g., R.L. Kramer et al., J. Am. Chem. Soc., 43, 880(1921)
*6): e.g., I.B. Douglass et al., J. Am. Chem. Soc., 60, 1486(1938)
*7): e.g., L.M. Ellis et al., J. Am. Chem. Soc., 54, 1674(1932)

wherein $R_2$, $R_3$, $R_4$, $R_5$, $R_6$, $R_7$, $R_{13}$, X, Y, Z, $L_3$, $L_4$, m and n are each as defined above; $L_5$ is methyl, ethyl or propyl; $L_7$ is hydroxyl, halogen (e.g., chlorine, bromine, iodine), mesyl or tosyl; $R_{21}$ is a protecting group for alcohols (e.g., benzoyl); and $R_{22}$ is $C_1$–$C_4$ alkoxy (e.g., methoxy, ethoxy).

SCHEME 10

(when Z is oxygen)

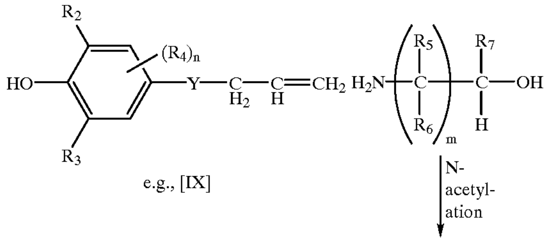

-continued

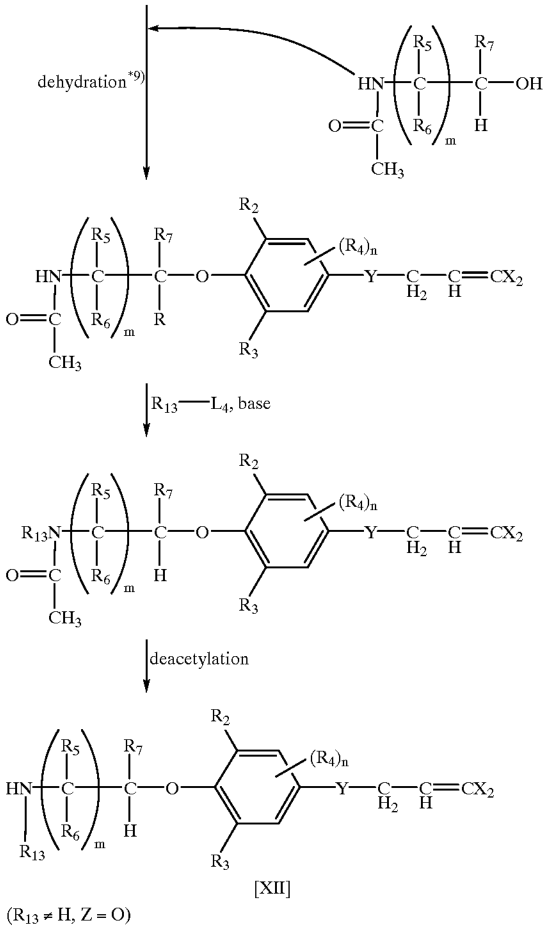

wherein $R_2$, $R_3$, $R_4$, $R_5$, $R_6$, $R_7$, $R_{13}$, X, Y, m and n are each as defined above.

*9): e.g., triphenylphosphine diethyl azodicarboxylate

The compounds of general formula [XIII], [XV], [XVI], [XIX] or [XXII], which are intermediates for the production of the present compounds, can be obtained from commercial sources or can be produced, for example, according to the following scheme 11 or 12:

SCHEME 11

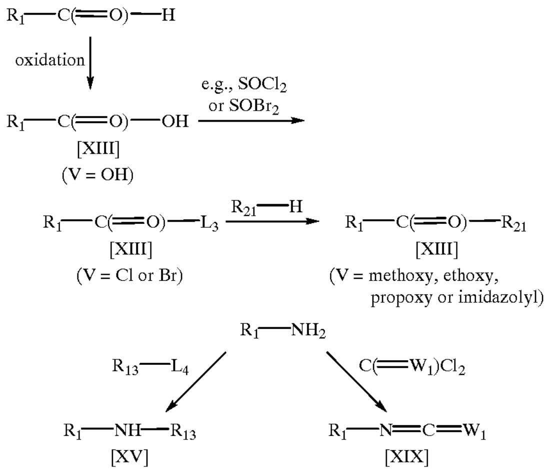

-continued

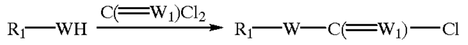

[XXII]
($L_3$ = Cl)

wherein $R_{21}$ is methoxy, ethoxy, propoxy or imidazolyl, and the other variables are each as defined above.

SCHEME 12

<in the case where $R_1$ is an aromatic ring such as benzene or pyridine ring>

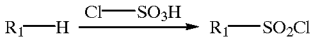

[XVI]

The present compounds are satisfactorily effective for the control of various noxious insects, examples of which are as follows:

Hemiptera:

Delphacide such as *Laodelphax striatellus, Nilaparavata lugens* and *Sogatella furcifera*, Deltocephalidae such as *Nephotettix cincticeps* and *Nephotettix virescens*, Aphididae, Pentatomidae, Aleyrodidae, Coccidae, Tingidae, Psyllidae, etc.

Lepidoptera:

Pyralidae such as *Chilo suppressalis, Cnaphalocrocis medinalis, Ostrinia nubilalis, Parapediasia teterrella, Notarcha derogata* and *Plodia interpunctella*, Noctuidae such as *Spodoptera litura, Spodoptera exigua, Spodoptera littoralis, Pseudaletia separta, Mamestra brassicae, Agrotis ipsilon*, Trichoplusia spp., Heliothis spp. and Helicoverpa spp., Pieridae such as *Pieris rapae crucivora*, Tortricidae such as Adoxophyes spp., *Grapholita molesta* and *Cydia pomonella*, Carposinidae such as *Carposina niponensis*, Lyonetiidae such as Lyonetia spp., Lymantriidae such as Lymantria spp. and Euproctis spp., Yponomeutidae such as *Plutella xylostella*, Gelechiidae such as *Pectinophora gossypiella*, Arctiidae such as *Hyphantria cunea*, Tineidae such as *Tinea translucens* and *Tineola bisselliella*, etc.

Diptera:

Culex such as *Culex pipiens pallens* and *Cules tritaeniorhynchus*, Aedes such as *Aedes aegypti* and *Aedes albopictus*, Anopheles such as *Anophelinae sinensis*, Chironomidae, Muscidae such as *Musca domestica* and *Muscina stabulans*, Calliphori-dae, Sarcophagidae, *Fannia canicularis*, Anthomyiidae such as *Delia Platura* and *Delia antigua*, Trypetidae, Drosophilidae, Psychodidae, Simuliidae, Tabanidae, Stomoxyinae, Agromyzidae, etc.

Coleoptera:

Diabrotica such as *Diabrotica virgifera* and *Diabrotica undecimpunctata*, Scarabaeidae such as *Anomala cuprea* and *Anomala rufocuprea*, Curculionidae such as *Sitophilus zeamais, Lissorphoptrus oryzophilus, Hypera pastica*, and *Calosobruchys chinensis*, Tenebrionidae such as *Tenebrio molitor* and *Tribolium castaneum*, Chrysomelidae such as *Aulacophorafemoralis, Phyllotreta striolata*, Anobiidae and *Leoptinotarsa decemlineata*, Anobiidae, Epilachna spp. such as *Epilachna vigintioctopunctata*, Lyctidae, Bostrychidae, Cerambycidae, *Paederus fuscipes*, etc.

Dictyoptera:

*Blattella germanica, Periplaneta fuliginosa, Peroplaneta americana, Peri-planeta brunnea, Blatta orientalis*, etc.

Thysanoptera:

*Thrips palmi, Thrips tabaci, Thrips hawaiiensis*, etc.

Hymenoptera:

Formicidae, Vespidae, Bethylidae, Tenthredinidae such as *Athalia rosae japonensis*, etc.

Orthoptera:

Gryllotalpidae, Acrididae, etc.

Siphonaptera:

*Purex irritans* etc.

Anoplura:

*Pediculus humanus capitis, Phthirus pubis*, etc.

Isoptera (termites):

*Reticulitermes speratus, Coptotermes formosanus*, etc.

The present compounds are also effective for the control of various noxious insects having resistance to conventional insecticides.

When the present compounds are used as active ingredients of insecticides, they may be used as such without any addition of other ingredients. The present compounds are, however, usually formulated into dosage forms such as oil sprays, emulsifiable concentrates, wettable powders, flowables, granules, dusts, aerosols, fumigants (foggings) and poison baits. These dosage forms are usually prepared by mixing the present compounds with solid carriers, liquid carriers, gaseous carriers or baits, and if necessary, adding surfactants and other auxiliaries used for formulation.

Each of the dosage forms usually contains at least one of the present compounds as an active ingredient in an amount of 0.01% to 95% by weight.

Examples of the solid carrier to be used for formulation are fine powder or granules of clay materials such as kaolin clay, diatomaceous earth, synthetic hydrated silicon oxide, bentonite, Fubasarni clay and acid clay; various kinds of talc, ceramics and other inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride.

Examples of the liquid carrier are water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitrites such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier or propellant are flon gas, butane gas, LPG (liquefied petroleum gas), dimethyl ether and carbon dioxide.

Examples of the surfactant are alkyl sulfates, alkyl sulfonates, alkyl arylsulfonates, alkyl aryl ethers and their polyoxyethylene derivatives, polyethylene glycol ethers, polyhydric alcohol esters and sugar alcohol derivatives.

Examples of the auxiliaries used for formulation, such as fixing agents or dispersing agents, are casein, gelatin, polysaccharides such as starch, gum arabic, cellulose derivatives and alginic acid, lignin derivatives, bentonite, sugars, and synthetic watersoluble polymers such as polyvinyl alcohol, polyvinyl pyrrolidone and polyacrylic acid.

Examples of the stabilizer are PAP (isopropyl acid phosphate), BHT (2,6-di-tert-butyl-4-methylphenol), BHA (mixtures of 2-t-butyl-4-methoxyphenol and 3-tert-butyl-4-methoxyphenol), vegetable oils, mineral oils, surfactants, fatty acids and their esters.

Examples of the base material to be used in the poison baits are bait materials such as grain powder, vegetable oils, sugars and crystalline cellulose; antioxidants such as dibutylhydroxytoluene and nordihydroguaiaretic acid; preservatives such as dehydroacetic acid; substances for preventing erroneous eating, such as red pepper powder, attractant flavors such as cheese flavor or onion flavor.

The dosage forms thus obtained are used as such or after diluted with water.

The dosage forms may also be used in combination with other insecticides, nematocides, acaricides, bactericides, fungicides, herbicides, plant growth regulators, synergists, fertilizers, soil conditioners and/or animal feed under non-mixing conditions or pre-mixing conditions.

Examples of the insecticide, acaricide and/or nematocide which can be used are organophosphorus compounds such as Fenitrothion [O,O-dimethyl O-(3-methyl-4-nitrophenyl) phosphorothioate], Fenthion [O,O-dimethyl O-(3-methyl-4-methylthio)-phenyl)phophorothioate], Diazinon [O,O-diethyl-O-2-isopropyl-6-methylpyrimidin-4-yl-phosphorothioate], Chlorpyriphos [O,O-diethyl-O-3,5,6-trichloro-2-pyridylphosphorothioate], Acephate [O,S-dimethylacetylphosphoramidothioate], Methidathion [S-2, 3-dihydro-5-methoxy-2-oxo-1,3,4-thiadiazol-3-ylmethyl O,O-dimethylphosphorodithioate], Disulfoton [O,O-diethyl S-2-ethylthioethylphosphorothioate], DDVP [2,2-dichlorovinyldimethylphosphate], Sulprofos [O-ethyl O-4-(methylthio)phenyl S-propyl phosphorodithioate], Cyanophos [O-4-cyanophenyl O,O-dimethylphosphorothioate], Dioxabenzofos [2-methoxy-4H-1,3,2-benzodioxaphosphinine-2-sulfide], Dimethoate [O,O-dimethyl-S-(N-methylcarbamoylmethyl)dithiophosphate], Phenthoate [ethyl 2-dimethoxyphosphinothioylthio(phenyl)acetate], Malathion [diethyl(dimethoxyphosphinothioylthio) succinate], Trichlorfon [dimethyl 2,2,2-trichloro-1-hydroxyethylphosphonate], Azinphos-methyl [S-3,4-dihydro-4-oxo-1,2,3-benzotriazin-3-ylmethyl O,O-dimethylphosphorodithioate], Monocrotophos [dimethyl (E)-1-methyl-2-(methylcarbamoyl)vinylphosphate], Ethion [O,O,O',O'-tetraethyl S,S'-methylenebis (phosphorodithioate)] and Profenofos [O-4-bromo-2-chlorophenyl O-ethyl S-propyl phosphorothioate]; carbamate compounds such as BPMC [2-sec-butylphenylmethylcarbamate], Benfuracarb [ethyl N-[2,3-dihydro-2,2-dimethylbenzofuran-7-yloxycarbonyl(methyl) amino thio]-N-isopropyl -β-alaninate], Propoxur [2-isopropoxyphenyl N-methylcarbamate], Carbosulfan [2,3-dihydro-2,2-dimethyl-7-benzo[b]furanyl N-dibutylaminothio-N-methylcarbamate], Carbaril [1-naphthyl-N-methylcarbamate], Methomyl [S-methyl-N-[(methylcarbamoyl)oxy]thio-aceti midate], Ethiofencarb [2-(ethylthiomethyl)phenylmethylcarbamate], Aldicarb [2-methyl-2-(methylthio)propanaldehyde O-methylcarbamoyloxime], Oxamyl [N,N-dimethyl-2-methylcarbamoyloxyimino-2-(methylthio)acetamide], Fenothiocarb [S-(4-phenoxybutyl)-N,Ndimethylthiocarbamate], Thiodicarb [3,7,9,13-tetramethyl-5, 11-dioxa-2,8,14-trithia-4, 7,9,12-tetraazapentadeca-3,12-diene-6,10-dione] and Alanylcarb [ethyl (Z)-N-b enzyl-N-{[methy 1(1-methylthioethylideneaminooxycarbonyl)amino]thio}-β-alaninate]; pyrethroid compounds such as Etofenprox [2-(4-ethoxyphenyl)-2-methylpropyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenpropathrin [(RS)-β-cyano-3-phenoxybenzyl 2,2,3,3-tetramethylcyclopropanecarboxylate], Cypermethrin [(RS)-α-cyano-3-phenoxybenzyl (1RS,3 RS)-3-(2,2-dichlorovinyl)-2,2-dimethylcyclopropanecarboxylate], Permethrin [3-phenoxybenzyl (1RS, 3RS)-3-(2,2-dichlorovinyl)-2,2-dimethylcyclopropanecarboxylate], Cyhalothrin [(RS)-α-cyano-3-phenoxybenzyl (Z)-(lRS)-cis-3-(2-chloro-3,3,3-trifluoroprop-1-enyl)-2,2-dimethylcyclopropanecarboxylate], Deltamethrin [(S)-α-cyano-m-phenoxybenzyl (1R,3R)-3-(2,2-dibromovinyl)-2, 2-dimethylcyclopropanecarboxylate], Cycloprothnfn [(RS)-α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α,α,α-trifluoro-p-tolyl)-D-valinate], Bifenthrin [2-methylbiphenyl-3-ylmethyl) (Z)-(1RS)-cis-3-(2-chloro-3,3,3-trifluoroprop-1-enyl)-2,2-dimethylcyclopropane carboxylate], Acrinathrin [(S)-α-cyano-(3-phenoxyphenyl)methyl [1R-{α(S*),3α(Z) }]-2,2-dimethyl-3-[3-oxo-3-(2,2,2-trifluoro-1-(trifluoromethyl)ethoxy-1-propenyl]cyclopropanecarboxylate], 2-methyl-2-(4-bromodifluoromethoxyphenyl) propyl (3-phenoxybenzyl) ether, Traromethrin [(S)-α-cyano-3-phenoxylbenzyl (1R,3R)-3-[(1'RS)-(1',1',2',2'-tetrabromoethyl)]-2,2-dimethylcyclopropanecarboxylate] and Silafluofen [4-ethoxylphenyl [3-(4-fluoro-3-phenoxyphenyl)propyl]dimethylsilane]; thiadiazine derivatives such as Buprofezin [2-tert-butylimino-3-isopropyl-5-phenyl-1,3,5-thiadiazin-4-one]; nitroimidazolidine derivatives such as Imidacloprid [1-(6-chloro-3-pyridylmethyl)-N-nitroimidazolidin-2-ylidenamine]; Nereistoxin derivatives such as Cartap [S,S'-(2-dimethylaminotrimethylene)bisthiocarbamate], Thiocyclam [N,N-dimethyl-1,2,3-trithian-5-ylamine] and Bensultap [S,S'-2-dimethylaminotrimethylene di(benzene-thiosulfonate)]; N-cyanoamidine derivatives such as acetamiprid [N-cyano-N'-methyl-N'-(6-chloro-3-pyridylmethyl)acetamidine]; chlorinated hydrocarbon compounds such as Endosulfan [6,7,8,9,10,10-hexachloro-1,5, 5a,6,9,9a-hexahydro-6,9-methano-2,4,3-benzodioxathiepinoxide], γ-BHC [1,2,3,4,5,6-hexachlorocyclohexane] and Kelthane [1,1-bis(chlorophenyl)-2,2,2-trichloroethanol]; benzoylphenylurea compounds such as Chlorfluazuron [1-(3,5-dichloro-4-(3-chloro-5-trifluoromethylpyridin-2-yloxy)phenyl)-3-(2,6-difluorobenzoyl)urea], Teflubenzuron [1-(3,5-dichloro-2,4-difluorophenyl)-3-(2,6-difluorobenzoyl)urea] and Fulphenoxron [1-(4-(2-chloro-4-trifluoromethylphenoxy)-2-fluorophenyl)-3-(2,6-difluorobenzoyl)urea]; formamidine derivatives such as Amitraz [N,N'-[(methylimino) dimethylidine]-di-2,4-xylidine] and Chlordimeform [N'-(4-chloro-2-methylphenyl)-N,N-dimethylmethanimidamide]; thiourea derivatives such as Diafenthiuron [N-(2,6-diisopropyl -4-phenoxyphenyl)N'-tert-butyl carbo diimide]; Bromopropylate [isopropyl 4,4'-dibromobenzylate], Tetradifon [4-chlorophenyl-2,4,5-trichlorophenylsulfone], Quinomethionate [S,S-6-methylquinoxaline-2,3-diyldithiocarbonate], Propargite [2-(4-tert-butylphenoxy) cyclohexyl prop-2-yl sulfite], Fenbutatin oxide [bis[tris(2-methyl-2-phenylpropyl)tin]oxide], Hexythiazox [(4RS, 5RS)-5-(4-chlorophenyl)-N-chlorohexyl-4-methyl-2-oxo-1, 3-thiazolidine-3-carboxamide], Chlofentezine [3,6-bis(2-chlorophenyl)-1,2,4,5-tetrazine], Pyridaben [2-tert-butyl-5-(4-tert-butylbenzylthio)-4-chloropyridazin-3(2H)-one], Fenpyroximate [tert-butyl (E)-4-[(1,3-dimethyl-5-phenoxypyrazol-4-yl)methyleneaminooxymethyl] benzoate], Tebfenpyrad [N-4-tertbutylbenzyl)-4-chloro-3-ethyl-1-methyl-5-pyrazolecarboxamide], polynactin complexes including tetranactin, dinactin and trinactin; Milbemectin, Avermectin, Ivermectin, Azadilactin [AZAD], Pyrimidifen [5-chloro-N-[2-{4-(2-ethoxyethyl)-2,3-dimethylphenoxy}ethyl]-6-ethylpyrimidin-4-amine], Chlorfenapyl [4-bromo-2-(4-chlorophenyl)-1-ethoxymethyl-5-trifluoromethylpyrrole-3-carbonitrile], Tebfenozide [N-tert-butyl-N'-(4-ethylbenzoyl)-3,5-dimethylbenzohydrazide], Fipronyl [5-amino-1-(2,6-dichloro-α,α,α-trifluoro-p-tolyl)-4-trifluoromethylsulfinylpyrazole-3-carbonitrite] and Pimetrozine [2,3,4,5-tetrahydro-3-oxo-4-[(pyridin-3-yl)-methyleneamino]-6-methyl-1,2,4-triazine].

When the present compounds are used as active ingredients of insecticides for agriculture, the application amount thereof is usually in the range of 0.1 to 100 g per 10 ares. In the case of emulsifiable concentrates, wettable powders and flowable concentrates, which are used after diluted with water, the application concentration thereof is usually in the range of 0.1 to 500 ppm. In the case of granules and dusts, they are applied as such without any dilution. When the present compounds are used as active ingredients of insecticides for epidemic prevention, they are formulated into dosage forms such as emulsifiable concentrates, wettable powders and flowable concentrates, which are applied after diluted with water to a typical concentration of 0.1 to 500 ppm; or they are formulated into dosage forma such as oil sprays, aerosols, fumigants and poisonous baits, which are applied as such without any dilution.

The application amount and application concentration may vary depending upon various conditions such as dosage form type, application time, place and method, kind of noxious insects, and degree of damage, and they can be increased or decreased without limitation to the above range.

The present invention will be further illustrated by the following production examples, formulation examples and test examples; however, the present invention is not limited to these examples.

The following are production examples for the present compounds according to various production processes.

PRODUCTION EXAMPLE 1

Production of Compound (2) by Production Process F

To a solution of 0.21 g of 3,5-dichloro-4-(3-aminopropyloxy)-1-(3,3-dichloro-2-propenyloxy)benzene and 0.07 g of triethylamine dissolved in 5 ml of dichloromethane was added dropwise a solution of 0.11 g of 4-chlorobenzoyl chloride dissolved in 5 ml of dichloromethane, while stirring under ice cooling. After stirring at room temperature for 6 hours, the reaction mixture was washed with water and then concentrated to give a residue. The residue was subjected to silica gel chromatography, which afforded 0.21 g of 3,5-dichloro-4-(3-(4-chlorobenzamido)propyloxy)-1-(3,3-dichloro-2-propenyloxy)benzene (71% yield), m.p., 95.1° C.

PRODUCTION EXAMPLE 2

Production of Compound (7) by Production Process F

To a solution of 0.21 g of 3,5-dichloro-4-(3-aminopropyloxy)-1-(3,3-dichloro-2-propenyloxy)benzene and 0.07 g of triethylamine dissolved in 5 ml of dichloromethane was added dropwise a solution of 0.15 g of 4-trifluoromethylbenzoyl chloride dissolved in 5 ml of dichloromethane, while stirring under ice cooling. After stirring at room temperature for 6 hours, the reaction mixture was washed with water and then concentrated to give a residue. The residue was subjected to silica gel chromatography, which afforded 0.25 g of 3,5-dichloro-4-(3-(4-trifluoromethylbenzamido)propyloxy)-1-(3,3-dichloro-2-propenyloxy)benzene (79% yield), m.p., 93.5° C.

PRODUCTION EXAMPLE 3

Production of Compound (10) by Production Process F

To a solution of 0.15 g of 4-trifluoromethylcinnamic acid and 0.07 g of triethylamine dissolved in 5 ml of dichloromethane was added 0.14 g of 1-ethyl-3-(3-dimethylaminopropyl)carbodiimide (WSC) hydrochloride, while stirring under ice cooling. After stirring for 30 minutes, a solution of 0.20 g of 3,5-dichloro-4-(2-aminoethoxy)-1-(3,3-dichloro-2-propenyloxy)benzene dissolved in 5 ml of dichloromethane was added dropwise. After stirring at room temperature for 12 hours, the reaction mixture was concentrated to give a residue. The residue was subjected to silica gel chromatography, which afforded 0.20 g of 3,5-dichloro-4-(2-(4-trifluoromethylcinnamic)ethoxy)-1-(3,3-dichloro-2-propenyloxy)benzene (63% yield), m.p., 109.4° C.

PRODUCTION EXAMPLE 4

Production of Compound (24) by Production Process G

To a solution of 0.26 g of 4-(2,6-dichloro-4-(3,3-dichloro-2-propenyloxy)-phenoxy)butyric acid and 0.07 g of triethylamine dissolved in 5 ml of dichloromethane was added dropwise 0.14 g of 1-ethyl-3-(3-dimethylaminopropyl) carbodiimide (WSC) hydrochloride, while stirring under ice cooling. After stirring for 30 minutes, a solution of 0.12 g of 4-trifluoromethoxyaniline dissolved in 5 ml of dichloromethane was added dropwise. After stirring at room temperature for 12 hours, the reaction mixture was concentrated to give a residue. The residue was subjected to silica gel chromatography, which afforded 0.26 g of 3,5-dichloro-4-(3-(N-(4-trifluoromethoxyphenyl)carbamoyl)-propyloxy)-1-(3,3-dichloro-2-propenyloxy)benzene (70% yield), m.p., 88.8° C.

PRODUCTION EXAMPLE 5

Production of Compound (25) by Production Process I

To a solution of 0.20 g of 3,5-dichloro-4-(2-aminoethoxy)-1-(3,3-dichloro-2-propenyloxy)benzene and 0.10 g of triethylamine dissolved in 5 ml of dichloromethane was added dropwise a solution of 0.16 g of 4-trifluoromethoxybenzenesulfonyl chloride dissolved in 5 ml of dichloromethane, while stirring under ice cooling. After stirring at room temperature for 6 hours, the reaction mixture was concentrated to give a residue. The residue was subjected to silica gel chromatography, which afforded 0.20 g of 3,5-dichloro-4-(2-(4-trifluoromethoxybenzenesulfonamido)ethoxy)-1-(3,3-dichloro-2-propenyloxy)benzene (60% yield), $n_D^{23.0}$ 1.5470.

PRODUCTION EXAMPLE 6

Production of Compound (26) by Production Process M

A solution of 0.20 g of 3,5-dichloro-4-(2-aminoethoxy)-1-(3,3-dichloro-2-propenyloxy)benzene and 0.14 g of 4-trifluoromethoxyphenyl isocyanate dissolved in 10 ml of toluene was heated under reflux, while stirring, for 12 hours, and the reaction mixture was then concentrated to give a residue. The residue was subjected to silica gel chromatography, which afforded 0.15 g of 3,5-dichloro-4-(2-(N'-(4-trifluoromethoxyphenyl)ureido)ethoxy)-1-(3,3-dichloro-2-propenyloxy)benzene (46% yield), m.p., 1 25.4° C.

PRODUCTION EXAMPLE 7

Production of Compound (28) by Production Process K

A solution of 0.17 g of 3,5-dichloro-4-(3-hydroxypropyloxy)-1-(3,3-dichloro-2-propenyloxy) benzene, 0.09 g of 4-chlorophenyl isocyanate and a catalytic amount of pyridine dissolved in 10 ml of toluene was heated at 60° to 70° C., while stirring, for 3 hours, and the reaction mixture was then concentrated to give a residue. The residue was subjected to silica gel chromatography, which afforded 0.19 g of 3,5-dichloro-4-(3-(N-(4-chlorophenyl) carbamoyloxy)propyloxy)-1-(3,3-dichloro-2-propenyloxy) benzene (77% yield), m.p., 54.3° C.

PRODUCTION EXAMPLE 8

Production of Compound (7) by Production Process A

To a mixture of 2.0 g of 3,5-dichloro-4-(3-(4-trifluoromethyl)benzamido)-propyloxy)phenol, 0.68 g of potassium carbonate and 20 ml of N,N-dimethylformamide was added dropwise a mixed solution of 0.71 g of 1,1,3-trichloropropene and 5 ml of N,N-dimethylformamide, while stirring at room temperature. After stirring at room temperature for 6 hours, the reaction mixture was poured into ice water and extracted twice with 50 ml of diethyl ether. The ether layers were combined, washed with water, dried over anhydrous magnesium sulfate, and then concentrated to give crude crystals. These crude crystals were ground and washed with n-hexane, which afforded 1.9 g of 3,5-dichloro-1-(3,3-dichloro-2-propenyloxy)-4-(3-(4-(trifluoromethyl)benzamido)-propyloxy)benzene (75% yield), m.p., 93.5° C.

PRODUCTION EXAMPLE 9

Production of Compound (59) by Production Process A

To a mixture of 0.66 g of 3-ethyl-5-methyl-4-(3-(4-(trifluoromethyl)benzamido)propyloxy)phenol, 0.29 g of potassium carbonate and 20 ml of N,N-dimethylformamide was added dropwise a mixed solution of 0.28 g of 1,1,3-trichloropropene and 5 ml of N,N-dimethylformamide, while stirring at room temperature. After stirring at room temperature for 6 hours, the reaction mixture was poured into ice water and extracted twice with 50 ml of diethyl ether. The ether layers were combined, washed with water, dried over anhydrous magnesium sulfate, and then concentrated to give crude crystals. The crude crystals were ground and washed with n-hexane, which afforded 0.48 g of 3-ethyl-5-methyl-1-(3,3-dichloro-2-propenyloxy)-4-(3-(4-(trifluoromethyl)benzamido)propyloxy)benzene (58% yield), m.p., 92.2° C.

PRODUCTION EXAMPLE 10

Production of Compound (67) by Production Process F

To a mixture of 0.96 g of 4-(3-aminopropyloxy)-3,5-dichloro-1-(3,3-dichloro-2-propenyloxy)benzene, 0.53 g of 5-(trifluoromethyl)-2-pyridinecarboxylic acid, 0.37 g of triethylamine and 10 ml of chloroform was added 0.64 g of WSC hydrochloride, while stirring at room temperature. After stirring at room temperature for 6 hours, the reaction mixture was concentrated to give a residue. The residue was subjected to silica gel chromatography, which afforded 0.15 g of 3,5-dichloro-1-(3,3-dichloro-2-propenyloxy)-4-(3-(5-(trifluoromethyl)picolinamido)propoxy)benzene (10% yield), m.p., 55.1° C.

PRODUCTION EXAMPLE 11

Production of Compound (34) by Production Process F

To a mixture of 0.35 g of 4-(3-aminopropyloxy)-3,5-dichloro-1-(3,3-dichloro-2-propenyloxy)benzene, 0.19 g of 5-bromo-2-furancarboxylic acid, 0.18 ml of triethylamine and 10 ml of chloroform was added 0.23 g of WSC hydrochloride, while stirring at room temperature. After stirring at room temperature for 6 hours, the reaction mixture was concentrated to give a residue. The residue was dissolved in 50 ml of ethyl acetate, and the ethyl acetate layer was successively washed with 10% hydrochloric acid, saturated aqueous sodium hydrogen carbonate solution and saturated saline solution, dried over anhydrous magnesium sulfate, and then concentrated to give a residue. The residue was subjected to silica gel chromatography, which afforded 0.35 g of 3,5-dichloro-1-(3,3-dichloro-2-propenyloxy)-4-(3-(5-bromo-2-furancarboxamido)propyloxy)-benzene (64% yield), $n_D^{24.0}$ 1.5918.

PRODUCTION EXAMPLE 12

Production of Compound (93) by Production Process F

To a mixture of 0.42 g of 3,5-dichloro-1-(3,3-dichloro-2-propenyloxy)-4-(3-(methylamino)propyloxy)benzene, 0.18 ml of triethylamine and 10 ml of chloroform was added 0.18 ml of 4-(trifluoromethyl)benzoyl chloride, while stirring under ice cooling. After stirring at room temperature for 6 hours, the reaction mixture was concentrated to give a residue. The residue was dissolved in 50 ml of ethyl acetate, and the ethyl acetate layer was successively washed with 10% hydrochloric acid, saturated aqueous sodium hydrogen carbonate solution and saturated saline solution, dried over anhydrous magnesium sulfate, and then concentrated to give a residue. The residue was subjected to silica gel chromatography, which afforded 0.35 g of 3,5-dichloro-1-(3,3-dichloro-2-propenyloxy)-4-(3-(N-methyl-4-(trifluoromethyl)benzamido)propyloxy)benzene (55% yield), $n_D^{24.5}$ 1.5461.

PRODUCTION EXAMPLE 13

Production of Compound (100) by Production Process F

To a mixture of 0.35 g of 4-(3-aminopropyloxy)-3,5-dichloro-1-(3,3-dichloro-2-propenyloxy) benzene, 0.17 g of 4-chlorophenylacetic acid, 0.1 8 ml of triethylamine and 10 ml of dichloromethane was added 0.23 g of WSC hydrochloride, while stirring at room temperature. After stirring at room temperature for 6 hours, the reaction mixture was concentrated to give a residue. The residue was dissolved in 50 ml of ethyl acetate, and the ethyl acetate layer was successively washed with 10% hydrochloric acid, saturated aqueous sodium hydrogen carbonate solution and saturated saline solution, dried over anhydrous magnesium sulfate, and then concentrated to give a residue. The residue was subjected to silica gel chromatography, which afforded 0.35 g of 3,5-dichloro-1-(3,3-dichloro-2-propenyloxy)-4-(3-(4-chlorophenylacetamido )propyloxy)benzene (70% yield), m.p., 108.4° C.

PRODUCTION EXAMPLE 14

Production of Compound (127) by Production Process F

To a solution of 0.20 g of 5-(2,6-dichloro-4-(3,3-dichloro-2-propenyloxy)-phenoxy)valeric acid and 0.05 g of dipropargylamine dissolved in 10 ml of chloroform was added 0.11 g of WSC hydrochloride, while stirring at room temperature. After stirring at room temperature for 24 hours, the reaction mixture was concentrated to give a residue. The residue was subjected to silica gel chromatography, which afforded 0.21 g of 3,5-dichloro-1-(3,3-dichloro-2-propenyloxy)-4-(4-(N, N-dipropargylcarbamoyl)butyl-oxy)benzene (92% yield), $n_D^{25.0}$ 1.5481.

PRODUCTION EXAMPLE 15

Production of Compound (129) by Production Process L

A mixture of 0.33 g of 3,5-dichloro-1-(3,3-dichloro-2-propenyloxy)-4-(3-(aminopropyloxy)benzene and 10 ml of pyridine was cooled to 0° C., and 0.10 g of methyl chloroformnate was slowly added dropwise, while stirring. The reaction mixture was stirred at 0° C. for 1 hours, after which the temperature was slowly raised to room temperature, and the reaction mixture was further stirred at room temperature for 6 hours. The reaction mixture was poured into 10% hydrochloric acid, and the mixture was extracted twice with 50 ml of ethyl acetate. The ethyl acetate layers were combined, washed with water, dried over anhydrous magnesium sulfate, and then concentrated, which afforded 0.30 g of 3,5-dichloro-1-(3,3-dichloro-2-propenyloxy)-4-(3-methoxycarbonylamino)propyloxy)benzene (74% yield), $n_D^{25.5}$ 1.5421.

The following are specific examples of the present compounds with their compound numbers and physical properties, if measured.

(1)3,5-Dichloro-4-(3-benzamidopropyloxy)-1-(3,3-dichloro-2-propenyloxy)benzene $n_D^{23.0}$ 1.5860

(2)3,5-Dichloro-4-(3-(4-chlorobenzamido)propyloxy)-1-(3,3-dichloro-2-propenyloxy)benzene m.p., 95.1° C.

(3)3,5-Dichloro -4-(2-(4-trifluoromethoxybenzamido) ethoxy)-1-(3,3-dichloro-2-propenyloxy)benzene m.p., 81.0° C.

(4)3,5-Dichloro-4-(3-(4-trifluoromethoxybenzamido) propyloxy)-1-(3,3-dichloro-2-propenyloxy)benzene m.p., 93.8° C.

(5)3,5-Dichloro-4-(3-(4-fluorobenzamido)propyloxy)-1-(3,3-dichloro-2-propenyloxy)benzene $n_D^{24.5}$ 1.5800

(6)3,5-Dichloro-4-(3-(4-bromobenzamido)propyloxy)-1-(3,3-dichloro-2-propenyloxy)benzene m.p., 102.7° C.

(7)3,5-Dichloro-4-(3-(4-trifluoromethylbenzamido) propyloxy)-1-(3,3-dichloro-2-propenyloxy)benzene m.p., 93.5° C.

(8)3,5-Dichloro-4-(3-(4-ethoxybenzamido)propyloxy)-1-(3,3-dichloro-2-propenyloxy)benzene m.p., 120.6° C.

(9)3,5-Dichloro-4-(3-(4-isopropoxybenzamnido) propyloxy)-1-(3,3-dichloro-2-propenyloxy)benzene m.p., 91.8° C.

(10)3,5-Dichloro-4-(2-(4-trifluoromethylcinnamamido) ethoxy)-1-(3,3-dichloro-2-propenyloxy)benzene m.p., 109.4° C.

(11)3,5-Dichloro -4-(3-(4-trifluoromethylbenzamido) propyloxy)-1-(3,3-dichloro-2-propenyloxy)benzene m.p., 1 16.6° C.

(12)3,5-Dichloro -4-(3-(2-chlorobenzamido)propyloxy)-1-(3,3-dichloro-2-propenyloxy)benzene m.p., 70.3° C.

(13)3,5-Dichloro -4-(3-(3-chlorobenzamido)propyloxy)-1-(3,3-dichloro-2-propenyloxy)benzene m.p., 70.3° C.

(14)3,5-Dichloro-4-(3-(2,4-dichlorobenzamido) propyloxy)-1-(3,3-dichloro-2-propenyloxy)benzene m.p., 11 8.5° C.

(15)3,5-Dichloro-4-(3-(2,6-dichlorobenzamido) propyloxy )-1-(3,3-dichloro-2-propenyloxy)benzene m.p., 124.6° C.

(16)3,5-Dichloro-4-(3-(2,4,6-trichlorobenzamido) propoxy)-1-(3,3-dichloro-2-propenyloxy)benzene m.p., 126.1 ° C.

(17)3,5-Dichloro-4-(3-(2-trifluoromethylbenzamido) propoxy)-1-(3,3-dichloro-2-propenyloxy)benzene m.p., 98.9° C.

(18)3,5-Dichloro-4-(3-(3-trifluoromethylbenzamido) propoxy)-1-(3,3-dichloro-2-propenyloxy)benzene m.p., 73.5° C.

(19)3,5-Dichloro-4-(3-(3,5-bistrifluoromethylbenzamido)propoxy)-1-(3,3-dichloro-2-propenyloxy) benzene m.p., 110.4° C.

(20)3,5-Dichloro-4-(3-(4-tert-butylbenzamido) propyloxy)-1-(3,3-dichloro-2-propenyloxy)benzene m.p., 109.5° C.

(21)3,5-Dichloro-4-(3-(3,4-dichlorobenzamido) propoxy)-1-(3,3-dichloro-2-propenyloxy)benzene m.p., 85.9° C.

(22)3,5-Dichloro-4-(3-(4-nitrobenzamido)propoxy)-1-(3,3-dichloro-2-propenyloxy)benzene m.p., 136.0° C.

(23)3,5-Dichloro-4-(3-(4-cyanobenzamido)propoxy)-1-(3,3-dichloro-2-propenyloxy)benzene m.p., 111.7° C.

(24)3,5-Dichloro-4-(3-(N-(4-trifluoromethoxyphenyl) carbamoyl)propoxy)-1-(3,3-dichloro-2-propenyloxy) benzene m.p., 88.8° C.

(25)3,5-Dichloro-4-(2-(4-trifluoromethoxybenzenesulfonamido)ethoxy)-1-(3,3-dichloro-2-propenyloxy) benzene $n_D^{23.0}$ 1.5470

(26)3,5-Dichloro-4-(2-(N'-(4-trifluoromethoxyphenyl) ureido)ethoxy)-1-(3,3-dichloro-2-propenyloxy) benzene m.p., 125.4° C.

(27)3,5-Dichloro-4-(3-(N-phenylcarbamoyloxy) propoxy)-1-(3,3-dichloro-2-propenyloxy)benzene $n_D^{24.5}$ 1.5777

(28)3,5-Dichloro-4-(3-(N-(4-chlorophenyl) carbamoyloxy)propoxy)-1-(3,3-dichloro-2-propenyloxy)benzene m.p., 54.3° C.

(29)3,5-Dichloro-4-(2-(N-(4-chlorophenyl) carbamoyloxy)ethoxy)-1-(3,3-dichloro-2-propenyloxy)benzene m.p., 105.5° C.

(30)3,5-Dichloro-4-(2-(N-(4-trifluoromethoxyphenyl) carbamoyloxy)-ethoxy)-1-(3,3-dichloro-2-propenyloxy)benzene $n_D^{24.5}$ 1.5446

(31)3,5-Dichloro-4-(3-(6-chloronicotinamido)propoxy)-1-(3,3-dichloro-2-propenyloxy)benzene m.p., 85.6° C.

(32)3,5-Dichloro-4-(4-(4-trifluoromethylbenzamido) butoxy)-1-(3,3-dichloro-2-propenyloxy)benzene m.p., 90.5° C.

(33)3,5-Dichloro-4-(3-(thiophene-2-carboxamido) propoxy)-1-(3,3-dichloro-2-propenyloxy)benzene $n_D^{24.0}$ 1.6026

(34)3,5-Dichloro-4-(3-(5-bromofurane-2-carboxamido) propoxy)-1-(3,3-dichloro-2-propenyloxy)benzene $n_D^{24.0}$ 1.5918

(35)3,5-Dichloro-4-(3-(5-chloroindole-2-carboxamido) propoxy)-1-(3,3-dichloro-2-propenyloxy)benzene m.p., 153.9° C.

(36)3,5-Dichloro-4-(3-(4-clhorobenzamido)propoxy)-1-(3,3-dibromo-2-propenyloxy)benzene (37)3,5-Dibromo-4-(3-(4-chlorobenzamido)propoxy)-1-(3,3-dichloro-2-propenyloxy)benzene (38)3,5-Dimeth yl-4-(3-(4-chlorobenzamido) propoxy)-1-(3,3-dichloro-2-propenyloxy)benzene (39)3,5-Diethyl-4-(3-(4-chlorobenzamido)propoxy)-1-(3,3-dichloro-2-propenyloxy)benzene (40)3-Chloro-5-fluoro-4-(3-(4-chlorobenzamido) propoxy)-1-(3,3-dichloro-2-propenyloxy)benzene (41)3-Chloro-5-methyl-4-(3-(4chlorobenzamido) propoxy)-1-(3,3-dichloro-2-propenyloxy)benzene (42)3–Chloro-5-ethyl-4-(3-(4-chlorobenzamido) propoxy)-1-(3,3-dichloro-2-propenyloxy)benzene (43)3-Ethyl-5-methyl-4-(3-(4-chlorobenzamido) propoxy)-1-(3,3-dichloro-2-propenyloxy)benzene (44)3,5-Dichloro-4-(4-(4-chlorobenzarido)butoxy)-1-(3,3-dichloro-2-propenyloxy)benzene m.p., 96.5° C.

(45)3,5-Dichloro-4-(4-(4-chlorobenzamido)butoxy)-1-(3,3-dibromo-2-propenyloxy)benzene (46). 3,5-Dibromo-4-(4-(4-chlorobenzamido)butoxy)-1-(3,3-dichloro-2-propenyloxy)benzene (47)3,5-Dimethyl-4-(4-(4-chlorobenzamido)butoxy)-1-(3,3-dichloro-2-propenyloxy)benzene (48)3,5-Diethyl-4-(4-(4-chlorobenzamido)butoxy)-1-(3,3-dichloro-2-propenyloxy)benzene (49)3-Chloro-5-fluoro-4-(4-(4-chlorobenzamido) butoxy)-1-(3,3-dichloro-2-propenyloxy)benzene (50)3-Chloro-5-methyl-4-(4-(4-chlorobenzarmido) butoxy)-1-(3,3-dichloro-2-propenyloxy)benzene (51)3-Chloro-5-ethyl-4-(4-(4-chlorobenzamido)butoxy)-1-(3,3-dichloro-2-propenyloxy)benzene (52)3-Ethyl-5-methyl-4-(4-(4-chlorobenzamido)butoxy)-1-(3,3-dichloro-2-propenyloxy)benzene (53)3,5-Dichloro-4-(3-(4-trifluoromethylbenzamido) propoxy)-1-(3,3-dibromo-2-propenyloxy)benzene (54)3,5-Dibromo-4-(3-(4-trifluoromethylbenzamido) propoxy)-1-(3,3-dichloro-2-propenyloxy)benzene (55)3,5-Dimethyl-4-(3-(4-trifluoromethylbenzamido) propoxy)-1-(3,3-dichloro-2-propenyloxy)benzene (56)3,5-Diethyl-4-(3-(4-trifluoromethyl benzamido) propoxy)-1-(3,3-dichloro-2-propenyloxy)benzene m.p., 99.5° C.

(57)3-Chloro-5-fluoro-4-(3-(4-trifluoromethylbenzamido)propoxy)-1-(3,3-dichloro-2-propenyloxy) benzene (58)3-Chloro-5-methyl-4-(3-(4-trifluoromethylbenzamido)propoxy)-1-(3,3-dichloro-2-propenyloxy) benzene m.p., 91.0° C.

(59)3-Ethyl-5-methyl-4-(3-(4trifluoromethylbenzamido) propoxy)-1-(3,3-dichloro-2-propenyloxy)benzene m.p., 92.2° C.

(60)3,5-Dichloro-4-(4-(4-trifluoromethylbenzamido) butoxy)-1-(3,3-dibromo-2-propenyloxy)benzene (61)3,5-Dibromo-4-(4-(4-trifluoromethylbenzamido) butoxy)-1-(3,3-dichloro-2-propenyloxy)benzene (62)3,5-Dimethyl 1-4-(4-(4-trifluoromethylbenzamido) butoxy)-1-(3,3-dichloro-2-propenyloxy)benzene (63)3,5-Diethyl-4-(4-(4-trifluoromethylbenzamido) butoxy)-1-(3,3-dichloro-2-propenyloxy)benzene (64)3-Chloro-5-fluoro-4-(4-(4-trifluoromethylbenzamido)butoxy)-1-(3,3-dichloro-2-propenyloxy) benzene (65)3-Chloro-5-methyl-4-(4-(4-trifluoromethylbenzamido)butoxy)-1-(3,3-dichloro-2-propenyloxy) benzene (66)3-Ethyl-5-methyl-4-(4-(4-trifluoromethylbenzamido) butoxy)-1-(3,3-dichloro-2-propenyloxy)benzene (67)3,5-Dichloro-4-(3-(5-trifluoromethylpicolinamido) propoxy)-1-(3,3-dichloro-2-propenyloxy)benzene m.p., 55.1° C.

(68)3,5-Dichloro-4-(3-(5-trifluoromethylpicolinamido) propoxy)-1-(3,3-dibromo-2-propenyloxy)benzene (69)3,5-Dibromo-4-(3-(5-trifluoromethylpicolinamido) propoxy)-1-(3,3-dichloro-2-propenyloxy)benzene (70)3,5-Dimethyl-4-(3-(5-trifluoromethylpicolinamido) propoxy)-1-(3,3-dichloro-2-propenyloxy)benzene (71)3,5-Diethyl-4-(3-(5-trifluoromethylpicolinamido) propoxy)-1-(3,3-dichloro-2-propenyloxy)benzene (72)3–Chloro-5-fluoro-4-(3-(5-trifluoromethylpicolinamido)propoxy)-1-(3,3-dichloro-2-propenyloxy)benzene (73)3–Chloro-5-methyl-4-(3-(5-trifluoromethylpicolinamido)propoxy)-1-(3,3-dichloro-2-propenyloxy)benzene (74)3-Ethyl-5-methyl-4-(3-(5-trifluoromethylpicolinamido)propoxy)-1-(3,3-dichloro-2-propenyloxy)benzene (75)3,5-Dichloro-4-(4-(5-trifluoromethylpicolinamido) butyloxy)-1-(3,3-dichloro-2-propenyloxy)benzene (76)3,5-Dichloro-4-(4-(5-trifluoromethylpicolinamido) butyloxy)-1-(3,3-dibromo-2-propenyloxy)benzene (77)3,5-Dibromo-4-(4-(5-trifluoromethylpicolinamido) butyloxy)-1-(3,3-dichloro-2-propenyloxy)benzene (78)3,5-Dimethyl-4-(4-(5-trifluoromethylpicolinamido) butyloxy)-1-(3,3-dichloro-2-propenyloxy)benzene (79)3,5-Diethyl-4-(4-(5-trifluoromethylpicolinamido) butyloxy)-1-(3,3-dichloro-2-propenyloxy)benzene (80)3-Chloro-5-fluoro-4-(4-(5-trifluoromethylpicolinamnido)butyloxy)-1-(3,3-dichloro-2-propenyloxy)benzene (81)3-Chloro-5-methyl-4-(4-(5-trifluoromethylpicolinamido)butyloxy)-1-(3,3-dichloro-2-propenyloxy)benzene (82)3-Ethyl-5-methyl-4-(4-(5-trifluoromethylpicolinamido)butyloxy)-1-(3,3-dichloro-2-propenyloxy)benzene (83)3,5-Dichloro-1-(3,3-dichloro-2-propenyloxy)-4-(3-(5-methyl-1,4-benzodioxane-6-carboxamido)propoxy) benzene m.p., 120.8° C.

(84)3,5-Dichloro-1-(3,3-dichloro-2-propenyloxy)-4-(3-(2-pyrazinecarboxamido)propoxy)benzene $n_D^{28.0}$ 1.5825

(85)3,5-Dichloro-1-(3,3-dichloro-2-propenyloxy)-4-(3-(4-pyridazinecarboxamido)propoxy)benzene glassy (86)3,5-Dichloro-1-(3,3-dichloro-2-propenyloxy)-4-(3-(1-methyl-2-indolecarboxamido)propoxy)benzene m.p., 123.3° C.

(87)3,5-Dichloro-1-(3,3-dichloro-2-propenyloxy)-4-(3-(6,6-dimethyl-5,6-dihydro-4H-pyran-4-one-2-carboxamido)propoxy)benzene $n_D^{28.0}$ 1.5612

(88)3,5-Dichloro-1-(3,3-dichloro-2-propenyloxy)-4-(3-(4-oxo-4H-1-benzopyrane-2-carboxamido)propoxy)benzene m.p., 165.7° C.

(89)3,5-Dichloro-1-(3,3-dichloro-2-propenyloxy)-4-(3-(1-methyl-2-pyrrolecarboxamido)propoxy)benzene $n_D^{28.0}$ 1.5772

(90)3,5-Dichloro-1-(3,3-dichloro-2-propenyloxy)-4-(3-(2-quinolinecarboxamido)propoxy)benzene m.p., 145.8° C.

(91)3,5-Dichloro-1-(3,3-dichloro-2-propenyloxy)-4-(3-(5-methyl-2-pyrazinecarboxamido)propoxy)benzene m.p., 109.0° C.

(92)3,5-Dichloro-1-(3,3-dichloro-2-propenyloxy)-4-(4-(N-methyl-4-(trifluoromethyl)benzamido)butoxy)benzene $n_D^{26.0}$ 1.5417

(93)3,5-Dichloro-1-(3,3-dichloro-2-propenyloxy)-4-(3-(N-methyl-4-(trifluoromethyl)benzamido)propoxy)benzene $n_D^{24.5}$ 1.5461

(94)3,5-Dichloro-1-(3,3-dichloro-2-propenyloxy)-4-(3-(2-furancarboxamido)propoxy)benzene $n_D^{24.5}$ 1.5682

(95)3,5-Dichloro-1-(3,3-dichloro-2-propenyloxy)-4-(3-(3-furancarboxamido)propoxy)benzene $n_D^{24.5}$ 1.5695

(96)3,5-Dichloro-1-(3,3-dichloro-2-propenyloxy)-4-(3-(3-thiophenecarboxamido)propoxy)benzene $n_D^{24.5}$ 1.5824

(97)3,5-Dichloro-1-(3,3-dichloro-2-propenyloxy)-4-(3-(5-methylthiophenecarboxamido)propoxy)benzene m.p., 85.4° C.

(98)3,5-Dichloro-1-(3,3-dichloro-2-propenyloxy)-4-(3-(4-propyl benzamido)propoxy)benzene m.p., 92.9° C.

(99)3,5-Dichloro-1-(3,3-dichloro-2-propenyloxy)-4-(3-(6-methyl-$^3$-pyridinecarboxamido)propoxy)benzene m.p., 94.8° C.

(100)3,5-Dichloro-1-(3,3-dichloro-2-propenyloxy)-4-(3-(4-chlorophenylacetamido)propoxy)benzene m.p., 108.4° C.

(101)3,5-Dichloro-1-(3,3-dichloro-2-propenyloxy)-4-(3-(3-(trifluoromethyl)phenylacetamide)propoxy)benzene m.p., 88.7° C.

(102)3,5-Dichloro-1-(3,3-dichloro-2-propenyloxy)-4-(4-(N-isopropyl-4-(trifluoromethyl)benzamido)butoxy)benzene $n_D^{24.5}$ 1.5394

(103)3,5-Dichloro-1-(3,3-dichloro-2-propenyloxy)-4-(3-(N-(4-(trifluoromethyl)phenyl)carbamoyl)propoxy)benzene m.p., 112.8° C.

(104)3,5-Dichloro1-(3,3-dichloro-2-propenyloxy)-4-(4-(N-(4-(trifluoromethyl)phenyl)carbamoyl)butoxy)benzene m.p., 111.5° C.

(105)3,5-Dichloro-1-(3,3-dichloro-2-propenyloxy)-4-(3-(1-methyl-5-nitro-4-pyrazolecarboxamide)propoxy)benzene m.p., 122.2° C.

(106)3,5-Dichloro-1-(3,3-dichloro-2-propenyloxy)-4-(3-(3-quinolinecarboxamido)propoxy)benzene m.p., 115.9° C.

(107)3,5-Dichloro-1-(3,3-dichloro-2-propenyloxy)-4-(3-(5-nitro-2-furancarboxamido)propoxy)benzene $n_D^{21.0}$ 1.5850

(108)3,5-Dichloro-1-(3,3-dichloro-2-propenyloxy)-4-(3-(5-(trifluoromethyl)-2-pyridinecarboxamido)propoxy)benzene m.p., 66.8° C.

(109)3,5-Dichloro-1-(3,3-dichloro-2-propenyloxy)-4-(3-(N-(5-bromo-2-thiazole)carbamoyl)propoxy)benzene m.p., 164.0° C.

(110)3,5-Dichloro-1-(3,3-dichloro-2-propenyloxy)-4-(4-(4-chlorobenzenesulfonamido)butoxybenzene $n_D^{21.5}$ 1.5745

(111)3,5-Dichloro-1-(3,3-dichloro-2-propenyloxy)-4-(4-(5-bromo-2-furancarboxamido)butoxybenzene $n_D^{21.5}$ 1.5801

(112)3,5-Dichloro-1-(3,3-dichloro-2-propenyloxy)-4-(4-(5-methyl-2-thiophenecarboxamido)butoxybenzene m.p., 105.2° C.

(113)3,5-Dichloro-1-(3,3-dichloro-2-propenyloxy)-4-(4-(3-quinolinecarboxamido)butoxybenzene m.p., 110.1° C.

(114)3,5-Dichloro-1-(3,3-dichloro-2-propenyloxy)-4-(4-(dipropyl carbamoyl)butoxy)benzene $n_D^{26.5}$ 1.5291

(115)3,5-Dichloro-1-(3,3-dichloro-2-propenyloxy)-4-(5-(dipropylcarbamoyl)pentoxy)benzene $n_D^{24.0}$ 1.5271

(116)3,5-Dichloro-1-(3,3-dichloro-2-propenyloxy)-4-(4-(diethylcarbamoyl)butoxy)benzene $n_D^{25.0}$ 1.5386

(117)3,5-Dichloro-1-(3,3-dichloro-2-propenyloxy)-4-(3-(trifluoroacetamido)-propoxy)benzene m.p., 68.1° C.

(118)3,5-Dichloro-1-(3,3-dichloro-2-propenyloxy)-4-(3-(trifluoromethanesulfonyl)propoxy)benzene m.p., 47.2° C.

(119)3,5-Dichloro-1-(3,3-dichloro-2-propenyloxy)-4-(3-(acetamidopropoxy)-benzene m.p., 77.8° C.

(120)3,5-Dichloro-1-(3,3-dichloro-2-propenyloxy)-4-(4-(1-piperidylcarbonyl)butoxy)benzene $n_D^{24.5}$ 1.5423

(121)3,5-Dichloro-1-(3,3-dichloro-2-propenyloxy)-4-(4-(1-pyrrolidinylcarbonyl)butoxy)benzene $n_D^{24.5}$ 1.5537

(122)3,5-Dichloro-1-(3,3-dichloro-2-propenyloxy)-4-(2-(1-piperidylcarbonyl)ethoxy)benzene $n_D^{27.0}$ 1.5517

(123)3,5-Dichloro-1-(3,3-dichloro-2-propenyloxy)-4-(3-(1-piperidylcarbonyl)propoxy)benzene $n_D^{25.0}$ 1.5510

(124)3,5-Dichloro-1-(3,3-dichloro-2-propenyloxy)-4-(4-(N,N-diallylcarbamoyl)butoxy)benzene $n_D^{26.5}$ 1.5432

(125)3,5-Dichloro-1-(3,3-dichloro-2-propenyloxy)-4-(5-(1-piperidylcarbonyl)pentoxy)benzene $n_D^{24.0}$ 1.5395

(126)3,5-Dichloro-1-(3,3-dichloro-2-propenyloxy)-4-(5-(N,N-diallylcarbamoyl)pentoxy)benzene $n_D^{24.0}$ 1.5396

(127)3,5-Dichloro-1-(3,3-dichloro-2-propenyloxy)-4-(4-(N,N-dipropargylcarbamoyl)butoxy)benzene $n_D^{25.0}$ 1.5481

(128)3,5-Dichloro-1-(3,3-dichloro-2-propenyloxy)-4-(4-(4-morpholinylcarbonyl)butoxy)benzene $n_D^{25.5}$ 1.5450

(129)3,5-Dichloro-1-(3,3-dichloro-2-propenyloxy)-4-(3-(methoxycarbonylamino)propoxy)benzene $n_D^{25.5}$ 1.5421

(130)3,5-Dichloro-1-(3,3-dichloro-2-propenyloxy)-4-(4-(methoxycarbonylamino)butoxy)benzene $n_D^{24.5}$ 1.5440

(131)3,5-Dichloro-1-(3,3-dichloro-2-propenyloxy)-4-(4-(ethoxycarbonylamino)butoxy)benzene $n_D^{24.5}$ 1.5375

(132)3,5-Dichloro-1-(3,3-dichloro-2-propenyloxy)-4-(4-(propyloxycarbonylamino)butoxy)benzene $n_D^{24.5}$ 1.5339

(133)3,5-Dichloro-1-(3,3-dichloro-2-propenyloxy)-4-(3-(tert-butyramidopropoxy)benzene $n_D^{230}$ 1.5407

(134)3,5-Dichloro-1-(3,3-dichloro-2-propenyloxy)-4-(3-(2,4-bis(trifluoromethyl)benzamido)propoxy)benzene (135)3,5-Dichloro-1-(3,3-dichloro-2-propenyloxy)-4-(4-(2,4-bis(trifluoromethyl)benzamido)butyroxy)benzene (136)3,5-Dichloro-1-(3,3-dichloro-2-propenyloxy)-4-(3-(2-fluoro-4-(trifluoromethyl)benzamido)propoxy) benzene (137)3,5-Dichloro-1-(3,3-dichloro-2-propenyloxy)-4-(4-(2-fluoro-4-(trifluoromethyl)benzamido)butyroxy) benzene (138)3,5-Dichloro-1-(3,3-dichloro-2-propenyloxy)-4-(3-(2-nitro-4-(trifluoromethyl)benzamido)propoxy) benzene (139)3,5-Dichloro-1-(3,3-dichloro-2-propenyloxy)-4-(4-(2-nitro-4-(trifluoromethyl)benzamido)butyroxy) benzene (140)3,5-Dichloro-1-(3,3-dichloro-2-propenyloxy)-4-(3-(4-chloro-2-fluorobenzamido)propoxy)benzene (141)3,5-dichloro-1-(3,3-dichloro-2-propenyloxy)-4-(4-(4-chloro-2-fluorobenzamido)butyroxy)benzene (142)3,5-Dichloro-1-(3,3-dichloro-2-propenyloxy)-4-(3-(2-chloro-5-(trifluoromethyl)benzamido)propoxy) benzene (143)3,5-Dichloro-1-(3,3-dichloro-2-propenyloxy)-4-(4-(2-chloro-5-(trifluoromethyl)benzamido)butyroxy) benzene (144)3,5-Dichloro-1-(3,3-dichloro-2-propenyloxy)-4-(3-(2,5-dichlorobenzamido)propoxy)benzene (145)3,5-Dichloro-1-(3,3-dichloro-2-propenyloxy)-4-(4-(2,5-dichlorobenzamido)butyroxy)benzene (146)3,5-Diethyl-1-(3,3-dichloro-2-propenyloxy)-4-(3-(2,4-bis(trifluoromethyl)benzamido)propoxy)benzene (147)3,5-Diethyl-1-(3,3-dichloro-2-propenyloxy)-4-(3-(2-fluoro-4-(trifluoromethyl)benzamido)propoxy) benzene (148)3,5-Diethyl-1-(3,3-dichloro-2-propenyloxy)-4-(3-(4-chloro-2-fluorobenzamido)propoxy)benzene The following are production examples for the intermediates of general formula [IX].

INTERMEDIATE PRODUCTION EXAMPLE 1

Production of Intermediate Compound 1

A reaction vessel was charged with 30.5 g of 4-hydroxyphenyl benzoate, 21.6 g of potassium carbonate, 20.8 g of 1,1,3-trichloropropene and 100 ml of N,N-dimethylformamide. After stirring at room temperature for 15 hours, the reaction mixture was poured into water and extracted twice with 150 ml of diethyl ether. The ether layers were combined, washed with water, dried over anhydrous magnesium sulfate, and then concentrated to give a crude product. The crude product was subjected to silica gel chromatography, which afforded 44.1 g of 4-(3,3-dichloro-2-propenyloxy)phenyl benzoate (96% yield).

A reaction vessel was charged with 44.1 g of 4-(3,3-dichloro-2-propenyloxy)-phenyl benzoate and 400 ml of methanol, and 33 g of 30% aqueous potassium hydroxide solution was slowly added dropwise under ice cooling. After stirring for 1 hour, the mixture was made weak acidic by the addition of 10% hydrochloric acid, and then extracted twice with 150 m of diethyl ether under salting out. The ether layers were combined, washed with water, dried over anhydrous magnesium sulfate, and then concentrated to give a crude product. The crude product was subjected to silica gel chromatography, which afforded 26.0 g of 4-(3,3-dichloro-2-propenyloxy)phenol (87% yield).

A reaction vessel was charged with 26.0 g of 4-(3,3-dichloro-2-propenyloxy)phenol and 500 ml of carbon tetrachloride, and a solution of 27.1 g of t-butyl hypochlorite dissolved in 20 ml of carbon tetrachloride was slowly added dropwise, while stirring under cooling. After stirring for 24 hours, the reaction mixture was poured into water, and the organic layer (carbon tetrachloride layer) was separated. The organic layer was washed with water, dried over anhydrous magnesium sulfate, and then concentrated to give a crude product. The crude product was subjected to silica gel chromatography, which afforded 11.0 g of 2,6-dichloro-4-(3,3-dichloro-2-propenyloxy)phenol (32% yield), $n_D^{22.5}$ 1.5895.

The following are some specific examples of the intermediates of general formula [IX] with their compound numbers and physical properties, if measured.

1) 2,6-Dichloro-4-(3,3-dichloro-2-propenyloxy)phenol $^1$H-NMR ($CDCl_3$/TMS) δ (ppm): 4.57 (2H, d), 5.50 (1H, brs), 6.11 (1H, t), 6.85 (2H, s)

2) 2,6-Dichloro-4-(3,3-dibromo-2-propenyloxy)phenol 3) 2-Chloro-6-bromo-4-(3,3-dichloro-2-propenyloxy) phenol 4) 2-Chloro-6-bromo-4-(3,3-dibromo-2-propenyloxy) phenol 5) 2,6-Dibromo-4-(3,3-dichloro-2-propenyloxy)phenol 6) 2,6-Dibromo-4-(3,3-dibromo-2-propenyloxy)phenol 7)2,6-Dimethyl-4-(3,3-dichloro-2-propenyloxy)phenol 8) 2,6-Dimethyl-4-(3,3-dibromo-2-propenyloxy)phenol 9) 2-Chloro-6-methyl-4-(3,3-dichloro-2-propenyloxy) phenol 10) 2-Chloro-6-methyl-4-(3,3-dibromo-2-propenyloxy) phenol The following are production examples for the intermediates of general formula [XVIII].

INTERMEDIATE PRODUCTION EXAMPLE 2

Production of Intermediate Compound 12

A reaction vessel was charged with 10.6 g of 1,3-dibromopropane, 5.53 g of potassium carbonate and 100 ml of N,N-dimethylformamide, and a solution of 10.1 g of 2,6-dichloro-4-(3,3-dichloro-2-propenyloxy)phenol dissolved in 40 ml of N,N-dimethylformamide was slowly added dropwise. After stirring at room temperature for 24 hours, the reaction mixture was poured into water and extracted twice with 150 ml of diethyl ether. The ether layers were combined, washed with water, dried over anhydrous magnesium sulfate, and then concentrated to give a crude product. The crude product was subjected to silica gel chromatography, which afforded 11.1 g of 3,5-dichloro-4-(3-bromopropoxy)-1-(3,3-dichloro-2-propenyloxy)benzene (77% yield).

A reaction vessel was charged with 11.1 g of 3,5-dichloro-4-(3-bromopropoxy)- 1-(3,3-dichloro-2-propenyloxy) benzene, 3.31 g of benzoic acid, 3.90 g of potassium carbonate and 50 ml of N,N-dimethylformamide. After stirring at room temperature for 24 hours, the reaction mixture was poured into water and extracted twice with 150 ml of diethyl ether. The ether layers were combined, and washed with water, dried over anhydrous magnesium chloride, and then concentrated to give a crude product. The crude product was subjected to silica gel chromatography, which afforded 11.6 g of 3,5-dichloro-4-(3-benzoyloxypropyloxy)-1-(3,3-dichloro-2-propenyloxy) benzene (95% yield).

A reaction vessel was charged with 11.6 g of 3,5-dichloro-4-(3-benzoyloxypropyloxy)-1-(3,3-dichloro-2-propenyloxy)benzene, 15.2 g of 10% aqueous potassium hydroxide solution and 30 ml of methanol. After stirring at room temperature for 24 hours, the reaction mixture was concentrated. Water was poured into the concentrate, and the mixture was extracted twice with 150 ml of diethyl ether. The ether layers were combined, washed with water, dried over anhydrous magnesium sulfate, and then concentrated to give a crude product. The crude product was subjected to silica gel chromatography, which afforded 7.41 g of 3-(2,6-dichloro-4-(3,3-dichloro-2-propenyloxy)phenoxy)-1-propanol (83% yield), m.p., 56.6° C.

The following are some specific examples of the intermediates of general formula [XVIII] with their compound numbers and physical properties, if measured.

11) 2-(2,6-dichloro-4-(3,3-dichloro-2-propenyloxy)phenoxy)ethanol 12) 3-(2,6-dichloro-4-(3,3-dichloro-2-propenyloxy)phenoxy)-1-propanol m.p., 56.6° C.

13) 4-(2,6-dichloro-4-(3,3-dichloro-2-propenyloxy)phenoxy)-1-butanol 14) 5-(2,6-dichloro-4-(3,3-dichloro-2-propenyloxy)phenoxy)-1-pentanol 15) 2-(2,6-dichloro-4-(3,3-dichloro-2-propenyloxy)phenoxy)-1-ethanethiol 16) 3-(2,6-dichloro-4-(3,3-dichloro-2-propenyloxy)phenoxy)-1-propanethiol 17) 4-(2,6-dichloro-4-(3,3-dichloro-2-propenyloxy)phenoxy)-1-butanethiol 18) 5-(2,6-dichloro-4-(3,3-dichloro-2-propenyloxy)phenoxy)-1-pentanethiol The following are production examples for the intermediates of general formula [III] or [XII].

INTERMEDIATE PRODUCTION EXAMPLE 3

Production of Intermediate Compound 21

A reaction vessel was charged with 4.09 g of 3,5-dichloro-4-(3-bromopropyloxy)-1-(3,3-dichloro-2-propenyloxy)benzene, 2.41 of potassium phthalimide and 30 ml of N,N-dimethylformamide. After stirring at room temperature for 24 hours, the reaction mixture was poured into water and extracted twice with 150 ml of chloroform. The chloroform layers were combined, washed with diluted hydrochloric acid and diluted aqueous sodium hydroxide, dried over anhydrous magnesium sulfate, and then concen- trated, which afforded 4.67 g of crude 3,5-dichloro-4-(3-phthalimidopropyloxy)-1-(3,3-dichloro-2-propenyloxy)benzene (98% yield).

A reaction vessel was charged with 4.67 g of crude 3,5-dichloro-4-(3-phthalimidopropyloxy)-1-(3,3-dichloro-2-propenyloxy)benzene, 0.55 g of hydrazine monohydrate and 200 ml of ethanol. After heating under reflux for 2 hours, the reaction mixture was made weak acidic by the addition of concentrated hydrochloric acid, and then further heated under reflux for I hours. The deposited solid was collected by filtration, and the filtrate was concentrated. Water was poured into the concentrated, and the mixture was extracted twice with 150 ml of chloroform. The chloroform layers were combined, washed with water, dried over anhydrous magnesium sulfate, and then concentrated to give a crude product. The crude product was subjected to silica gel chromatography which afforded 2.4 of 3,5-dichloro-4-(3-aminopropyloxy)-1-(3,3-dichloro-2-propenyloxy)benzene (71% yield), $n_D^{23.5}$ 1.5672.

INTERMEDIATE PRODUCTION EXAMPLE 4

Production of Intermediate Compound 23

A mixture of 9.1 g of 2,6-dichloro-4-(3,3-dichloro-2-propenyloxy)phenol, 8.9 g of N-(4-bromoethyl)phthalimide, 4.4 g of potassium carbonate and 100 ml of N,N-dimethylformamide was stirred at room temperature for 24 hours. The reaction mixture was poured into ice water and made weak acidic by the addition of 10% hydrochloric acid, after which 200 ml of ethyl acetate was added for extraction. The ethyl acetate layer was successively washed with 10% hydrochloric acid and saturated saline solution, dried over anhydrous magnesium sulfate, and then concentrated to give crude crystals. The crude crystals were washed with n-hexane and then dried under reduced pressure, which afforded 14.5 g of 3,5-dichloro-4-(4-phthalimidobutyloxy)-1-(3,3-dichloro-2-propenyloxy)benzene (94% yield).

A mixture of 14.5 g of 3,5-dichloro-4-(4-phthalimidobutyloxy)-1-(3,3-dichloro-2-propenyloxy)benzene, 1.73 ml of hydrazine monohydrate and 100 ml of ethanol was heated under reflux for 4 hours. The reaction mixture was made weak acidic by the addition of concentrated hydrochloric acid and further heated under reflux for 1 hour. The temperature of the reaction mixture was decreased to room temperature, after which the deposited solid was collected by filtration and the filtrate was concentrated to give a residue. To the residue was added a solution of 2.1 g of potassium hydroxide dissolved in 100 ml of ethanol, after which the deposited solid was collected by filtration and the filtrate was concentrated to give a residue. To the residue was added 100 ml of diethyl ether for dissolution, and the solution was dried over anhydrous magnesium sulfate and then concentrated, which afforded 7.51 g of 3,5-dichloro-4-(4-aminobutyloxy)-1-(3,3-dichloro-2-propenyloxy)benzene (71% yield), $n_D^{23.5}$ 1.5672.

INTERMEDIATE PRODUCTION EXAMPLE 5

Production of Intermediate Compound 60

A mixture of 1.0 g of 3,5-dichloro-1-(3,3-dichloro-2-propenyloxy)-4-(4-bromobutyloxy)benzene, 4 ml of 40% methanol solution of methylamine, 0.33 g of potassium carbonate and N,N-dimethylformamide was stirred at room temperature for 24 hours. To the reaction mixture was added 100 ml of saturated aqueous sodium hydrogen carbonate solution, and the mixture was extracted with 100 ml of ethyl acetate. The ethyl acetate layer was successively washed with 100 ml of saturated sodium hydrogen carbonate and saturated saline solution, dried over anhydrous magnesium sulfate, and then concentrated, which afforded 0.80 g of 3,5-dichloro-1-(3,3-dichloro-2-propenyloxy)-4-(4-(methylamino)butyloxy)benzene (89% yield), $n_D^{26.0}$ 1.5545.

The following are some specific examples of the intermediates of general formula [III] or [XII] with their compound numbers and physical properties, if measured.

19) 3,5-Dichloro-4-(2-aminoethoxy)-1-(3,3-dichloro-2-propenyloxy)benzene $n_D^{25.0}$ 1.5784

20) 3,5-Dichloro-4-(2-aminoethoxy)-1-(3,3-dibromo-2-propenyloxy)benzene 21) 3,5-Dichloro-4-(3-aminopropyloxy)-1-(3,3-dichloro-2-propenyloxy)benzene $n_D^{23.5}$ 1.5672

22) 3,5-Dichloro-4-(3-aminopropyloxy)-1-(3,3-dibromo-2-propenyloxy)- benzene 23) 3,5-Dichloro-4-(4-aminobutyloxy)-1-(3,3-dichloro-2-propenyloxy)benzene $n_D^{24.5}$ 1.5722

24) 3,5-Dichloro-4-(4-aminobutyloxy)-1-(3,3-dibromo-2-propenyloxy)benzene 25) 3,5-Dichloro-4-(5-aminopentyloxy)-1-(3,3-dichloro-2-propenyloxy)benzene 26) 3,5-Dichloro-4-(5-aminopentyloxy)-1-(3,3-dibromo-2-propenyloxy)benzene 27) 3,5-Dibromo-4-(2-aminoethoxy)-1-(3,3-dichloro-2-propenyloxy)benzene 28) 3,5-Dibromo-4-(2-aminoethoxy)-1-(3,3-dibromo-2-propenyloxy)benzene 29) 3,5-Dibromo-4-(3-aminopropyloxy)-1-(3,3-dichloro-2-propenyloxy)benzene 30) 3,5-Dibromo-4-(3-aminopropyloxy)-1-(3,3-dibromo-2-propenyloxy)benzene 31) 3,5-Dibromo-4-(4-aminobutyloxy)-1-(3,3-dichloro-2-propenyloxy)benzene 32) 3,5-Dibromo-4-(4aminobutyloxy)-1-(3,3-dibromo-2-propenyloxy)benzene 33) 3,5-Dibromo-4-(5-aminopentyloxy)-1-(3,3-dichloro-2-propenyloxy)benzene 34) 3,5-Dibromo-4-(5-aminopentyloxy)-1-(3,3-dibromo-2-propenyloxy)benzene 35) 3,5-Dimethyl-4-(2-aminoethoxy)-1-(3,3-dichloro-2-propenyloxy)benzene 36) 3,5-Dimethyl-4-(2-aminoethoxy)-1-(3,3-dibromo-2-propenyloxy)benzene 37) 3,5-Dimethyl-4-(3-aminopropyloxy)-1-(3,3-dichloro-2-propenyloxy)benzene 38)3,5-Dimethyl-4-(3-aminopropyloxy)-1-(3,3-dibromo-2-propenyloxy)benzene 39) 3,5-Dimethyl-4-(4-aminobutyloxy)-1-(3,3-dichloro-2-propenyloxy)benzene 40) 3,5-Dimethyl-4(4-aminobutyloxy)-1-(3,3-dibromo-2-propenyloxy)benzene 41) 3,5-Dimethyl-4-(5-aminopentyloxy)-1-(3,3-dichloro-2-propenyloxy)benzene 42) 3,5-Dimethyl-4-(5-aminopentyloxy)-1-(3,3-dibromo-2-propenyloxy)benzene 43) 3-Chloro-5-methyl-4-(2-aminoethoxy)-1-(3,3-dichloro-2-propenyloxy)benzene 44) 3–Chloro-5-methyl-4-(2-aminoethoxy)-1-(3,3-dibromo-2-propenyloxy)benzene 45) 3-Chloro-5-methyl-4-(3-aminopropyloxy)-1-(3,3-dichloro-2-propenyloxy)benzene 46) 3-Chloro-5-methyl-4-(3-aminopropyloxy)-1-(3,3-dibromo-2-propenyloxy)benzene 47) 3–Chloro-5-methyl-4-(4-aminobutyloxy)-1-(3,3-dichloro-2-propenyloxy)benzene 48) 3-Chloro-5-methyl-4-(4-aminobutyloxy)-1-(3,3-dibromo-2-propenyloxy)benzene 49) 3-Chloro-5-methyl-4-(5-aminopentyloxy)-1-(3,3-dichloro-2-propenyloxy)benzene 50) 3-Chloro-5-methyl-4-(5-aminopentyloxy)-1-(3,3-dibromo-2-propenyloxy)benzene 51) 3-Ethyl-5-methyl-4-(2-aminoethoxy)-1-(3,3-dichloro-2-propenyloxy)benzene 52) 3-Ethyl-5-methyl-4-(2-aminoethoxy)-1-(3,3-dibromo-2-propenyloxy)benzene 53) 3-Ethyl-5-methyl-4-(3-aminopropyloxy)-1-(3,3-dichloro-2-propenyloxy)benzene 54) 3-Ethyl-5-methyl-4-(3-aminopropyloxy)-1-(3,3-dibromo-2-propenyloxy)benzene 55) 3-Ethyl-5-methyl-4-(4-aminobutyloxy)-1-(3,3-dichloro-2-propenyloxy)benzene 56) 3-Ethyl-5-methyl-4-(4-aminobutyloxyl 1-(3,3-dibromo-2-propenyloxy)benzene 57) 3-Ethyl-5-methyl-4-(5-aminopentyloxy)-1-(3,3-dichloro-2-propenyloxy)benzene 58) 3-Ethyl-5-methyl-4-(5-aminopentyloxy)-1-(3,3-dibromo-2-propenyloxy)benzene 59) 3,5-Dichloro-1-(3,3-dichloro-2-propenyloxy)-4-(3-(methylamino)propyloxy)benzene $n_D^{26.0}$ 1.5618

60) 3,5-Dichloro-1-(3,3-dichloro-2-propenyloxy)-4-(4-(methylamino)butyloxy)benzene $n_D^{26.0}$ 1.5545

61) 3,5-Dichloro-1-(3,3-dichloro-2-propenyloxy)-4-(4-(isopropylamino)butyloxy)benzene $n_D^{24.5}$ 1.5355

The following are production examples for the intermediates of general formula [III] or [XII].

INTERMEDIATE PRODUCTION EXAMPLE 6

Production of Intermediate Compound 62

A reaction vessel was charged with 2.02 g of 2,6-dichloro-4-(3,3-dichloro-2-propenyloxy)phenol, 1.56 g of ethyl 3-bromobutyrate, 1.11 g of potassium carbonate and 20 ml of N,N-dimethylformamide. After stirring at room temperature for 12 hours, the reaction mixture was poured into water and extracted twice with 50 ml of diethyl ether. The ether layers were combined, washed with water, dried over anhydrous magnesium sulfate, and then concentrated to give a crude product. The crude product was subjected to silica gel chromatography, which afforded 2.54 g of ethyl 2,6-dichloro-4-(3,3-dichloro-2-propenyloxy)phenoxybutyrate (90% yield).

A reaction vessel was charged with 2.54 g of ethyl 2,6-dichloro-4-(3,3-dichloro-2-propenyloxy) phenoxybutyrate, 4.0 g of 10% aqueous potassium hydroxide solution and 50 ml of methanol. After stirring at room temperature for 24 hours, the reaction mixture was concentrated. Then, 50 ml of diethyl ether was poured into the reaction mixture, and the mixture was extracted twice with 50 ml of 5% aqueous sodium hydrogen carbonate solution. The aqueous layers were combined, and made weak acidic by the addition of concentrated hydrochloric acid. The deposited crystals were extracted twice with 50 ml of diethyl ether. The ether layers were combined, washed with water, dried over anhydrous magnesium sulfate, and then concentrated, which afforded 2.11 g of 4-(2,6-dichloro-4-(3,3-dichloro-2-propenyloxy)phenoxy)butyric acid (90% yield), m.p., 80.9° C.

The following are some specific examples of the intermediates of general formula [III] or [XIV] with their compound number and physical properties, if measured.

62) 4-(2,6-Dichloro-4-(3,3-dichloro-2-propenyloxy) phenoxy)butyric acid m.p., 80.9° C.

63) 4-(2,6-Dichloro-4-(3,3dibromo-2propenyloxy) phenoxy)butyric acid 64) 5-(2,6-Dichloro-4-(3,3-dichloro-2-propenyloxy) phenoxy)valeric acid m.p., 75.7° C.

65) 5-(2,6-Dichloro-4-(3,3-dibromo-2-propenyloxy) phenoxy)valeric acid 66) 4-(2,6-Dibromo-4-(3,3-dichloro-2-propenyloxy) phenoxy)butyric acid 67) 4-(2,6-Dibromo-4-(3,3-dibromo-2-propenyloxy) phenoxy)butyric acid 68) 5-(2,6-Dibromo-4-(3,3-dichloro-2-propenyloxy)phenoxy)valeric acid 69) 5-(2,6-Dibromo-4-(3,3-dibromo-2-propenyloxy)phenoxy)valeric acid 70) 4-(2,6-Dimethyl-4-(3,3-dichloro-2-propenyloxy)phenoxy)butyric acid 71) 4-(2,6-Dimethyl-4-(3,3-dibromo-2-propenyloxy)phenoxy)butyric acid 72) 5-(2,6-Dimethyl-4-(3,3-dichloro-2-propenyloxy)phenoxy)valeric acid 73) 5-(2,6-Dimethyl-4-(3,3-dibromo-2-propenyloxy)phenoxy)valeric acid 74) 4-(2-Chloro-6-methyl-4-(3,3-dichloro-2-propenyloxy)phenoxy)butyric acid 75) 4-(2–Chloro-6-methyl-4-(3,3-dibromo-2-propenyloxy)phenoxy)butyric acid 76) 5-(2–Chloro-6-methyl-4-(3,3-dichloro-2-propenyloxy)phenoxy)valeric acid 77) 5-(2–Chloro-6-methyl-4-(3,3-dibromo-2-propenyloxy)phenoxy)valeric acid 78) 4-(2-Ethyl-6-methyl-4-(3,3-dichloro-2-propenyloxy)phenoxy)butyric acid 79) 4-(2-Ethyl-6-methyl-4-(3,3-dibromo-2-propenyloxy)phenoxy)butyric acid 80) 5-(2-Ethyl-6-methyl-4-(3,3-dichloro-2-propenyloxy)phenoxy)valeric acid 81) 5-(2-Ethyl-6-methyl-4-(3,3-dibromo-2-propenyloxy)phenoxy)valeric acid The following are production examples for the intermediates of general formula [IV] or [V].

INTERMEDIATE PRODUCTION EXAMPLE 7

Production of Intermediate Compound 84

A reaction vessel was charged with 7.51 g of 3-amino-1-propanol, 2.53 g of triethylamine and 50 ml of dichloromethane, and 5.21 g of 4-trifluoromethylbenzoyl chloride was slowly added dropwise under ice cooling. After stirring at room temperature for 6 hours, the reaction mixture was successively washed with diluted hydrochloric acid and water, dried over anhydrous magnesium sulfate, and then concentrated, which afforded 5.25 g of 3-(4-trifluoromethylbenzamido)propan-1-ol (85% yield).

A reaction vessel was charged with 5.25 g (21.2 mmol) of 3-(4-(trifluoromethyl)benzamido)propan-1-ol, 5.72 g (21.2 mmol) of 4-benzyloxy-2,6-dichlorophenol, 5.29 g (20.2 mmol) of triphenylphosphine and 100 ml of tetrahydrofuran, and a solution of 4.08 g (20.2 mmol) of diisopropyl azodicarboxylate dissolved in 20 ml of tetrahydrofuran was added dropwise, while stirring. After stirring at room temperature for 12 hours, the reaction mixture was concentrated, and the residue was subjected to silica gel chromatography, which afforded 1-benzyloxy-3,5-dichloro-4-(3-(4-trifluoromethylbenzamido)propyloxy)benzene.

1-Benzyloxy-3,5-dichloro-4-(3-(4-trifluoromethylbenzamido)propyloxy)benzene was dissolved in ethyl acetate, which was put into a reaction vessel, and the air in the vessel was replaced with nitrogen gas. A catalytic amount of 10% palladium on carbon was added, and the nitrogen gas in the vessel was replaced with hydrogen gas, followed by vigorous stirring at room temperature for 24 hours. The hydrogen gas in the vessel was replaced with nitrogen gas, after which the reaction mixture was filtered through cerite and the filtrate was concentrated to give 3,5-dichloro-4-(3-(4-trifluoromethylbenzamido)propyloxy)phenol.

INTERMEDIATE PRODUCTION EXAMPLE 8

Production of Intermediate Compound 120

To a mixture of 27 g of 2-ethyl-6-methylaniline, 36 ml of concentrated sulfuric acid and 100 ml of water was added dropwise a solution of 16.1 g of sodium nitrite dissolved in 50 ml of water, while stirring at a temperature of 0° to 5° C. After completion of the dropwise addition, 150 g of chilled water, 1.5 g of urea and 150 g of ice were added.

This aqueous solution was added dropwise to a mixture of 100 ml of sulfuric acid, 100 ml of water and 150 g of sodium sulfate as a solution which was heating at 135° C. under stirring. Upon the dropwise addition, steam distillation was carried out. After completion of the dropwise addition, an aqueous solution obtained by the steam distillation was subjected to salting out with sodium chloride, dried over anhydrous magnesium sulfate, and then concentrated to give a crude product. The crude product was subjected to silica gel chromatography, which afforded 16 g of 2-ethyl-6-methylphenol (59% yield).

Then, 16 g of 2-ethyl-6-methylphenol was dissolved in 200 ml of chloroform, which was stirred at 0° C., and 56.6 g of tetrabutylammonium tribromide was added in small portions to this solution. After stirring at room temperature for 1 hour, the solvent was distilled out under reduced pressure. The residue was dissolved in 300 ml of diethyl ether, successively washed with 10% hydrochloric acid and water, dried over anhydrous magnesium sulfate, and then concentrated to give a crude product. The crude product was subjected to silica gel chromatography, which afforded 23 g of 4-bromo-2- ethyl-6-methylphenol (92% yield).

To a mixture of 26 g of 4-bromo-2-ethyl-6-methylphenol, 24.8 g of benzyl bromide and 200 ml of N,N-dimethylformamide was added 21.7 g of potassium carbonate, while stirring at room temperature. After stirring at room temperature for 24 hours, the reaction mixture was poured into ice water, and extracted twice with 500 ml of diethyl ether. The diethyl ether layers were combined, washed with water, dried over anhydrous magnesium sulfate, and then concentrated to give a crude product. The crude product was subjected to silica gel chromatography, which afforded 35.6 g of 4-bromo-2-ethyl-6-methyl-1-benzyloxybenzene (97% yield).

Then, 35.6 g of 4-bromo-2-ethyl-6-methyl-1-benzyloxybenzene was dissolved in 250 ml of tetrahydrofuran, and 69 ml of n-butyl lithium solution (in hexane; 1.69 mol/liter), while stirring at-70° C. After further stirring at 70° C. for 2 hours, a solution of 12.1 g of trimethoxyboron dissolved in 50 ml of tetrahydrofuran was added dropwise to the reaction mixture. After completion of the dropwise addition, the reaction mixture was returned to room temperature, stirred for 1 hour, and then poured into ice water. The mixture was made weak acidic by the addition of 10% hydrochloric acid, and extracted twice with 500 ml of diethyl ether. The ether layers was combined, washed with water, dried over anhydrous magnesium sulfate, and then concentrated to give a residue. To the residue was added 120 ml of toluene, and 33 ml of 30% aqueous hydrogen peroxide was added dropwise, while heating at 70° C. under stirring. After heating under reflux for 1 hours, the reaction mixture was returned to room temperature, washed once with water, twice with 10% aqueous ferrous ammonium sulfate and then once with water. The toluene layer was dried over anhydrous magnesium sulfate, and then concentrated to give a crude product. The crude product was subjected to silica gel chromatography, which afforded 26.2 g of 3-ethyl-4-benzyloxy-5-methylphenol (93% yield).

To a mixture of 6.3 g of 4-benzyloxy-3-ethyl-5-methylphenol, 3.2 g of triethylamine and 50 ml of chloroform was added dropwise 4.0 g of benzoyl chloride, while stirring at 0° C. After stirring at room temperature for 6 hours, the reaction mixture was concentrated under reduced pressure to give a residue. To the residue was added 100 ml of 10% hydrochloric acid, and the mixture was extracted with 100 ml of ethyl acetate. The ethyl acetate layer was successively washed 10% hydrochloric acid, saturated aqueous sodium hydrogen carbonate solution and saturated saline solution, dried over anhydrous magnesium sulfate, and then concentrated under reduced pressure, which afforded 8.4 g of crude 4-benzyloxy-3-ethyl-5-methylphenyl benzoate (93% yield).

Then, 8.4 g of crude 4-benzyloxy-3-ethyl-5-methylphenyl benzoate was 5 dissolved in 100 ml of ethyl acetate, which was put into a reaction vessel, and the air in the vessel was replaced with nitrogen gas. Then, 0.5 g of 10% palladium on carbon was added, and the nitrogen gas in the vessel was replaced with hydrogen gas, followed by vigorous stirring at room temperature for 24 hours. The hydrogen gas in the vessel was replaced with nitrogen gas, after which the reaction mixture was filtered through cerite and the filtrate was concentrated under reduced pressure, which afforded 5.9 g of crude 3-ethyl-4-hydroxy-5-methylphenyl benzoate (95% yield).

To a mixture of 0.5 g of crude 3-ethyl-4-hydroxy-5-methylphenyl benzoate, 0.48 g of 3-(4-(trifluoromethyl) benzamido)propan-1-ol, 0.54 g of triphenylphosphine and 10 ml of tetrahydrofuran was added dropwise a solution of 0.41 g of diisopropyl azodicarboxylate dissolved in 2 ml of tetrahydrofuran, while stirring at room temperature. After stirring at room temperature for 24 hours, the reaction mixture was concentrated under reduced pressure to give a residue. The residue was subjected to silica gel chromatography, which afforded 0.87 g of 3-ethyl-5-methyl-4-(3-(4-(trifluromethyl)benzamido)-propyloxyphenyl benzoate (90% yield).

To a mixture of 0.87 g of 3-ethyl-5-methyl-4-(3-(4-(trifluoromethyl)benzamido)propyloxyphenyl benzoate and 10 ml of methanol was added a mixture of 0.16 g of sodium hydroxide and 2 m of water, while stirring at 0° C. After stirring at room temperature for 24 hours, the reaction mixture was made weak acidic by the addition of 10% hydrochloric acid, and extracted with 50 ml of ethyl acetate. The ethyl acetate layer was washed with saturated saline solution, dried over anhydrous magnesium sulfate, and then concentrated under reduced pressure to give a residue. The residue was subjected to silica gel chromatography, which afforded 0.66 g of 3-ethyl-5-methyl-4-(3-(4-(trifluoromethyl)benzamido)propyloxyphenol (94% yield).

The following are some specific examples of the intermediates of general formula [IV] or [V] with their compound numbers and physical properties, if measured.

82) 3,5-Dichloro-4-(3-benzamidopropyloxy)phenol 83) 3,5-Dichloro-4-(3-(4-chlorobenzamido)propyloxy) phenol 84) 3,5-Dichloro-4-(3-(4trifluoromethylbenzamido) propyloxy)phenol 85) 3,5-Dichloro-4-(3-(4-trifluoromethoxybenzamido) propyloxy)phenol 86) 3,5-Dichloro-4-(4-benzamidobutyloxy)phenol 87) 3,5-Dichloro-4-(4-(4-chlorobenzamido)butyloxy) phenol 88) 3,5-Dichloro-4-(4-(4-trifluoromethylbenzamido) butyloxy)phenol 89) 3,5-Dichloro-4-(4-(4-trifluoromethoxybenzamido) butyloxy)phenol 90) 3,5-Dichloro-4-(3-(5-trifluoromethylpicolinamido) propyloxy)phenol 91) 3,5-Dichloro-4-(4-(5-trifluoromethylpicolinamido) butyloxy)phenol 92) 3,5-Dichloro-4-(3-(4-trifluoromethylbenzene-sulfonamido)propyloxy)-phenol 93) 3,5-Dichloro-4-(4-(4-trifluoromethylbenzene-sulfonamido)butyloxy)-phenol 94) 3,5-Dichloro-4-(3-(5-trifluoromethylpyridin-2-sulfonamido)propoxy-)phenol 95) 3,5-Dichloro-4-(4-(5-trifluoromethylpyridin-2-sulfonamido)butyloxy)-phenol 96) 3,5-Dichloro-4-(3-(N-(4-trifluoromethylphenyl) carbamoyl)propyloxy)-phenol 97)-3,5-Dichloro-4-(4-(N-(4-trifluoromethylphenyl )carbamoyl)butyloxy)-phenol 98) 3,5-Dichloro-4-(3-(N-(5-trifluoromethyl-2-pyridyl) carbamoyl)propyl-oxy)-phenol 99) 3,5-Dichloro-4-(4-(N-(5-trifluoromethyl-2-pyridyl) carbamoyl)butyl-oxy)phenol 100) 3-Chloro-5-methyl-4-(3-benzamidopropyloxy) phenol 101) 3-Chloro-5-methyl-4-(3-(4-chlorobenzamido) propyloxy)phenol 102) 3-Chloro-5-methyl-4-(3-(4-trifluoromethylbenz-amido)propyloxy)phenol 103) 3-Chloro-5-methyl-4-(3-(4-trifluoromethoxybenz-amido)propyloxy)phenol 104) 3-Chloro-5-methyl-4-(4-benzamidobutyloxy)phenol 105) 3-Chloro-5-methyl-4-(4-(4-chlorobenzamido) butyloxy)phenol 106) 3-Chloro-5-methyl-4-(4-(4-trifluoromethylbenz-amido)butyloxy)phenol 107) 3-Chloro-5-methyl-4-(4-(4-trifluoromethoxybenz-amido)butyloxy)phenol 108) 3-Chloro-5-methyl-4-(3-(5-trifluoromethylpicolin-amido)propyloxy)-phenol 109) 3-Chloro-5-methyl-4-(4-(5-trifluoromethylpicolin-amido)butyloxy)phenol 110) 3-Chloro-5-methyl-4-(3-(4-trifluoromethylbenzene-sulfonamido)propyloxy)phenol 111) 3-Chloro-5-methyl-4-(4-(4-trifluoromethylbenzene-sulfonamido)butyloxy)phenol 112) 3-Chloro-5-methyl-4-(3-(5-trifluoromethylpyridine-2-sulfonamido)propyloxy)phenol 113) 3-Chloro-5-methyl-4-(4-(5-trifluoromethylpyridine-2-sulfonamido)-butyloxy)phenol 114) 3-Chloro-5-methyl-4-(3-(N-(4-trifluoromethyl-phenyl)carbamoyl)propyloxy)phenol 115) 3-Chloro-5-methyl-4-(4-(N-(4-trifluoromethyl-phenyl)carbamoyl)butyloxy)phenol 116) 3-Chloro-5-methyl-4-(3-(N-(5-trifluoromethyl-2-pyridyl)carbamoyl)-propyloxy)phenol 117) 3-Chloro-5-methyl-4-(4-(N-(5-trifluoromethyl-2-pyridyl)carbamoyl)-butyloxy)phenol 118) 3-Ethyl-5-methyl-4-(3-benzamidopropyloxy)phenol 119) 3-Ethyl-5-methyl-4-(3-(4-chlorobenzamido)propyloxy)phenol 120) 3-Ethyl-5-methyl-4-(3-(4-trifluoromethylbenzamido)propyloxy)phenol 121) 3-Ethyl-5-methyl-4-(3-(4-trifluoromethoxybenzamido)propyloxy)phenol 122) 3-Ethyl-5-methyl-4-(4-benzamidobutyloxy)phenol 123) 3-Ethyl-5-methyl-4-(4-(4-chlorobenzamido)butyloxy)phenol 124) 3-Ethyl-5-methyl-4-(4-(4-trifluoromethylbenzamido)butyloxy)phenol 125) 3-Ethyl-5-methyl-4-(4-(4-trifluoromethoxybenzamido)butyloxy)phenol 126) 3-Ethyl-5-methyl-4-(3-(5-trifluoromethylpicolinamido)propyloxy)phenol 127) 3-Ethyl-5-methyl-4-(4-(5-trifluoromethylpicolinamido)butyloxy)phenol 128) 3-Ethyl-5-methyl-4-(3-(4-trifluoromethylbenzenesulfonamido)propyloxy)phenol 129) 3-Ethyl-S-methyl-4-(4-(4-trifluoromethylbenzenesulfonamido)butyloxy)phenol 130) 3-Ethyl-5-methyl-4-(3-(5-trifluoromethylpyridine-2-sulfonamido)propyloxy)phenol 131) 3-Ethyl-5-methyl-4-(4-(5-trifluoromethylpyridine-2-sulfonamido)butyloxy)phenol 132) 3-Ethyl-5-methyl-4-(3-(N-(4-trifluoromethylphenyl)carbamoyl)propyloxy)phenol 133) 3-Ethyl-5-methyl-4-(4-(N-(4-trifluoromethyl phenyl)carbamoyl)butyloxy)phenol 134) 3-Ethyl-5-methyl-4-(3-(N-(S-trifluoromethyl-2-pyridyl)carbamoyl)propyloxy)phenol 135) 3-Ethyl-5-methyl-4-(4-(N-(5-trifluoromethyl-2-pyridyl)carbamoyl)propyloxy)phenol 136) 3,5-Dichloro-4-(3-(2-furancarboxamido)propyloxy)phenol 137) 3,5-Dichloro-4-(3-(2-furancarboxamido)butyloxy)phenol 138) 3,5-Dichloro-4-(3-(3-furancarboxamido)propyloxy)phenol 139) 3,5-Dichloro-4-(4-(3-furancarboxamido)butyloxy)phenol 140) 3,5-Dichloro-4-(3-(5-bromo-2-furancarboxamido)propyloxy)phenol 141) 3,5-Dichloro-4-(4-(5-bromo-2-furancarboxamido)butyloxy)phenol 142) 3,5-Dichloro-4-(3-(2-thiophenecarboxamido)propyloxy)phenol 143) 3,5-Dichloro-4-(4-(2-thiophenecarboxamido)butyloxy)phenol 144) 3,5-Dichloro-4-(3-(3-thiophenecarboxamido)propyloxy)phenol 145) 3,5-Dichloro-4-(4-(3-thiophenecarboxamido)butyloxy)phenol 146) 3,5-Dichloro-4-(3-(5-methyl-2-thiophenecarboxamido)butyloxy)phenol 147) 3,5-Dichloro-4-(4-(5-methyl-2-thiophenecarboxamido)butyloxy)phenol 148) 3,5-Dichloro-4-(3-(2-pyrazinecarboxamido)propyloxy)phenol 149) 3,5-Dichloro-4-(4-(2-pyrazinecarboxamido)butyloxy)phenol 150) 3,5-Dichloro-4-(3-(1-methyl-2-indolecarboxamido)propyloxy)phenol 151) 3,5-Dichloro-4-(4-(1-methyl-2-indolecarboxamido)butyloxy)phenol 152) 3,5-Dichloro-4-(3-(1-methyl-2-pyrrolecarboxamido)propyloxy)phenol 153) 3,5-Dichloro-4-(4-(1-methyl-2-indolecarboxamido)butyloxy)phenol 154) 3,5-Dichloro-4-(3-(2-quinolinecarboxamido)propyloxy)phenol 155) 3,5-Dichloro-4-(4-(2-quinolinecarboxamido)butyloxy)phenol 156) 3,5-Dichloro-4-(3-(5-methyl-2-pyrazinecarboxamido)propyloxy)phenol 157) 3,5-Dichloro-4-(4-(5-methyl-2-pyrazinecarboxamido)butyloxy)phenol The following are formulation examples in which "parts" are by weight and the present compounds are designated by their compound numbers as described above.

FORMULATION EXAMPLE 1

Emulsifiable Concentrates

Ten parts of each of the present compounds (1) to (148) are dissolved in 35 parts of xylene and 35 parts of N,N-dimethylformamide, to which 14 parts of polyoxyethylene styrylphenyl ether and 6 parts of calcium dodecylbenzenesulfonate are added, and the mixture is well stirred to give a 10% emulsifiable concentrate of each compound.

FORMULATION EXAMPLE 2

Wettable Powders

Twenty parts of each of the present compounds (1) to (148) are added to a mixture of 4 parts of sodium lauryl sulfate, 2 parts of calcium lignin sulfonate, 20 parts of synthetic hydrated silicon oxide fine powder and 54 parts of diatomaceous earth, and the mixture is stirred with a mixer to give a 20% wettable powder of each compound.

FORMULATION EXAMPLE 3

Granules

Five parts of each of the present compounds (1) to (148), 5 parts of synthetic hydrated silicon oxide fine powder, 5 parts of sodium dodecylbenzenesulfonate, 30 parts of bentonite and 55 parts of clay are mixed, and the mixture is well stirred. Then, a suitable amount of water is added to the mixture, which is further stirred, granulated with a granulator and then air-dried to give a 5% granule of each compound.

FORMULATION EXAMPLE 4

Dusts

One part of each of the present compounds (1) to (148) is dissolved in a suitable amount of acetone, to which 5 parts of synthetic hydrated silicon oxide fine powder, 0.3 part of PAP and 93.7 parts of clay are added, and the mixture is stirred with a mixer. The removal of acetone by evaporation gives a 1% dust of each compound.

FORMULATION EXAMPLE 5

Flowables

Twenty parts of each of the present compounds (1) to (148) are mixed with 1.5 parts of sorbitan trioleate and 28.5 parts of an aqueous solution containing 2 parts of polyvinyl alcohol, and the mixture is pulverized into fine particles having a particle size of not more than 3 μm with a sand grinder, to which 40 parts of an aqueous solution containing 0.05 part of xanthan gum and 0.1 part of aluminum magnesium silicate are added and then 10 parts of propylene glycol are added. The mixture is stirred to give a 20% water-based suspension of each compound.

FORMULATION EXAMPLE 6

Oil Sprays

First, 0.1 part of each of the present compounds (1) to (148) is dissolved in 5 parts of xylene and 5 parts of trichloroethane. Then, the solution was mixed with 89.9 parts of deodorized kerosine to give a 0.1% oil spray of each compound.

FORMULATION EXAMPLE 7

Oil-Based Aerosols

First, 0.1 part of each of the present compounds (1) to (148), 0.2 part of tetramethrin, 0.1 part of d-phenothrin, and 10 parts of trichloroethane are dissolved in 59.6 parts of deodorized kerosine, and the solution is put in an aerosol vessel. Then, the vessel is equipped with a valve, through which 30 parts of a propellant (liquefied petroleum gas) are charged under increased pressure to give an oil-based aerosol of each compound.

FORMULATION EXAMPLE 8

Water-Based Aerosols

An aerosol vessel is filled with 50 parts of pure water and a mixture of 0.2 part of each of the present compounds (1) to (148), 0.2 part of d-allethrin, 0.2 part of d-phenothrin, 5 parts of xylene, 3.4 parts of deodorized kerosine and 1 part of an emulsifier [ATMOS 300 (registered trade name by Atlas Chemical Co.)]. Then, the vessel is equipped with a valve, through which 40 parts of a propellant (liquefied petroleum gas) are charged under pressure to give a water-based aerosol of each compound.

FORMULATION EXAMPLE 9

Mosquito-Coils

First, 0.3 g of each of the present compounds (1) to (148) is mixed with 0.3 g of d-allethrin, and the mixture is dissolved in 20 ml of acetone. The solution is uniformly mixed with 99.4 g of a carrier for mosquito-coils (prepared by mixing Tabu powder, pyrethrum marc powder and wood flour in the ratio of 4: 3 : 3) under stirring. The mixture is well kneaded with 120 ml of water, molded and dried to give a mosquito-coil of each compound.

FORMULATION EXAMPLE 10

Electric Mosquito-Mats

First, 0.4 g of each of the present compounds (1) to (148), 0.4 parts of d-allethrin and 0.4 g of pipenyl butoxide are dissolved in acetone to have a total volume of 10 ml. Then, 0.5 ml of the solution is uniformly absorbed in a substrate for electric mosquito-mats having a size of 2.5 cm×1.5 cm×0.3 cm (prepared by forming a fibrillated mixture of cotton linter and pulp into a sheet) to give an electric mosquito-mat of each compound.

FORMULATION EXAMPLE 11

Heating Smoke Formulations

First, 100 mg of each of the present compounds (1) to (148) is dissolved in a suitable amount of acetone. Then, the solution is absorbed in a porous ceramic plate having a size of 4.0 cm×4.0 cm×1.2 cm to give a heating smoke formulation of each compound.

FORMULATION EXAMPLE 12

Poison Baits

First, 10 mg of each of the present compounds (1) to (148) is dissolved in 0.5 ml of acetone, and the solution is uniformly mixed with 5 g of solid bait powder for animals (Breeding Solid Feed Powder CE-2, trade name by Japan Clea Co., Ltd.). Then, the removal of acetone by air drying gives a 0.5% poison bait of each compound.

The following test examples demonstrate that the present compounds are useful as active ingredients of insecticides. In these test examples, the present com- pounds are designated by their compound numbers as described above and the com- pounds used for comparison are designated by their compound symbols as shown in Table 35.

TABLE 35

| Compound | Chemical structure | Remarks |
|---|---|---|
| (A) | 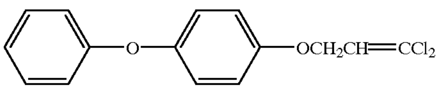 | Compound disclosed in JP-A 48-86835/1973, page 23 |
| (B) | 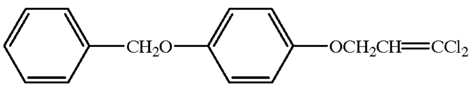 | Compound disclosed in JP-A 49-1526/1974, page 22 |

TEST EXAMPLE 1

Insecticidal Test Against *Spodoptera litura*

A 200-fold water dilution (500 ppm) of an emulsifiable concentrate of the test compound, which had been obtained according to Formulation Example 1, was absorbed at a volume of 2 ml in 13 g of an artificial diet for *Spodoptera litura*, which had been prepared in a polyethylene cup having a diameter of 11 cm. Ten fourth-instar larvae of *Spodoptera litura* were set free in the cup. After 6 days, the survival of larvae was examined to determine the mortality. The test was conducted in duplicate.

As a result, it was found that the present compounds (1)–(7), (9), (11)–(21), (23)–(25), (27)–(30), (32)–(34), (44), (56), (58), (59), (67), (84), (86), (89)–(104), (108), (110), (111), (114)–(118), (120), (121), (124)–(127) and (129)–(133) exhibited the mortality of 80% or more. In contrast, both compounds (A) and (B) for comparison exhibited the mortality of 0%.

TEST EXAMPLE 2

Insecticidal Test Against *Plutella xylostella*

A water dilution (25 ppm) of an emulsifiable concentrate of the test compound, which had been obtained according to Formulation Example 1, was sprayed at a sufficient volume over potted cabbages at the five leaf stage. After air drying, ten third-instar larvae of *Plutella xylostella* were set free on each pot. After 4 days, the mortality was determined.

As a result, it was found that the present compounds (1), (2), (4), (6), (7), (12)–(14), (18)–(21), (33), (34), (44), (58), (59), (67), (84), (86), (89), (90), (97), (98), and (108) exhibited the mortality of 80% or more. In contrast, both compounds (A) and (B) for comparison exhibited the mortality of 0%.

TEST EXAMPLE 3

Insecticidal Test Against *Cnaphalocrocis medinalis*

A water dilution (25 ppm) of an emulsifiable concentrate of the test compound, which had been obtained according to Formulation Example 1, was sprayed at a sufficient volume over the foliage of cupped rice seedings (Nihonbare). After air drying of the chemical solution, third-instar larvae of *Cnaphalocrocis medinalis* were set free thereon. After 4 days, the mortality was determined.

As a result, it was found that the present compounds (1), (2), (4)–(7), (13); (14), (17), (18), (21), (32), (34), (56), (58), (59), (67), (89), (93) the mortality of 80% or more. In contrast, both compounds (A) and (B) for comparison exhibited the mortality of 0%.

Industrial Applicability

The present compounds have excellent insecticidal activity so that they are satisfactorily effective for the control of noxious insects.

What is claimed is:

1. A dihalopropene compound of the general formula:

(I)

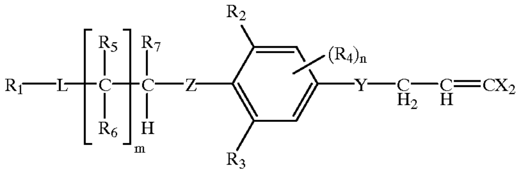

wherein m is an integer of 0 to 4;

n is an integer of 0 to 2;

X's are independently chlorine or bromine;

Y is oxygen, NH or sulfur; and

Z is oxygen, sulfur or $NR_{15}$ in which $R_{15}$ is hydrogen or $C_1$–$C_3$ alkyl;

$R_2$, $R_3$ and $R_4$ are independently halogen, $C_1$–$C_3$ haloalkyl or $C_1$–$C_3$ alkyl;

$R_5$, $R_6$ and $R_7$ are independently hydrogen, $C_1$–$C_3$ alkyl or trifluoromethyl;

L is C=W, C(=W) $NR_{13}$, $NR_{13}C$(=W), $SO_2NR_{13}$, $NR_{13}SO_2$, $NR_{13}C(=W_1)$—W, $WC(=W_1)NR_{13}$ or $NR_{14}C$(=W) $NR_{13}$ in which W and $W_1$ are independently oxygen or sulfur, and $R_{13}$ and $R_{14}$ are independently hydrogen, $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl or $C_3$–$C_5$ haloalkynyl; and $R_1$ is an optionally substituted pyridyl group.

2. The dihalopropene compound according to claim 1, wherein $R_{13}$ and $R_{14}$ are independently hydrogen or $C_1$–$C_3$ alkyl.

3. A dihalopropene compound according to claim 1, wherein L is $C(=W)NR_{13}$.

4. The dihalopropene compound according to claim 1, wherein the pyridyl groups is optionally substituted with $(R_{16})_s$ in which $R_{16}$ is halogen, nitro, cyano, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, ($C_1$–$C_2$ alkyl) aminocarbonyl, [di($C_1$–$C_2$ alkyl)amino]-carbonyl, phenyl optionally substituted with halogen, $C_1$–$C_4$ alkyl, $C_1$–$C_3$ haloalkyl, $C_1$–$C_4$ alkoxy or $C_1$–$C_3$ haloalkoxy, benzyl optionally substituted with halogen, $C_1$–$C_4$ alkyl, $C_1$–$C_3$ haloalkyl, $C_1$–$C_4$ alkoxy or $C_1$–$C_3$ haloalkoxy, phenoxy optionally substituted with halogen, $C_1$–$C_4$ alkyl, $C_1$–$C_3$ haloalkyl, $C_1$–$C_4$ alkoxy or $C_1$–$C_3$ haloalkoxy, benzyloxy optionally substituted with halogen, $C_1$–$C_4$ alkyl, $C_1$–$C_3$ haloalkyl, $C_1$–$C_4$ alkoxy or $C_1$–$C_3$ haloalkoxy, or pyridyloxy optionally substituted with halogen, $C_1$–$C_4$ alkyl, $C_1$–$C_3$ haloalkyl, $C_1$–$C_4$ alkoxy or $C_1$–$C_3$ haloalkoxy; and s is an integer of 0 to 4.

5. The dihalopropene compound according to claim 1, wherein $R_1$ is optionally substituted 2-pyridyl, 3-pyridyl or 4-pyridyl.

6. The dihalopropene compound according to claim 5, wherein L is C=W, $C(=W)NR_{13}$ or $SO_2NR_{13}$.

7. The dihalopropene compound according to claim 1, wherein $R_2$, $R_3$ and $R_4$ are independently halogen or $C_1$–$C_3$ alkyl.

8. The dihalopropene compound according to claim 1, wherein $R_2$ and $R_3$ are both chlorine, and $R_4$ is hydrogen.

9. The dihalopropene compound according to claim 1, wherein Y and Z are both oxygen.

10. The dihalopropene compound according to claim 1, wherein $R_5$, $R_6$ and $R_7$ are independently hydrogen or $C_1$–$C_3$ alkyl.

11. The dihalopropene compound according to claim 1, wherein $R_5$, $R_6$ and $R_7$ are all hydrogen.

12. The dihalopropene compound according to claim 1, wherein L is $WC({=}W_1)NR_{13}$.

13. An insecticide comprising, as an active ingredient, a dihalopropene compound as set forth in any one of claims 2, 3, 4-6, 7-12, or 1.

14. A phenol compound of the general formula:

[IV]

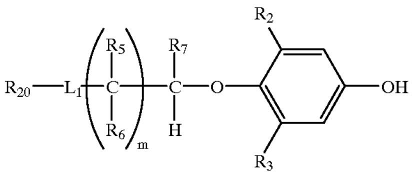

wherein $R_{20}$ is 2-pyridyl, 3-pyridyl or 4-pyridyl; $R_2$ and $R_3$ are independently halogen, $C_1$–$C_3$ haloalkyl or $C_1$–$C_3$ alkyl; $R^5$, $R^6$ and $R^7$ are independently hydrogen, $C_1$–$C_3$ alkyl or trifluoromethyl; $L_1$ is C=W, $C({=}W)NR_{131}$ or $SO_2NR_{131}$ in which W is oxygen or sulfur, and $R_{131}$ is hydrogen or $C_1$–$C_3$ alkyl; and m is an integer of 0 to 4.

15. The phenol compound according to claim 14, wherein $L_1$ is $C({=}W)NR_{131}$ or $SO_2NR_{131}$.

16. The phenol compound according to claim 14, wherein $R_2$ and $R_3$ are halogen or $C_1$–$C_3$ alkyl; and $L_1$ is $C({=}W)NR_{131}$ or $SO_2NR_{131}$.

17. A phenol compound according to claims 14, which is 3,5-Dichloro-4-(3-(5-trifluoromethylpicolinamido)propyloxy)phenol.

18. A phenol compound according to claim 14, which is 3,5-Dichloro-4-(4-(5-trifluoromethylpicolinamido)butyloxy)phenol.

19. A phenol compound according to claim 14, which is 3,5-Dichloro-4-(3-(5-trifluoromethylpyridine-2-sulfonamido)propyloxy)phenol.

20. A phenol compound according to claim 14, which is 3,5-Dichloro-4-(4-(5-trifluoromethylpyridine-2-sulfonamido)butyloxy)-phenol.

21. A phenol compound according to claim 14, which is 3,5-Dichloro-4-(3-(N-(5-trifluoromethyl-2-pyridyl)carbamoyl)propyloxy)phenol.

22. A phenol compound according to claim 14, which is 3,5-Dichloro-4-(4-(N-(5-trifluoromethyl-2-pyridyl)carbamoyl)butyloxy)phenol.

* * * * *